(12) United States Patent
Norton et al.

(10) Patent No.: US 10,962,543 B2
(45) Date of Patent: Mar. 30, 2021

(54) METHODS OF TREATING AND PROGNOSING NONHEMATOPOIETIC MALIGNANT TUMORS

(71) Applicant: Memorial Sloan Kettering Cancer Center, New York, NY (US)

(72) Inventors: Larry Norton, New York, NY (US); Ross Levine, New York, NY (US); Maria Kleppe, New York, NY (US); Elizabeth Comen, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/533,911

(22) PCT Filed: Dec. 4, 2015

(86) PCT No.: PCT/US2015/064016
§ 371 (c)(1),
(2) Date: Jun. 7, 2017

(87) PCT Pub. No.: WO2016/094248
PCT Pub. Date: Jun. 16, 2016

(65) Prior Publication Data
US 2017/0363635 A1 Dec. 21, 2017

Related U.S. Application Data

(60) Provisional application No. 62/089,148, filed on Dec. 8, 2014.

(51) Int. Cl.
*G01N 33/574* (2006.01)
*C12Q 1/6886* (2018.01)
*A61K 31/7068* (2006.01)
*A61K 31/7052* (2006.01)
*A61K 31/52* (2006.01)
*A61K 31/573* (2006.01)
*A61K 31/704* (2006.01)
*A61K 31/7048* (2006.01)
*A61K 31/506* (2006.01)
*A61K 38/17* (2006.01)
*A61K 39/395* (2006.01)
*A61K 45/06* (2006.01)
*A61K 31/00* (2006.01)

(52) U.S. Cl.
CPC ..... *G01N 33/57484* (2013.01); *A61K 31/506* (2013.01); *A61K 31/52* (2013.01); *A61K 31/573* (2013.01); *A61K 31/704* (2013.01); *A61K 31/7048* (2013.01); *A61K 31/7052* (2013.01); *A61K 31/7068* (2013.01); *A61K 38/177* (2013.01); *A61K 39/3955* (2013.01); *A61K 45/06* (2013.01); *C12Q 1/6886* (2013.01); *G01N 33/57496* (2013.01); *A61K 31/00* (2013.01); *C12Q 2600/136* (2013.01); *C12Q 2600/158* (2013.01); *G01N 2800/52* (2013.01); *G01N 2800/56* (2013.01); *G01N 2800/7028* (2013.01)

(58) Field of Classification Search
CPC combination set(s) only.
See application file for complete search history.

(56) References Cited

PUBLICATIONS

Mirza et al (Mol. Cell., Biochem., 2010, 342:101-109) in IDS.*
Wang et al (Cancer Biotherapy & Radiopharmaceuticals, 2013, 28:34-44) in IDS.*
Juergens et al (Cancer Discovery, 1:2011, 599-607).*
Howell et al (Pharmaceuticals, 2010, 3:2022-2044) t.*
Nzula et al (Cancer Research, 2003, 63:3275-3280).*
Nielsen et al (Clinical Cancer Research, 2012, 18:3281-3292).*
Chang et al (BMC Cancer 2013, 13:55).*
Denkert et al (Lancet Oncology, 2018, 19:40-50).*
Connolly et al (Clinical Cancer Research, 2017, 23:2691-2701).*
Howell et al (Pharmaceuticals, 2010, 3:2022-2044).*
Kleppe et al (NPJ Breast Cancer, 2015, 1:15005).*
Ramakrishnan et al (Cancer Research, 2013, 73:1-11).*
Itzykson et al (Leukemia, 2011, 25:1147-1152).*
Watson et al (Nature Review Genetics, 2013, 14:703-718).*
Im et al (Leukemia, 2014, 28:1774-1783).*
Cancer Genome Atlas Network, Oct. 2012, "Comprehensive molecular portraits of human breast tumours," Nature, 490(7418):61-70, published online in Sep. 2012.
Ellis et al., Jun. 2012, "Whole-genome analysis informs breast cancer response to aromatase inhibition," Nature, 486(7403):353-360.
Acharyya et al., Jul. 2012, "A CXCL1 paracrine network links cancer chemoresistance and metastasis," Cell, 150(1):165-178.
Karnoub et al., Oct. 2007, "Mesenchymal stem cells within tumour stroma promote breast cancer metastasis," Nature, 449(7162):557-563.
Kurose et al., Nov. 2002, "Frequent somatic mutations in PTEN and TP53 are mutually exclusive in the stroma of breast carcinomas," Nature Genetics, 32(3):355-357, published online in Oct. 2002.
Hu et al., Aug. 2005, "Distinct epigenetic changes in the stromal cells of breast cancers," Nature Genetics, 37(8):899-905, published online in Jul. 2005.
Granot et al., Sep. 2011, "Tumor entrained neutrophils inhibit seeding in the premetastatic lung," Cancer Cell, 20(3):300-314.
Grivennikov et al., Mar. 2010, "Immunity, inflammation, and cancer," Cell, 140(6):883-899.
Orimo and Weinberg, Aug. 2006, "Stromal fibroblasts in cancer: a novel tumor-promoting cell type," Cell Cycle, 5(15):1597-1601.

(Continued)

*Primary Examiner* — Laura B Goddard
(74) *Attorney, Agent, or Firm* — Stroock & Stroock & Lavan LLP

(57) ABSTRACT

Provided herein are methods of treating a nonhematopoietic malignant tumor in a patient and methods of prognosing a nonhematopoietic malignant tumor in a patient, comprising administering to the patient a therapeutically effective amount of an agent that preferentially kills or inhibits proliferation or activity of leukocytes relative to nonhematopoietic cells.

6 Claims, 3 Drawing Sheets

Figure 1:
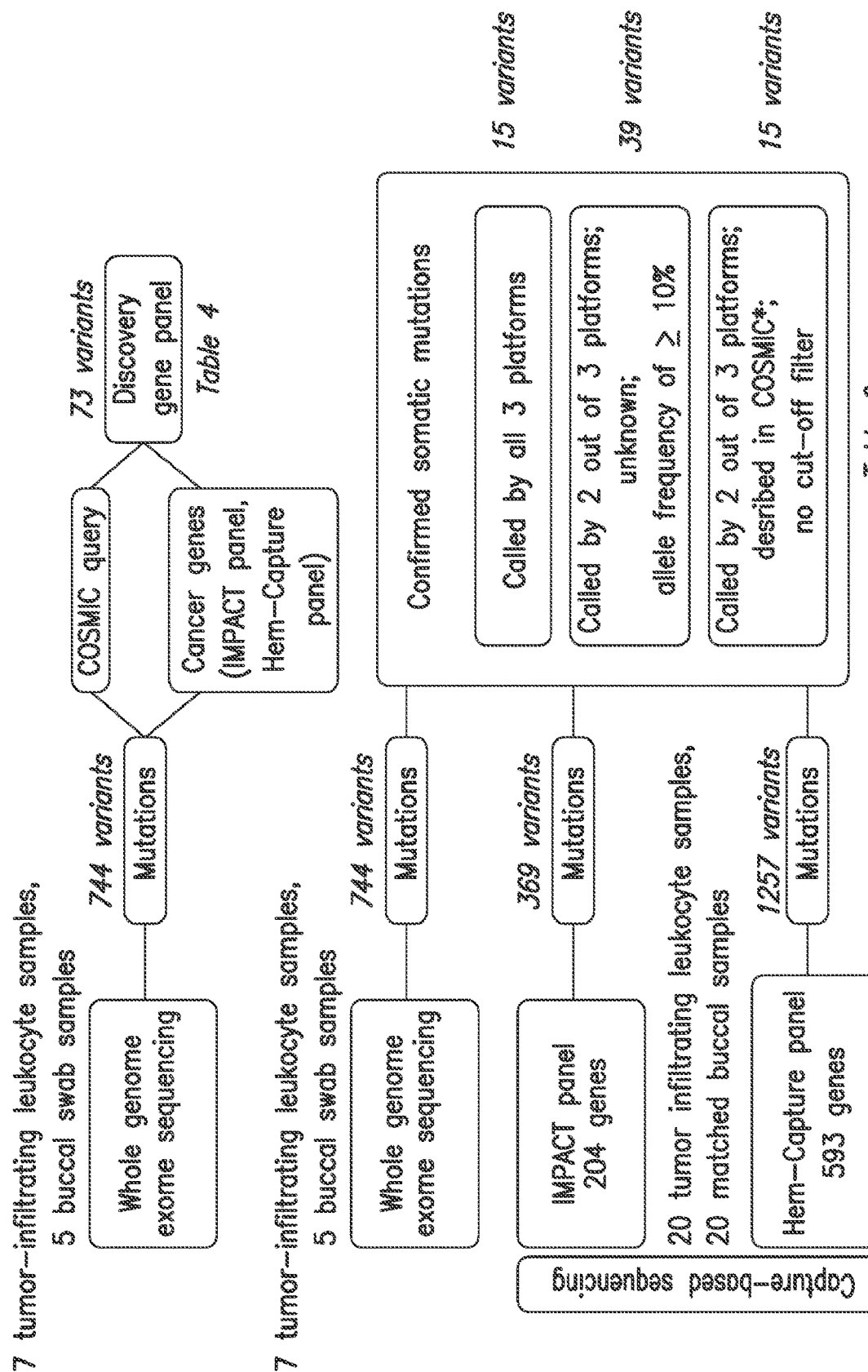

Specification includes a Sequence Listing.

(56) References Cited

PUBLICATIONS

Li et al., Sep. 2012, "Cancer-stimulated mesenchymal stem cells create a carcinoma stem cell niche via prostaglandin E2 signaling," Cancer Discovery, 2(9):840-855, published online in Jul. 2012.

Mahmoud et al., May 2011, "Tumor-infiltrating CD8+ lymphocytes predict clinical outcome in breast cancer," Journal of Clinical Oncology, 29(15):1949-1955, published online in Apr. 2011.

Mohammed et al., Sep. 2013, "The relationship between lymphocyte subsets and clinico-pathological determinants of survival in patients with primary operable invasive ductal breast cancer," British Journal of Cancer, 109(6):1676-1684, published online in Aug. 2013.

Busque et al., Nov. 2012, "Recurrent somatic TET2 mutations in normal elderly individuals with clonal hematopoiesis," Nature Genetics, 44(11):1179-1181, published online in Sep. 2012.

Moran-Crusio et al., Jul. 2011, "Tet2 loss leads to increased hematopoietic stem cell self-renewal and myeloid transformation," Cancer Cell, 20(1):11-24, published online in Jun. 2011.

Quivoron et al., Jul. 2011, "TET2 inactivation results in pleiotropic hematopoietic abnormalities in mouse and is a recurrent event during human lymphomagenesis," Cancer Cell, 20(1):25-38, published online in Jun. 2011.

Ko et al., Aug. 2011, "Ten-Eleven-Translocation 2 (TET2) negatively regulates homeostasis and differentiation of hematopoietic stem cells in mice," Proc Natl Acad Sci U S A, 108(35):14566-14571.

International Search Report, Information on Search Strategy, and Written Opinion of the International Searching Authority, for International Patent Application No. PCT/US2015/064016, dated Feb. 25, 2016, 16 pages.

Mirza et al., Sep. 2010, "Demethylating agent 5-aza-2-deoxycytidine enhances susceptibility of breast cancer cells to anticancer agents," Molecular and Cellular Biochemistry, 342(1-2):101-109, published online in May 2010.

Wang et al., Feb. 2013, "5-aza-2'-Deoxycytidine enhances the radiosensitivity of breast cancer cells," Cancer Biotherapy and Radiopharmaceuticals, 28(1):34-44, published online in Aug. 2012.

Bovenzi et al., Jun. 1999, "DNA methylation of retinoic acid receptor beta in breast cancer and possible therapeutic role of 5-aza-2'-deoxycytidine," Anti-Cancer Drugs, 10(5):471-476.

Chang et al., May 1989, "Novel KI-ras codon 61 mutation in infiltrating leucocytes of oral squamous cell carcinoma," Lancet, 333(8645):1014.

Nzula et al., Jun. 2003, "Antigen-driven clonal proliferation, somatic hypermutation, and selection of B lymphocytes infiltrating human ductal breast carcinomas," Cancer Research, 63(12):3275-3280.

Modi et al., Mar. 2005, "A phase II trial of imatinib mesylate monotherapy in patients with metastatic breast cancer," Breast Cancer Research and Treatment, 90(2):157-163.

Loi et al., Mar. 2013, "Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98," Journal of Clinical Oncology, 31(7):860-867, published online in Jan. 2013.

Kleppe et al., Jun. 2015, "Somatic mutations in leukocytes infiltrating primary breast cancers," NPJ Breast Cancer, 1:15005.

Lyer et al., Oct. 2012, "Genome sequencing identifies a basis for everolimus sensitivity," Science, 338(6104):221, published online in Aug. 2012.

Welch et al., Jul. 2012, "The origin and evolution of mutations in acute myeloid leukemia," Cell, 150(2):264-278.

Howell et al., Jul. 2010, "Demethylating Agents in the Treatment of Cancer," Pharmaceuticals, 3(7): 2022-2044.

Office Action dated Oct. 7, 2019 in Japanese Patent application No. 2017-530336.

Ruffell, Brian et al., Proc. Natl. Acad. Sci. USA, Feb. 21, 2012, vol. 109, No. 8, pp. 2796-2801, DOI: 10.1073/pnas.1104303108.

Lanca, Telma and Silva-Santos, Bruno, Oncoimmunology, Aug. 2012, vol. 1, No. 5, pp. 717-725, DOI: 10.4161/onci.20068.

Denardo, David G. et al., Cancer Discovery, Jun. 2011, vol. 1, Issue 1, pp. 54-67, DOI: 10.1158/2159-8247. CD-10-0028.

\* cited by examiner

SEQUENCE LISTING

```
<160> NUMBER OF SEQ ID NOS: 2

<210> SEQ ID NO 1
<211> LENGTH: 135142
<212> TYPE: DNA
<213> ORGANISM: Homo sapiens

<400> SEQUENCE: 1
aaattagggc ttcgctttta aaaaaaatta cagaccaaaa aaagtgtggt tacacaatat      60
aactagtatt gacttaaggg tactgtgatc accatgcagt gatcccataa aagatgtgac     120
caaaataccc acttaaaatt tgaacgtcag tcatgtaaga acatgtaaaa gatgaaggga     180
atatttcaaa aacgactatc tgacgtaata tgatacttac tatgactcat atgggctttg     240
ttcttcatct catcttcaaa taaaaagttg atgattagaa aaaggagcat tagaaggggg     300
aagtaacact actcggcaat agagaaaaac tccggtcaaa ggaagagcat agttacagag     360
ctccgaatgt cagggaaaat caagcatccg tcattcggaa ttagctctgt atcggtcggt     420
ttcttcatta cttaattgta cgggggggaaa ctacttcaaa gtaagggctc ttacgagagg     480
caacttaagc atttgaaagt gcaggtttat ttcctcctag cgagaagtag ggggtcacta     540
gtgagaaacc tatttcaatc tgtgagacgc ccccttctac tcagcccacg tggctaaagt     600
aaacagaagg tgggccgggg cggggagaaa cagaactcgg tcaatttccc agtttgtcgg     660
gtctttaaaa atacaggccc ctaaagcact aagggcatgc cctcggtgaa acaggggagc     720
gcttctgctg aatgagatta aagcgacaga aaagggaaag gagagcgcgg gcaacgggat     780
ctaaagggag atagagacgc gggcctctga gggtaaggtg ggcgcaagcg gaggtgtggt     840
gcggggagag gtgccagtgg gtggaggcgg gggccagagc gagggcacgt gcgggtacac     900
tccggaggag gtgggtgcgc gcggggggcgt gtgcgcggga cctcgaagtg gtggtggagt     960
```

```
gcagaccagc aaaaagtttc aaagggaaat cttagatgtc acgtctttgt ccaggcaccc   1020
gtgccatccc aacctccac ctcgccccca accttcgcgc ttgctctgct tcttctccca    1080
ggggtggaga cccgccgagg tccccggggt tcccgagggc tgcacccttc cccgcgctcg   1140
ccagccctgg cccctactcc gcgctggtcc gggcgcacca ctcccccgc gccactgcac    1200 ggcgtgaggg cagcccaggt ctccactgcg cgccccgctg tacggcccca ggtgccgccg   1260
gcctttgtgc tggacgcccg gtgcgggggg ctaattccct gggagccggg gctgagggcc   1320
ccagggcggc ggcgcaggcc ggggcggagc gggaggaggc cggggcggag caggaggagg   1380 cccggggcgga ggaggagagc cggcggtagc ggcagtggca gcggcgagag cttgggcggc  1440
cgccgccgcc tcctcgcgag cgccgcgcgc ccgggtcccg ctcgcatgca agtcacgtcc   1500 gcccctcgg cgcggccgcc ccgagacgcc ggccccgctg agtgatgaga acagacgtca    1560
aactgcctta tgaatattga tgcggaggct aggctgcttt cgtagagaag cagaaggaag   1620
caagatggct gccctttagg atttgttaga aaggagaccc gactgcaact gctggattgc   1680
tgcaaggctg agggacgaga acgaggtcag agcgcttctc ttatgccgcg aaactctccc   1740
tttcttctcc ccttcgcttt ttctcgggct tccagggact ggggagcaaa ccctgtagtg   1800
tcacccacaa ataccaagag ggaagaggga agcttcacaa attactggag cctcttcaac   1860
atggctgaca aatatagttt taattccctc taccctttt aaacctgtag ttctgtgttc    1920
tcttctctcc tcctaatgct cgtccccctca tctcccagaa aacttacctt tgtgcctccg   1980
acgagccggt ttcccggcct ttttaatcc tcagaaaagt gattttaaa tttgctttcc     2040 tttctaaaat agttcagctt tgggggcact acttttccct ttaatcctct tccctgttt    2100 ctttcgtgta agtgaaacga gtctcccgtt tatcctgaac aacctcagag agaacactga   2160
tagggtgttt ttcgacccct ttatcagctg tagggtctgg gtctgggttt gtgtctgcct   2220
cctcctacct tcttatcccc ctttagggg ctgtacgaag tgaatgtcac agggagtgga    2280
attggagtac actgagtggg ttttttttt cctaagtcc gcgcgttttg ttagcggcgc     2340
tgagtgaaag aggaaagaat agttctctg gttccccaaa caagaccaga actcactttt    2400
ctcaaggtac ataagtcagc gctgggctga gccttccagc ctggggaatg tatgtaagag   2460
aatttatgga caaatctgtg tcccggcttt gtgcttctcc cgaatcagct tcgtttggtt   2520
ccttggtaag tgacaggcag acacaaaggc aggcgcaggc ccggggaggg ggcgggaggg   2580
ggtggggagc gcagcgttgg agttgcaaga ctgcaaggtc aggggcgcct aaagaaatga   2640
aacccaatcc cagcaaagaa gtgaagagca gatttataac agtccatccc aaatttctct   2700
ttggcttctc tctttggtct ttcatctctc tgcctttctc tctgtgtctc ctctctactc   2760
tttcttctct ctctctcata cacatacaca cacacacaca cacacacacc tcactcgcat   2820
cttgctgaat cttttcactg ggactgcttg tctagtttta ttaagctaat agggtttgta   2880
tggagagttt tctacctatg acataatgaa gtgtggcctg gatagactcc tggaaaggcc   2940
gaaaatgaaa tataagtgtt atttgctggt tattcccctc atgatatact tttaattaca   3000
ttgagggagt tctccctttct tcatctaatg tttaagaatt gagaaaaggc ttattttcca  3060
gcggtaaaat ttagtgcata aaatttagtg aaatatttat atatttacgt gtctaggag    3120 tggaatacat tcatgaattt aatatctcaa atcacacatt gtgcttttc cccttcagtc    3180 agggattata atgggaaacc caaattcaaa gatattcatc aacaaatgat ccatcatagg   3240
aataagattg tatcttaagg gaagttggga ttcacagaga aaagacattg gtttggtttg   3300
gtgtgatact gtgggtattg ttgcctggct aatgaaatca ttacatttgc attttaatgg   3360
```

```
aaagttgaaa tactaagggg agttatgttc ttttacatgt ttgtatgtgt gcttaataat    3420
gtttggaata gaatataaat ttaaacacaa taaatattga ttttttttaaa tgttaataag   3480 cagagaacgg ttaatgaagt gttggataat caaactgaag tttagaagac aatttatagg    3540
attaaaaaat ggatagaagg aaaaacacaa taatagatat ttctccataa gtcgaatttc    3600
caaaactatt tgtcctcgat agttcacttt gtaactttct attttgatct ttgttaattt    3660
aatgtagttt gctttaatca ttgatacgtg gggttctttc acatgattac aagggagaag    3720
cattactcat ctctgtggaa tagaaacggt tcattggtta gttcttattt gccctaaaat    3780
taaaacaaaa attaggattt taccattaat gctgttcatg gtaaactatc gagaaaacta    3840
tggttaatta ttccagcaat tcagaattaa aaacaattcc ttttgctaac aaactaatat    3900 ttacttttttg gggacaactt ttcaaatgtt gtggtatata ctgtcttcag gctactcaac   3960
taataataga tacaacattt tccactcaat aaataagaat aactacattg gttaataatt    4020
ttgaatacaa ctatgaaggc ttgttttttc ctgtcatcaa atttagattc ttgttatttt    4080
gtgcatccta cttttatact gaaaatagct gctaattaat actgtataaa gtatttcagt    4140
gattataagg aagagatgtg tatgttagtc actttatcct ttgttggaaa agagaaatta    4200
ttttaataag tatggggtag tttacaataa aagcataac ctcagttctt tctttaccat     4260
atatgtgatc atactaccta ggtgctccaa aaattccata ggactgtctt gggttattga    4320
attttaggaa catgataatg gacaataaca agatagatag cttttcttaa ctatgacatt    4380
gttttgctta ttttcttatt gaactaatca tcaatgagaa attaagttgc agtgagagaa    4440
atcccttgct ttgtttaaat tgtcatattt gccaaactct tcttaaggct ttaattaggt    4500
ctgatgtgcc agtttatgcc agaagccgga ggaattgata tgattttgag gcagtggcac    4560
atggtcctac tagacattgg caagtgaata tcacttccag aacaagtgaa gtgcacctgc    4620
caaggagttg ttatgaaaga attccaaagt ccttattggg cactggtctt gtattaggta    4680
acaacaactg gagttaatgt tttagtttca cttgttgaag ttaaaagttc cctatcaatt    4740
cttctaagac tccaccccca aacaatgttg taagtcaaat gtcactattg aaatgtatttt   4800 ccttaattac tgacctcatt aagaagccct tcttatgatt cataggcaca cctcacagaa    4860
actctatttt ccatcctgcc caaagtctga gtaggtaaat tcttatgaat tcttatgaaa    4920
ttaccttgaa ataaaatatc ttcaaaagtt acgatgcta gacattgtat aatgtcaata     4980
ttttagaata tctaatatttt agaaaatctt agatctactt tttatgcttt aattgcttct   5040
aatgcaagtt aaattgtttt tgttgttatt gttttaatag aatttcatag tcttatctag    5100
caatttcaaa tcgctggaaa gagtcatctt tgttatataa ataaccatgt agactgtttt    5160
aatgttattg tttcctacct tgggaacagg ctaaactttt ggaccagctg tcagtatttg    5220
ttcatcagaa taacactttg tcaatgatta ttctaccatt gcacagtagt tcttaaggat    5280
agtaatggta ccaaagccag cagcaataga atatctccca agccaacttt acaattggag    5340
ccttcactgt gggaaagacc agttgccaag tagagctggt ggttatctgg gaaactgtgc    5400
tgaagaacac aaccacaaat gattttgcca aatatacagt atttacttgg tctagatctc    5460
caatttctat ttctactcac tgccaaaact gagtgaatac tgtgacatta ttgaaggagg    5520
ttatgcagta catctgttgg tttggtatat agtaggagag aagggttcca ggagggaaag    5580
gggaaagtca gagcatgtga atcactgtga ctacaatcca aaaagaatta tgtatgtctg    5640
ctatttccag cattattttt gtcctatatt gtacattgca gagacttgct gacttaaaat    5700
```

```
agatatataa tcttttttctc aaaagaatag atatttggtt gtccattcca aataacaaat    5760
tttggatggg cgtggtgact catgcctgta atcctagcac tttgggaggc caaggtgaga    5820
gatcacttga ggccaggagt ttgaaaccac cctgggcaac acagtcaggc cccagtctct    5880
acaaaaaatt taaaaagtta gtggggcatg gtggtacatt cctgtagtcc cagctactca    5940
ggagactgag ataggaggat ggattgagct caagtgttct aacttatagt gagctctgat    6000
cacaccactg cgctccagcc caggcaagag ggagagaccc tatctcaaac agcgacaaca    6060
acaaaaccaa acaaacaaaa aagcacattc tatcagcttt gatttatgtt ttcttcattt    6120
gtaatgacat gtagttaaat gtgtcatact tcaaaaagaa gaaacagata gtaggtggat    6180
tttcaatata atatatatta gatatagata atatatattt tcaatatata atatatgtaa    6240
aaataaattc agtgataata tcatcctacc tgcagtttta agaattcaga actcaggcca    6300
ggtgtggtgg ctcattctgg gaggggaagg caggaggatc acttgaggcc agaagttcta    6360
gaccagcctg ggcaacatag tgagataccc gtctctattc aataaaaata aaaataaaaa    6420
taattcagaa ctcaatgctt tatactcact gaaagttgtt cctctaaact gacttgaaat    6480
catgttccaa ataaactgag aattaaagta agagacgagg ccggttgtgg tggctcatgc    6540
ctgtaatccc agcactttgg gacgacaagg caggtggatg acctgaggtc aggagtttga    6600
gaccagcctg gccaacatgg tgaaaccctg tctctactaa aaatacaaaa attagccggg    6660
catggtggca cacaccagta atcccagcta ctcaggaggc tgaggcccga gaatcacttg    6720
agcctgggca tggtggctca tacctataat cccagcactt tgggaggccg aggcaggtgg    6780
atcacctgac gtcaggaatt cgagaccagt ctggccaaca tggtgaaacc ccatctccac    6840
taaacataca aaattagctg ggtgtggtgg cacatgcctg tagtctcagc tattctggag    6900
gctgatacag gagaattgct tgaaccctcc cgggaggcag aggctgcggt gagccgagat    6960
ggctctgctg cactccagcc tgggcgaggc agagagactc tgcctcaaaa aaagaaaaat    7020
aataataata aataggagat gaataaattg ggataaagtg ttttttgaagg acagtctagg    7080 atataaaatg aactggttgt ttgactaaaa atactacaaa tgtttctttc aaattacatt    7140
tcttttttgt ctattggaag gtaggcactg atttctatgt cttctatttc cctaatagaa    7200
cctactgttg acctctcagt caatatttaa tggatgatat agaactagtg aaaaaccatg    7260
caatttaact agaaaaaaaa agtataatct attttctttt cctttttctt tctttctttc    7320 tttcttttt tttttttttt tgagacggta tcttgctctg tcacctaggc tggagtgcag    7380
tggtgtgatc tcggctcact gcaacctctg ccttccaggt tcaagtgatt ctcttttctca    7440 gcccccagag tagctgggac taggagcgtg ccccaccaca cctggctaat ttttctattt    7500
ttattagaga cagggtttca ccatgttggc caggctgatc tcgtactcct ggtctcaggt    7560
gatctgcctg cccgggtctc ccaaagtgct gggattacag gcatgagcca ctgcacctgg    7620
tctaatctat tttcaatgta taagagaaaa atagtgttaa gtgtcttggt gatggtgatg    7680
atggtaggag taatggtgtg ttttccttac atttaatttc tacaggctat ggcaattgcc    7740
ctataaaagc cacccatttt aagcacaaaa gtgaatggtt tttagtaaac ttatatggga    7800
tcatatattt ttaattgaaa tatttttttga gttaattata gattcatatg ccattgtatg    7860
aaataataca gagagattcc acgtatactt gctcaatttc ccccagtggc aacactttgc    7920
aaaactataa tatcatatca catcacatgc aaaaactataa tatcatatca caaccatgat    7980
actgacattg atgtggccta ctaatcttat tcagatgtcc tcagtttaac ttgtactcat    8040
ttgtgtgtgt tttgttttat accatttagt cacatgatca catattttta aacctttttt    8100
```

```
tctcaaaaca gagaagttta gcacaaaagt ttagcaattt atcaatcttg tgattgtgct   8160
gttatgccat attaaaatgt gtgtcagaat gtaagttttt gttttcttaa aagtccttt    8220 tttgatagaa tggcctttat gttaaaaata ttttaagttg ttttgtgaca gtgtaagtcg   8280
atgtcattta attctcatca caccctaga gataggtatt attcttatcc ctatttatga    8340
gtgaggaaac tgaagcccag tgaggttaaa taacttcctt aagttcatac agcctataca   8400
tggcttaggc ttagccagca tttgagttaa gcagtctgtc tctagtgcca aatcttttaa   8460
tcactatatt atacttcatc attatcattg atagctgtaa aagtgtataa tgtggactat   8520
gtagagaaag tcataaaagg agatttaaaa tgcatacagt tgttcacatg aaaacttgta   8580
gccaaatgtt cattacagca ttattaataa tggtaaaaaa tggaaacaac ccagatgtct   8640
atcatgtcat gagtgaataa acaaattgtg gtatatccat acagtgaaat attattaagt   8700
agtataaagg aatggattat tgataaatgc tgtcacatag gtgaatctga gaggcacaag   8760
aaaggccaca tatgatatgc tttcaatttt aagtaacgtc cagaataggc aaatctaagg   8820
agacagaaag ttggctagtt attactaggg gctagggatg ggagggaggt gactcctaat   8880
aagtatgaga tttcttttgg tgatgatgaa aatgttctat aattagatag taatgattgc   8940
ccaactcttt gaatatgctg aaacccactg aattatatgc tttaaaagga tgaatttatt   9000
gtatgtgaat tatatttcaa aaagctgttg ttataaaaat gaatgtagtt gagttatttg   9060
gtttatttta tgtcagaaaa tgtcttacat ctcatgcaaa agaaatgcag gaactatttg   9120
gattgaatga ggctaagcat atctttctag gaagatggca tcaaggagtt ttattatgcc   9180
tgtaatcctg gcactttggg aggccaaggc gggagaccag aagtttgaga ttagtctggg   9240
caacatcctc ttatagatga gaaggatact taatcactca aaagttggca ttgtgttttg   9300
tgataacaat agcctttaga gctcatatgg gaagattcaa tagatagtga taggttatat   9360
gacttggtaa agagggctta atgtataggt gcaagaaact ttctcagatg tctttagtta   9420
cctagccatt cagttcagga gatgtaaccc aagtgttaaa aggaatgtga ctgggtgcgg   9480
tggctcacac ctgtaatccc agcactttgc gaggcggaag tgggtgggtc tcttgagctc   9540
aggagttgga gacaagcctg gcaacatgg caaaaccccca tccctacaaa aaatgcacaa    9600
attagctggg tgtggtggca catccctgta gttccaggta cttgtggggc tgaggcggga   9660
ggatggctcg agcctgggaa gttgaggctg cagtgagcca tgttggtgcc cccacacttc   9720
agcctgggtg acaaaatgag accctctctc tcaaaaaaaa actataaaaa ttgctgttct   9780
tgtttaaatt actacaaagt gcagtttaat ctagaaataa taacaaatta ctagatttgg   9840
ggggttatta atgtcttatc tatgtgaaaa cagaagggca atgcagggca gagaataaac   9900
ttcaaaactt tgagtttgtt aactgtttat atctccactt gtcatgtttc agattttaaa   9960
gttaaaatga caaagtatct catagggttt aaacaagtga ctcttttcct gttaactgat  10020
actgtggcat gttgaagatg taaaataagg ttgaaaagga aattgctttg cagcagtctt  10080
cataatgcca ggacaaagtg agaaacaggg tcagaatgat gatggctctc catctttgct  10140
acacatggct gcaagtattt acaaatacca gcagaacttc tacaaaccac ttacaggtaa  10200
aatgagtgca gatttttaac actagtccct atggaactat gacttgtagt tttggacaca  10260
cagggtgaat tacttggggt tgattgtatt tgaatttcta accttatgta attctagata  10320
ccagacattc ttgttgtgca atgcttctct ccctttttat tctcatgaga atgctgggtt  10380
gcagccggtt ggatcccata ccttgggacc atgactgata actggagtgg agaaaattca  10440
```

```
ctgatctgga aaggttgagc tttagggttc agagacttat ttaaggtaca catgtgattg    10500
tacccaataa ggaagtatat tggctttata taattgttat gatcacttgt tcaatgagta    10560
actatagaat tttactttt aagagtatga tcatagcatc tacttgtagg tttgttgagt    10620
atgtttgaca agcccaagat agatgctcat gttagaccca ttaagaagtt ggtgtagtga    10680
tggttatgga aagcagtaag atagaattta ggttctgttc tccttactgg agaaatgact    10740
agcttacttg tcttcactct ctcttgtttc tctcaaaact ttgtgaacca cctcagctga    10800
ctataaattt ttgtactagt atctccataa ttttaaaaaa gttgttcaca gtttgagtg     10860 tagtacttca tctttgcttt ttaatgcact tccaaaaaat gtaaatctgt tctcgcatat    10920
taggaacatt ttgatttgtt gtttatttt agctttgctt tttataagta atttatacag     10980
aaggtacacc atattcaaaa gaagaaaaat gggctgtgaa ttttgctga tgtactactc     11040 tcttcaaagg gaattgccta tgttcaggca tagaaatgca ggcagtctga catttaggta    11100
tgccatacag agtattgata ttttaattt gctacttta acattttgag atttgtcaca     11160
gtttgttctg tgggtgggta aaagtaatgg taatttaat tacagttgtc gtgcctcatt     11220
agccattgct aaaacctgcc ttaccaaatc acttattttc ttgatgcagt gttaaatcta    11280
gcttctatgt ccaggttata cattaatgag aacattcacc catctctcaa atgggttatt    11340
atagtatttt ctcctgaaat agatgatgca taaaaaaag taaaaagct tcaataggga     11400 taatgaaagc cagataacat agcatggtat atgagttatt cctcccgttt ttcttacctg    11460
tctgcactaa gaagggcacc cattaaatac cataattatt agttgtgctg cctctgaagt    11520
agagcaccag aatgtgagag taatacaatg agaccacacc cagattctat ccataacata    11580
ctgtcctggt cttattaatt ttttaacct gtttgttctt ttagcacttt tcctgctttt     11640
gtttgaagtc tcttgctttg aagttataga attttttatat ttgccattgg ctgtaaagtt    11700
atctcagctc ttttataact tttcattata tttgcattaa aaggatcact ttgagcaccc    11760
tgtaattaat tcagatgatt attagcttt ttgtttgttc tactgtgcac tctcctatat     11820
acattataac agaagaaaaa accatttcta caaatacagt gtctgatagt tcatcaaatc    11880
agaatgagca tcttaaaaag tgaattatta aaatattaat tcatttacat tcctattta     11940 atgtaccaaa tgtaactgat gaaagaaga ataccataaa tgggtacctt tcaaaaatga     12000
aggaaaaaaa aatctcacaa ctaaagattc ttaccatata aattatttat tttagtaaat    12060
aattatttta gtacaaacag atacatttta gcaggaaaaa acacacttta aaccttgttt    12120
tatagatttt atctttcttc caatctagcc actgaaatgg ttttttctcc agtgaagtta    12180
tattatctac ataagttgaa tttaaaacaa ggttgtattt taattttgca gttgtctgcc    12240
acattacgct tgtggaaaaa cactggcaga aagcaaagct aatagacatt tgctgttgg     12300 ctcaccttat taatggctaa gatttaatta tgtatttcta ctgaaaagca aacttgaaaa    12360
agacgtttgg ttactaactg tgggaactaa aaatttttat ttatttttat ttttatttt    12420 ttggtagagt ctcactctct tgcccaggct ggagtgcagt ggcatgatct tggctcactg    12480
cagcctcctc cttctgggtt caagcgattc tcctgtctca gcctcccgag tagctgggat    12540
tataggcacc agccaccatg cctggctaat ttttgcattt ttagtagaaa cagcgtttcg    12600
ccatgtaggc taggctggtc tcgaactcct gacctctagt gatccacccc cttctgcttc    12660
ctaaagtgct gggattacag gcatgagcca tcggcctggc caacttattt actgttacaa    12720
cttacttact ttgaaacaac ttattactg ttaaaaaatg tggttcttat ttcaaataag     12780
attttatgga catcaactaa ttttttaaac atatattgta attttaaaac attttacca     12840
```

```
acattttca agagcatggg aaatctaggg tatggcattt taaagtgact ttaaagacac    12900
ttcttgggtt ttgttgaagt cagaatattt ttaaaaatac aatgagttta atttactact    12960
gacagatttt ctttaatttt ttttgcattg ttataattag tcatgcctta atcctcgggg    13020
tttttgggaa actatattta ggggttaaaa acttagttat tgacattgta attttctca    13080 gtattggtaa gaattcaggt gtttaaggaa tggagtttac ttgttttctg ttcacaaacc    13140
cattgtaaaa gatataatga atgtagatga aggtgaaatc cgagatagga agagaggtaa    13200
aatgctactt ttttttcctt cacccaagga aagccattga atactgaatg ggtcatgttg    13260
taatttaatt gggtgtaaat tataactttg taaatcattt gcctacttag tgtatatctc    13320 tggttttat gtaattcatc tcccataata tctcagttta cactgaagta aataagcaag    13380
caggaataag tcctgcaaat agaggaagta gaaagtgcat tcagaatgca ttgctgaaat    13440
tgtaaaactg atcctaaatt gaattaggta gagcagttaa tttagattac aagaaatgca    13500
acaggaaaaa aatattacag ttcttcctct tttttggaaa aaaaaaaga aagaaaagac    13560 aaataaatca cccttagtta gtgataattc cttgacatct gtatgctcat ttttagggcc    13620
aaaaaatagt aggcttctct ttggaaattg tagacgcttt ctctccttcc agttacacgc    13680
ggtcacatca acatttgaca cgtgggtacc gtgcacgtgg cagcagtatt tacaaacacc    13740
atcctaggat tccagagact cttatgtaac agtggagaga gtaagctttg agtgtctgtg    13800
ggcggaggaa tcaacacagt ttaattcatt gtccgggagc ccttgtctgg ctctgatagg    13860
gtcatgaacc aaagatcaag gtgtttaggt caggatattc cctaacgcat ggttttccta    13920
ccaaagcctc aaaagctgtg cctaaataca agattaatct ttttctttct ttctttcttt    13980 tttttttt ttttgagac ggagtttcgc tcttgctgcc aaggttggag tgcagtggcg    14040
ccgcgatctc ggctcactgc aacctccgcc tcaccggttc aagcgattct ccagcctcag    14100
acacccaagt agctgggatt ataggcatgc gccaccacgc ccggctaatt ttgtattttt    14160
agtacagacg gggtttctcc atgttggtca gcctggtgtt gaactcccga cttaaggtga    14220
tccgcttgct tcggcccccc aaagtgctgg gattacaggc ttgagccacc gcgcccagct    14280
aagattaatc ttttatgcc ctgcagcaaa caactagtca tgccaaacca tttttgtgat    14340
ttggggaaac atgagcagat gatgctttgg atctgattat aattcacagt gctcttgtaa    14400
tttacgtgag atttgcatac ctgcctccca gcctcacaaa atgcctttaa aaattacat    14460 cttggccagg atggctcacg cctgtaatcc cggcattttg ggaggccaag gcgggtggca    14520
agagatcgag atcatcctgg ccaacacggt gaaaacccgt ctctgctaaa aatacaaaaa    14580
ttagctgggc gtggtggcgg gcgcctgtaa tcccagctac ttgggagact gtggcaggag    14640
aatcgcttga ccccgggagg cggaggttgc agtgagccga gatcgcgcca ctgcactcca    14700
gcctggcgac agaacgagac tccgtctcag aaaaaaaaa aatcttgata tttgtatgca    14760
tcttaaaaag caagagaatt catgattgac ttcccaaact aaacggtctg accagaaaac    14820
actcaagaaa actcttggtt aatcatgctc cttagtatac cattatacct gcctctcccc    14880
tttccccatc ctctgtaaat tctctcaacc ttctctcatt tttaatttca taccaagacc    14940
tagagctaaa acaacaacaa caaagcttta agtctctata tttagggaat gtgcctccta    15000
tcccaaattg attttagag cttttcattt attttatca atacaaagca agttgaaata    15060
aaaaaaaagg catcaaaaat ttaaatgtct aaccacgtat atttggtata tgtatactgg    15120
tgctatgtat tagctgtaag cagactggtt tgaatattta aaatatgaac agaatttgag    15180
```

```
ttcttttttgt attgcatcta aggatcattt gagatggatg tcatcattta tcatccaaaa   15240
tagaagcctt cttgcctaac aaagaattgt aattagatca tcaaagatga aatttatagt   15300
aattgaaaag ttagctcatt tgactgcttc tttcatagac tgtgttttg taattacact    15360 acctttctaa agataggaaa aatcagagtc tctgaaatgt aatactataa gtgaaatatg   15420
tattttttaa aataaaggat cttttcccaa gagctaaacc aagcaccaaa tctgtttttt   15480
gggggttttt tggtttgttg gtttgtttgt tgtttgttt ttgacagagt ctccctctgt    15540
cgcccaggct ggagtgaagc ggagcgatct gggctcaccg caacctccgc ctcctgggtt   15600
ccagcaattc tctgcctcag gcttcggagt agctgggatt acaggcactc gccaccacgc   15660
ccggctaatt tttgtatttt tagtagaggc ggggttttac catcttggtc aggctggttt   15720
tgaactcctg acctggtgat ccactcgcct cagcctccca aagtgctggg attacaggtg   15780
ttttctttta agtaatactt ggtataagag aactttatat ctggaataat ttaaatatta   15840
tctgaccgaa tctattattc acatatgaaa actcaggttt tagccattta acatctaaag   15900
ctgttctcat ttagaggaaa ttaccaaaag agtgacttat ttaactaaca ataaaatcta   15960
aggatagata ttttttcatt ctgttgcaga gcaaaagcag ccttctggat atgaaaagat   16020
attacttctt tagtgtttat tacttataat ttattgtaca tttctgatac actgaattaa   16080
gatgcgatga gagtaggttg tagattttta aaagttctta tttgcgtgat ttatctactt   16140
gcttttttag tgtcggacta taaatgatgt atttctctca attatcctcg gcctaaatag   16200
taaaagcttg ggtgaaatta cttatgagta tacttttcct gcacagagca gagccattac   16260
tgaacactct cgagctttaa caaaaatcat cctatcttat attagaatat taatattttc   16320
cctctttctc ggacctttgt ttcacagtaa atcatatatg gatataagct gcaagtgctc   16380
agaatttgat taaggctata agttaatttc tactaaaaaa gggattcaaa tagaactttc   16440
atttggctgt actgtagttt cacttgaagg ggcaagcatg caataaacat tgacttattc   16500
aatgcatagg ctgtcttcat aaagatgaga ctgagtgaca gttgtctgtg tattataaaa   16560
tatcagaatg gtagattgaa tctgatgcat accaaggagc aatgtggaaa ttttaggctg   16620
ttcgtctttt ttcagttact actaagtgtg tgtatgtggt gtgtatgtgt tttgaacttt   16680
tcatatttaa gctgaatcct ctttggtaga aatggttaaa tagactatag taaaagtttc   16740
tgtctataaa tataaaatga aaaaatactg atatcttgca ttttccctaa tatgttgaaa   16800
gtgcacagaa tccttggggt cttttgtata aactgttttt atatggttcc tgtagaagac   16860
agctgaggca ccaaacacac acacaaaaca aacagcttgc ttggtgatga taacattcgt   16920
gcaagggagt tctctcttgc ataggagtcc caggttaccc taatgccttc ccacatggtc   16980
aaacacatgg agctttcata tttacacaca gctccagaat tctgaagcct gcagttgttt   17040
atcagtggga tacagggaga aagagtggtg tctatcttac taactgttta atgacctgga   17100
tcatgaatac tgatacagaa taagaaagca ctggcctgac tgcagggaa acatggtaga    17160 tgcctaaagg aggcttttcc ctgccccaca ctgtttattt taaactatca ttatcacctg   17220
aaaggagctt tcactttga acttaaaata gtagctttta accctgacaa gcaagtaggc    17280
actttagtat tcaagaactg aaggtgacaa gccctgagga gtgttactct ctttcataac   17340
caagctgact caaactcttt tagaagctag tgtagtaact taaccatctc taataatgtt   17400
gctgcatgcc ttcatagaaa cagttggagc aagagctgca ttttctttt tttaagtgtt    17460 tattatttac attttatttt tgaaaacatg ccattcctat tacatataga aatacttccc   17520
aaaatcactg tttgtataga actattttgc ttaacattag gattctattg aagagcctat   17580
```

```
atctgcaata atacggggag aaaatccccct tttgtgtgat agattaatga taaagagaaa   17640
gaaaaggtga gaagtaattt tgggaaatat gcaatgataa actagtggta tttattgaac   17700
taaacaccag cagctgtgct tagcatggat aattgcctaa aaggatgaga aaaaaaagta   17760
aaaatcagga gactataaat ttttcagtga agaataaatt ttctgtcaca aattatgaac   17820
attttaaata tgtatttaa acttttcct acttgtaaca aattatcaga cttttaatc   17880 taccttttt gagcttttca tcttttccc tgaattatag atttaattct gtgtatgtat   17940
gtgtgtgttt gaatatattt ttatatttta gatctagatt tgtaaactag agctgtttct   18000
aactgcttat aagacattgc cacctggatt gccaccactt tcactccagt atttcaataa   18060
acacttcatc aaaaacatag tttattttca aacatagaat catggattgc tacaagctga   18120
aaggacttta gagactcagt aaccccattc cttgcattta cagatgagaa aatggaggca   18180
tgggaaagta aagtcagttg cctcaaatag cgtaacaagc tatgtatatt tctaataata   18240
gctactattg attaagttct tatgttgggt taagtaccat gctaagcact ttccaaagat   18300
tatctaattc ttatgtcatc tatatttttg ttggtgctat tactctcctc actttactaa   18360
ggaagaaacc aagacatggg gttaaataac ttccctataa attttgaatt atctttggca   18420
tcatctccct atttgcaaat ctccattgtc tctttgttcg taatcaatgt aaatcaactc   18480
ttaaacagtt ggatgccaac aagcagtctg gtgtttggag ctcgaaagtt tcgagagaga   18540
gagagagaga gagagagaga gagagagaga gagagagaga gtgtgtgtgt gtgtgtgtgt   18600
gtgtgtgtgt gtgttccagc tttgttgagg tataattgac aagtaaacag tccacaaaac   18660
tgtacacatt taagagatac agtgtgatgt tttaatatac attgtgaagt gattattact   18720
atcaggctaa ttcacatgtc catcacctct cagtcatttt ttgtgtttac ggtgagaaca   18780
cttaagagct actcaaatgt agtcaaggat accatacagt actaactgta gtcaccatgc   18840
tgtacattag atctccagaa tgtattaaat attcatctgg cataactgaa actgtgtatc   18900
ctttgacaaa cctatttccc ctactaccca gcccatggca accaccatgt tactctctgc   18960
gtttatgagt tcgacttctt tagattccac atataagtga gatcatgcaa taggaagatc   19020
taatttagca tcctgacttt cctttttatt agctgtgtat gtcatattca ggttgcctta   19080
gcatttgtga atctgcttct ctacctgtaa aatgagaaca actaataatt cttatctcat   19140
ggattactga gaggatcaga tgaagtaaca taaataaaac atccagcatg ttacttggca   19200
aaattgtagt gattgaataa atatttgttt attcttcaag catgtgttga gcatctatgt   19260
atcaggcaag aagagagcca tcatctttac ccttctggaa tatacaggct cataggaaat   19320
aatcaatgct tgatctttt tttaaagcat aatgagatga aaattatagg actcatagac   19380
tggtcagttg aggaatttcc caggatgctt ccagcctctg ctcaaaaggt gtgaattccc   19440
agttgcctga ataggcgcca gagttggcat agctttctca gtattgggac ctgacaggga   19500
gattgcacaa gtgtaacagc acagcctctg aagattggct caaggggaa gagatgaagg   19560 attacttcca tcccttttat tgtttcaatc aagatatata ttatgagctc atagtaccat   19620
cctttcatga tcatccttta ttgtctttat tagatacaat gaaagatac aaatttgtcc   19680 atagaaatat taaatgatag caggcatgat ttaaaaagta ctaaggacta tagatattac   19740 tgttttcct ctattttgta tcatattttc aggaagaaga gacaacattt tggcatacct   19800
tgcttaaaga tagatgatag ccgggtgtgg tggctcagac ctgtaattcc agcactttgg   19860
gaggccgagg cgggcagatc acctgaggtc aggagtttga aaccaacctg gccaacgtag   19920
```

```
agaaaccccg tctgtaccaa aaaatacaaa aattagccag gcgtggtggt gggcgcctgt    19980
aattccagcc actcaggaga ctgaggcacg agaatcactt gaacccagga ggcagaggtt    20040
gcagtgagct gagatcgtgc cattgcactc cagcctgggt gacagaggga gacttcgtct    20100
cccaaaaaat aaaaataaaa aataattgtc ttggtgtgct aatcaggagc ttcctgtgag    20160
agtggaaatt ccttacatgg cagtgtcatg aaattttagg cccatgtgaa agatgttttt    20220
gagtgtctca aaatagttaa cggtttaaaa atacattatt tatgtgtcag aaactgcttt    20280
cattgaaatt gaagtttctt tgagaactag gatcatatca tgtatatcta ttgaatttcc    20340
cacaacaatt atcacgcaag caaatgaata gcagaccctc aataacactt actgatgatt    20400
attgccatgt ataagttggg atactcttga gtaccttttct aagtctgcat ttagggaaat    20460
acagaacaca aaatgaaatg tttgattggt tgcttagttt ccacagtgac ttttcaaaat    20520
gtataggagc atggtaacaa aactatttta aatactacaa tcttaagtat gcctttatta    20580 ttcttacccca caataatgca ttgctttaaa aaattgttta tcagtgtcag accatacctt    20640
tctgagtctc tactatgtaa gatgtgaaag ttaatattct tcaattccag ctactttttct    20700 tttcctgcct tctgtcaact cctgtattcc atatcattac ttcttattgc taaatttata    20760
atatttatat tctggtttgc atctatagtt aattctcttg tgcttcattt ctcagtgcta    20820
attgaaaaag aaaacacatc acttacaatg ccatgattgt aataaataaa attcactgta    20880
acacctagca gtatggttga acatgtagaa aaggaaaaag tgatcctgtg acactaaaat    20940
ttagcttgtt ctaaggatgc tactttaagc attagggtaa aatggattcc cttttgctaa    21000
attctttcag ttcctcaaaa ttatgccaca tttttgtttc tttcacattt ggacttagat    21060
tttcctgtaa gcattcaatt tttcttgaaa attttaattg catttttttta ttcttgttga    21120 cagaagaaac attttcatca tatcacaatt ttttttcaga tttcttaatt ataccatttg    21180
atgaatgaaa tacactttct tcttgaagtc tgattttcct gttctaattt agagtttctt    21240
ctcatttttc tcctggctat gtctattatt gctttagtct catgtctttg tatttgatta    21300
ttatttttct ttttactact gttttttcttc ttacagaaaa aaaagaaaa aaaaacaggg    21360 gttttttacaa atattgtgct gagtcttttac atgtccaaaa tgccttatat ttttccttat    21420
agtacattca taaattattg tgattagaac cataaattca aagtaatttt ctctcagagc    21480
ttgggaaaca ttggtacgtt gttacccttc atctaggatt gcttatgaga tagatatctg    21540
atgccagtct gattctgtct ttttttagata acttttttttcc ctattcatat gtttattagg    21600
atctttatct tttcacttct gaaattcctc cagatatggc tctgttaaaa tgtattcttc    21660
tcagcacttg atgattctgt acaatctgga aacaactgcc tttatttagc ttaaggtact    21720
tttcttccat tgtaccttttg attatttctt ccttctttttt ttcacccctat ctttatgaaa    21780 ctcatgttaa tggtgcatta gaacttgtga actgattttt cttatttatt aaattccatc    21840
acatattttt catctgttta tctctgtata ttttattttc tcaacttttg atattttgt     21900 taattgaaat ttaatttcca agaagtccat tttctattct ctgattgatt cttttttaatg    21960 gtagcctatt tcgtggctca aatcatataa aatgtattaa attttgtggg aaaattaggc    22020
aaacaaagaa aattaaattt tacctaacta tatctaaaaa caatacaact aaacttaaga    22080
aaagtgcgta tatgtgtaca catatacata tgcgtgtata tgtgtacaca tatgctacat    22140
atacatgtat atgtagtata tgtacatgta gtatatgtgt gtatgtatgt atatacacat    22200
gtagtatatc tatatacatg tatatgtaca aagaaaaaat atgtatataa tagttttcact    22260 gtacttttatt tgctcccctt ttaaaaataa cagtgctaga gttcatgact gactaatttt    22320
```

```
cagaacttgg tgtgtatggt tgtttattaa gccctcaata ataatgcttt agtattacag  22380
tgcccaggca tagtcagtga ctgtgctaat agtcctagca gtagcagttc atcctgtaca  22440
gatctaaggt gtaactattt tcatttctgg gcccttggag attctttggt tgtcttcata  22500
tcttttacct atcttgctgt tcaataacag gtaatagaaa aggagataaa acttaaatgt  22560
catcatttcc cactgcttaa cagtctttaa aaataaatgt gaaacccgta aggacgtaat  22620
cttgcctagc tttaaggaat gaaggaaaca ctagaaacaa cagagagaaa aggaataact  22680
gatcctccaa catgttctgt tgactctacc tgtaaagtat attcaggatc tgactacttc  22740
acaccatttc accaatttcc atctccattc aaaccacctt catgtgttac tttgaaaagt  22800
gcagtttccc tgtcatgggt ttccctgttt ctagctttgc tccccttct tacctcaccg  22860 tgggtttta cccaaacaaa aattcaagtg atcatttaaa aattaagtca ggtcatgcct  22920
ctcctctgct taaaaccatt aatgggtctc tgtttcactc agaatataag ccaaagccct  22980
tttcatgacc caccagtcct caagtgaatt ggctgctatt tgtgtttctg attccatttc  23040
ttgccactat tctccctcat tctattctaa tttccttggt tttcttgctg tcctggcaac  23100
aagaagagca tccttttcc tccaggcctt tgcacttgct gttccctctt cctggagcac  23160
ccttccttca gagagccaca ggtattgttt ctatctttcc ttctaatctc tccttgagtg  23220 ttacttttc agagataaat tccctaacca ttctatctaa cagaactctg actattgacc  23280 tgctttatt ttctctcttt ttttttaaaa ttttattttt ttattcccat aggttattgg  23340
ggaacaggtg gtatttggtt acatgggtaa gttctttagt ggtgatttgt gagatcttgg  23400
tgcacctatc acccgagcag tatacacttc acccttattcg tagtcttta ttcctcaccc  23460 ccttcccacc cttttcccct gagtccctag agtccattgt gtcattctta tgcctttgca  23520
tcctcatagc gtagctccca cttatgagtg agaacatatg atgtttggtt ttccatccct  23580
gagttacttc acttagaata atagtctcca gtcttatcca ggtcactgca aatgccatta  23640
attcattcct ttttatggct gagtagtatt ccatcttata aatataccac agtttcttta  23700
actactcacc gattgacgag catttgggtt ggttccacat ttttgcaatt gcaaattgtg  23760
ctgctataaa tgtgtgtgca agtatctttt tcatataatg acttttttcc tctgggtaga  23820
tacccagtag tgggattgct ggatcaaatg gtagttgtac ttttagttat ttaaggaatc  23880
tccacactgt tttccatagt ggctgtacta gtttacattc ccaccagcag tgtagaagtg  23940
ttctctgttc accatatcca tgccaacgtc tactattttt tgatttttta ttgccgttct  24000
tgcaggagta aagtattgca ttgtggtttt gatttgcatt tccctgatca ttagtgatat  24060
tgaacatttt ctcatatgtt tgttggtcat ttgtatatct tcttttaaa attgtctatt  24120 catgtcctta gccacttttt tgataggatt gtttgttttt ttccttgcta atttgttgga  24180
gttccttgta gattctagat attagtcctt tgccggatgc atagattgtg aagattttct  24240
cccactctgt gggttgtctg tttacgctgc tgactgttcc tattgctgtg cagaggctct  24300
tttgtttaat taagtctcac ctatttatct ttgttttgt tgcatttgct tttgggttct  24360
tggtcatgaa gtctttacct aagccaatgt ctagaagggt ttttctgatg ttatcttcta  24420
gaatttttat agtttcagca cgtagattta agttttgat ccatcttgag ttgattttta  24480
tataaggtga gagatgagga tctagtttca ttcttctata tgtggcttac cagctatccc  24540
agcaccattt gttgaatagg gtgtccttta cctactaatt tatgttttg tttgctttgt  24600 caaaggtcag ttggctgtaa gtatgtgggt ttctttcttg gttctctatc cccccattgg  24660
```

```
tctctgtacc tatttttata ccagtaccat gctgttttgg tgtctatggc cttctagtat    24720
aaagtcaggt aatgtgattc tgcccaattt gttctttgtg cttagttttg ctttggctct    24780
gtgggttctt ttttgttttc atatgaattt taaaattgtt tttcctaatt ctgtgaagaa    24840
tgatggtggt attttgatgg gaattgcata gtttatcaac ccttggcaaa gtgtttctgc    24900
ttttcttaaa caattttttat tgtctgcttt ctccagtaga tgtgagttct atgagatgag    24960
gaacattgtt tgggtcactg acatgtattg tcagcatacc aaacagtggc tagcacatgg    25020
tgagcactca ataaatattt ggtgaaagtt gcagtgaatg aaaatggttt ctaaaatggc    25080
aatgactata gtcccagcta ctctgaaggc tgaggcagga agattgcctg agtctcaaaa    25140
gtttggggtt gtagtgcact atgattgtgc ctgtgaatag ctgctgcatt gtagcctggt    25200
caacacagtg agaacccatc tcttaaaaaa aatggcaatg aaataatctt atttttactg    25260
cttttctctt taaggctgcc agtgttgtct tttctctgct gatttatcct cattggaaat    25320
tgaagataga taaatatcc attgattatt tataggtgaa attaggcttt tggatccatg     25380
aggaatagct gagacaatct tccaggagct tctggagccg aggaaacatt ggtcactaaa    25440
ataccattta tattggcaac tgtactcttt tccgatgcta gtgtttcaat tacattgtgc    25500
atttaaaagg ctgttgcggc tacctcaaaa tataaacatg atgtgcgaca ctacttgtta    25560
gttttgaaca actgatttat aaatagactt agggtgctca agcctcctgc aagatgagca    25620
ctgcctgtgt tcttccttct gcttccttta tttcagctgt gtgtctacca acttcctcct    25680
ccttctacac taggagaaat tgcactgttt ccaatatctt taacatctgc tatcatgatg    25740
agaaaatatc ttttctggat ttgaaatacc ttcttcattc tttttttta aatggcggaa    25800 ataaattcat agtgttttga gtgcagtttt cttcctgctg ttattgctgg ctcaaaatcc    25860
aggagcattt cagtgttatt tctgagctcc atgatgggag ttccatttct gttttattca    25920
aagtgttatc tccagtgtct agcacagtgc ctggcacatt ataagcctat aatgtttatc    25980
tagtggatgt agaccaatac tattaaagaa ttatcattgc aaagatttag tggcatgaaa    26040
aaatgataat gattaatgct ctactccatg ctaaggaaat gaagtgcaaa tcgttcttta    26100 ttttctcttcc aagtatagag aacttttctga aattaaagaa gcattgatta ataagtttta    26160
atatatgtta ttgatcataa taatatgtaa tcatataacc aaataagata acacaggcca    26220
tcttttgttc tttaaaaaat gacaggaaga ttagaataag agaaaaaatt agaggtcaaa    26280
acagttttct tcaaaccagt agtgtaactt actgagatat cttctgtaat ccttaaattc    26340
tgtattgatg ctaccaagat gcaactcttg agctacaact gcctcttgat aaaggatgct    26400
ggtccctgct gccagtgtaa tgtttgctca tttacagtgg aatgtacaat atagtacctg    26460
ggatggtgaa gaaggtgaag caacaaattt aaaatagctg tgggtaaacc tacagaaaca    26520
gactattctc tttcttccag attgcattat tcattttcat atgcctgcct ttatctgctt    26580
tggaagccta tttcctaatc ttccaagatt tatcatcacc ttcatatgtc catagcatgc    26640
atttctcaga caggtaagat agaattggta tatatttggt atagcaaaaa gtcaaggttg    26700
tctttagatt atatccttgg ttttcatgt ggtactgggg agaaagccta ctgtttcttc     26760
atctataaaa tgaaggacct gggcaagata acattctgtg aaatttcact gaactttgag    26820
ctcagcaaag tagggatgcg tgtgtgtgtg tctatttgca atgcatcaca gaccttaaat    26880
aaatacagtt gacccttgaa taacatggag gttaagagca ccaaccccct gcactgtcaa    26940
aaatccacat gtaattttg actccccaaa aacttaacta ctaatagcct gctgttgtct    27000
ggaggccctg ctgataacac acacagttga ctaacacata ttttctatga tatgtattgt    27060
```

```
gtactatatt cttacaataa actaagctag agaaaagaaa ctgttattaa gaaaatcgta    27120
aggtaaagaa aatatattta ctatttatta aatggaagta gatcatcata aagatcttca    27180
tcctttgttg tcttcacctt gagtatgctg aagaagagga ggaaaaggat gggttggtct    27240
tgctgttcca ggggtggcag aagtggaaga aaattcacat ataagcagtc catgcagttc    27300
aaacctgtat tttaaggtca acggtatttg ttacattgca ttttgtaagt gaccttgtta    27360
atttttttca atgaaaaaaa tagtgttcca ttcaaatgcc tgtatgttta tgagaaacat    27420
ttcagaacta tgaaagttga attcaaggtt tcttgcagat tgtttgtata ctttctgtaa    27480
tgtttgtcat ataatgagaa tactaatggt cttacaactt gaaactgatt aactgattaa    27540
ctctttaagc aacttaaaaa gaaaatcttt cagtgaggaa agagtattca tcagaagtat    27600
tctagtagat gacatatttt tggtaatgaa attgatatgg gcaattaaca gcttttttcca    27660 agttggctat gctgctactc tcttattata caatgatact attttttcaga gcagaaagca    27720 aattagtttt atttttataa accaaatttt aaatatccct ttagagaata gaaaatatga    27780 aaaagtatt gcttctcaga cctctcaaca atataaattt tcttcttaag aggaaattta    27840
ttcttgcatg ccaacacaaa ggataaaaag tttacctatc cttagtttct aagaggaaaa    27900
tgtgcataaa atttccatct gctgtgtgcc agttaccaaa acgataagtt ccaactcaat    27960
cttggttggg tgtggtggct cacgcctgtg atcccggcac tttgggaggc cgaggtgggc    28020
agatcacgag ctcaggagtt tgagaccagc ctggccaata tggtgaaaac ccgtctctac    28080
taaaaataca aaaaaaaaaa aaaacaaaac tagcccggca tggtggtgtg ctcccgtagt    28140
cccagctact tgggaggctg aggcaggaga tcgattgaa cccaggaggt ggaggttgca    28200
gtgagccaag attgcaccac tgcactccag cctgggcaaa agaggagac tctctctcaa    28260 acaaacaaaa aagactcaat cttactaaaa aactgcagag aagaatgagt cattttagtc    28320
aataaaggaa ataagaaat tctagttttg aaaatgacat aatttgctac aagaatgcaa    28380
aggtgatgac atgaggaaaa aaggggtttg ctgatttgtt ttctctacta ctcagcaaat    28440
gcaggccagg aacccatta ttcaaatatt tattacatgg taaattaaaa catttataaa    28500
attaggctca tattcttaga attcctgtta acaaagtgac atataaacaa gattataatc    28560
taatggagat taatattggt tgagaaaaat ctttgagactt ctttaagact tcagtttaat    28620
aaaatattga cttaggtaga tatatgtgag gaaatatata ttttacccat gcatgcaaaa    28680
atgatgtatg tatttcttaa aagagtaggt agcaatgact tcaaaggacc atagctgtcc    28740
ctatcaacat atatattaac aaaacaatta gaaacatgag cttagtatgc taattatatt    28800
tctacccaaa gcctcaattt gttctatagc tatactgttc atatataagt aaaatttag    28860 gggtatcaga gagagttaga aaagagcaaa tacatgtatg aatttgataa gcctatccct    28920
taatttgata gatcttaaaa gatattttat cactgcattc ttctaaagaa atgtatttgt    28980
acattgcaaa acaacccttt ttgagaagta gactatgatc acagattttc ttgccactag    29040
tatttcctaa gatttatttg gaatagaaga tcgatatttt tctgggatga catatggtta    29100
aaaagtaaaa aacaaacaa aacaaaaaac tctttaaaaa cacaacaagt aaaaagctga    29160
atgaattgga aaattaacga atcttcttag atctgtcaga aaaatgagat tatagggcaa    29220
accactgcat caaatattag agaagcagac aggtagatag aaagaatcac aacttagtgg    29280
ggcaaaaacc tacaaggaaa attttttgtgg gaaccggtgc caggtaggaa aacatgaact    29340
gtaattgaaa aattgttcag tgtgggcggt tgttcagtgt ggcaagtctg agggttaaaa    29400
```

```
actccaggag gactcactta cggaagggcc tgtactttg tgagtttaac ctccaggagt    29460
gttcacagtg actactggag aaaattccct aagggagaa gaaaaggaac catcttgaaa    29520
tatgtcagag cattttgttg gactcaagcc tgctctcaag tgaaactatt ttaccagagc    29580
ctaaactttt gggattttat aagagtgtaa cctcccaaag ggaagggaaa tacctaagtt    29640 cagcccctt ttagctttcc acatagggaa aggaaaatat ataactctgg acaactcaaa    29700
ccatcctgtc cacgttaggg ggcctagggg aactgagaaa actggtgaag ttcatagtcc    29760
atgggtacag tttcaccaaa gagggagacc aaattataag gctacagaat gcttcccttt    29820
cccacacctt ttactatcat attactaaaa gcctatttgc agcagtttct tttactgagt    29880
atatcatgtc tgtcattcaa ccaaaaaatt ataaggcatg ctaaaaggca ggaaatgcag    29940
tttgaagaca ctgaataagc atcagaagca gagtcaaata tggcagtgac attggaatta    30000
tcagaccaga aactttataa aaactatgg ttaatatggt gagggattaa aaaaatgaca    30060
tacaagaaca gatggataat gtaaatatag agacggaaat tttaggaaag aaccaaagag    30120 aaaatgccaag tatcaagcat agtgtacaga atgattaaa atgtctttga taggctcata    30180
agtagattga acatagccga ggaaaaaatc tttgaagtta aggatatgat aataggaact    30240
tcaaaactaa aatgcaaaga gaaaaagac tgtgaaaaaa acagaagaga ttattcaaga    30300
actgcaggag aactacaaaa ggtataatgt acgtgcaatg ggcatactag aaaaagaaag    30360
aaaggattag atgcaatatt tgaagaaata gtgtgtgaaa atctccccca attaatgtca    30420
gacaccaaac tacttctcca gagagctcaa agaacaccaa gcaggataaa tgtcccaaaa    30480
ctactcatgg gcatattata ttcaaacttc agaaaatcaa agattaaaaa aatatcgaaa    30540
gaatccagaa ggaaaaaaca cctatagagg agcaaaaata ataaattta tctgacatat    30600 cctcataaac catacaaata agagagtaga gtgagacatt taagatgttg aaagaaaaat    30660
ccggcagtgt acgattctgg accttgcaaa attgtccttc agaagttaag aaataaagtc    30720
tgtcttaaag aaacaaaaat ttcaggaatt tgttgccagt ggaccaccct tgcaaaaaat    30780
gtttaaagtt ctttagagag aggtaaaatg atacaggtta gaaactcaga tccacataag    30840
gaaaataaaa ttagggatat agtagtattc cccaacttga taaagaaaat acacaaaaaa    30900
cctacagttt acatcatact taattttag aaactcaaag ctttcctgct aagatcaaga    30960
acaagacaaa ggtgtctcct cttaccactt tgtttcctac tggaagtgct acctaatgca    31020
ataagacaaa ggaaagaaaa tgaaaagcat acagattccg gaggaagaaa tcaaactgtc    31080
tttgttcacg gatgacagtt gtttatatgg aatatccaaa ggatcagaaa aagaaaact    31140 ggaactaata aatgattatt gtaaggttac agaatacaaa cttaatataa agaaagccaa    31200
tcactttcct gtataccagc aataaacaag tgtaatttga attaaaaaca cattaccatt    31260
tacattagca ccccaagaaa tgaaatactt ttgtataaat ctaacagaat atgtacatga    31320
tctatatgaa gaaactaca aaagtgtaat gaaaaatacc agtgaactaa ataatgaaga    31380
gatgttacat gttcattgtc aagatgtcag ttcttcccaa cttgatctat agattcagtg    31440
caatgccatt aaaaaacaca gcacgatatt ttatggatat caacaaaagg attctaaagt    31500
ttatatggag aggcaaaaga gcagaatagc caactcagta tttgaggaga caacaaagt    31560 cagaggactg acactacctg gctttaaagc ttactataaa gctcagataa tcaatgtagt    31620
gggtactggt gaaagaatat tcaaatagac caatggaata gaataaagag cccaaacaaa    31680
cccatgtaaa tataatcaaa tgatctttga caagggagca aaggcaatac aatggagcaa    31740
agatggtctt ttcaacaaat aatgctggaa aaactacaca ttaacataca acaacaaaaa    31800
```

```
tttttttaaat ccaaattgag tgtaaacaca gatcttatac cctttgcaaa aattaacttg    31860
aatcatagac ctaaatgtaa aatgcagaac tataaaactc ccagaagata acacaggaaa    31920
aatcctagat gactttggta tggcagtggc attttttaga tacagctcca aaggcacgat    31980
acatgaagga aatgattgac aagctggact taactaaaat ttaaaacttc tgctctgtga    32040
aagacaatat taagagaatg agaagacaag ccacagatgg aaaaattatt tgcaaaagat    32100
acttctcata aaggactatt gttcacaatg tgcaaacaac tcttacaact caacagtttg    32160
aaaatgaaca actcaactta aaaaatgagc aaaaaacctg aacagacaac tcaccaaaga    32220
agatacacaa gtgtcaagaa agcataggaa aagatgttaa acatcatagt cattagggta    32280
ttgaaaatta aaacaacaat gagataccgc tacatacctg ttagaatggc tgaagtcaga    32340
acactgatga aaccaagtgc tggtgagaat gtggagcaac aggaaccttc attcattgct    32400
ggtaagaatt caaatggca tagtcacttt ggaagacagt ttggcagttt cttacaaaat    32460
aaacatactc ttcccatatg attcagcaat agcgctcctt ggtatggact tgaaaactta    32520
tgtcctggcc gggcacagta gctcacgcct gtaattgcag cactttggga ggcccaggca    32580
ggtggatcat ttgaggtcag gagttcaaga ccagcctggt gaaatcccat ggtgaaaccc    32640
cagctctact aaagatacaa aaaagtagct gggtgtggca gtgtgcgcct gtaatctcag    32700
ctactaggga ggctgaggca ggagaatcac ttgagcccag gaggcggagg ttgcagtgag    32760
ctgagatcat gccattgcac tccagcctga gtgacagagc aaaactccat ctcaaaaaaa    32820
aaagcaaaaa caaaacaaa caaacaaaac ttatctccac ataaaaacct gcacacattg    32880
tttaacagct ttacataatt gccaaaactt gggtgcaatc aagatatcct ttaatatttg    32940
agtggataaa ctgtggtaca tccagatgta agaatattat tcagcactaa gaaatgagct    33000
atcacatcat aaaacgacat ggatgaaact taatgcata ttataaagtg aaagaagcta    33060
atccgaaaag gctaaatact gtatgattcc aactatatga cattccggaa aagccaaaat    33120
tatggagaca gtaaaagag cagtgttttc cagagggagg aatgtatagg caaattttta    33180
gtgcagtgaa atgaatctat gtaatactat agtggtggat ccatgtcatt atacatttgt    33240
ccaaacacgt aggatgtaac caccaatagt gaaccctaat gtaaactatg gggtttgggt    33300
atcaaaatgc atcaatgtag gtttatcagt tgtaacaaat ataccactct ggtatgggat    33360
gttgataatg gggaaggttg tgggtctgtg ggacagggg tatatgggaa ctttctactg    33420
ttttactgtg aatcaatttt actgtaaagt ttattaatgt taaaaaattt aatgcacatg    33480
taccctaaaa cttaaagtat aataataata aaataaattt aggcaatctg aaaaaatgtt    33540
aataaaaaag aaaataaact agttgaatgt atcagttcat tttcatactg ctataaagta    33600
ctgcctgaga ctgagtaatt tataaaggaa agagatttaa ttgactcaca gtttagcatg    33660
gctggggagg tctcaggaaa cttaacagtc atggcaggtg acttcacaaa gtggcaggaa    33720
ggagaaatga acgcagaagc aactaccaaa cacttataaa accatcagat ctcatgaaga    33780
ctcactccct atgatgagaa cagcatgggg gcaactgccc ccatgatcca attacttcca    33840
cctggtctct gccttgacac atgggtatta tggagattat ggggattata attcaagatg    33900
agatttgggt ggggacacaa agcctaacca tatcagtgat aaaactatgt cttttctttt    33960
atggggtgct atagtgtttc atttcaagtt gtcttttga cctccatttt ccaatttctg    34020
gttaggaaaa ataactttgt ctcctcctta attgacccac aaccttgttt gcaatgaaga    34080
atcaacacaa atctttcatt aaaagaaata ggggaggtga tggggatat ccatgagtgt    34140
```

```
ccatgggcat aattcagttg ccttcattca atgccaatga tactgcaaag cctacaaggc    34200
aaattcatgt acctacagac agactccatc cttttttctca aactattcaa gataaaaaat    34260
cttgtttcat tttatgtgag gattttttttc accatctatc ctcaaaaaat gaaaaatatc    34320
ctcttcattt gggaaatgag tgcttataat agaaagtaat ttgtagtcag ctgttacact    34380
tagatgattt gtgtcacctc tgacctgctt tctgataatg catgacttca ttcatggctc    34440
tctaggtgac ctgtgtaccc tgacctggca taaaccacta gagtattaag tcatttcagt    34500
ggcacatgtt tgagggaaga ttgacatccc actggaagac tatctacagt gagatcctct    34560
aaagcagctg cattcctagt gaggcatgat taagtttatc ccactattag gttctggagt    34620
attacttgtc atgcccaaga ggaaagtttt tctagcatgc agagtatctg gtttttaatg    34680
gctactgagc tgaaataaaa tgtgcctact aagggttgtt catttgtctg tctcccttct    34740
ttcactgttt ttttttcttgg aggttacagt agttatgcct ttctggtcag ctggctgttg    34800
acctatcata gaaatgacac tttcacatct tcaagtgtaa ggaattagat gttccagcct    34860
tcactttgtt tctcatccaa aatcaatgac aaaactttca gtattgattt ctcatggcct    34920
atgaacctga gtcaacttgg cataaaggac ttttcagaca agcttctcta aatgcagagt    34980
cagtggcttc ttttttgccaa actccacttt gctcagtgat aacattaaaa tggtgatttg    35040
attcattcct agtctaaaaa tacttcctca tattccaaaa tctcagtcat taatacatgg    35100
aggaaaatac aaattattac atgcctgtgc ttctcggctg ttgtagatag ataaaatata    35160
tacaattgtg ttctataatt attgagttct tttaagtttt atctttttttt gttttaccag    35220 gaagcaaaat tatgtttatt tcagagctta tttactgcat ttagaatctc atgacactta    35280
aaaaaccttt ctaaaacgta aatattctcc atgatctcca tggtcacaaa cagtatttca    35340
cgttctaatt gatattgcca ttttatcatt tttttttttt tcttggagac agtctcactc    35400
tgttgcccag gctgggatgc agaagcacga tcttgcctca ctgcaacctc cacctcctga    35460
gttcaagcga ttctcctgcc tcagcctgcc gggtagctag aattacaggc atgtgccacc    35520
acacctggct aattctgtat ttttagtaga gacagggttt cacgatgttg gccagactgg    35580
tcttgaactc ctgaccttcag gtgatccacc caccgcagcc tcccaaagtg ctggaattac    35640
aggcgtgagg cactgcatct ggccctttta tctttctttt aactcaaatc ctcaaatata    35700
tccctccatg tgaagttgcc ttccctaatt atgtactgtc ctagtttaat cttcattcct    35760
tgtttgcctc tataaaacca agtttaaaaa tagtctctga ttctgtaaat catcactctt    35820
atgctcattt atatttctat ctagaatatt ttaaatcctt tgtaacaaag tttctactat    35880
gcagtctacc tttctcagct acgatctata tactccttgg ccatgtcttt tgttattgtg    35940
tgtgtttgtc tttgtgtgtg tctgtatagt agtggtttgt aaattctcca tttagtcaca    36000
atatgctttt tgaggatttt cctttttcctg ggaatttctt gatgattttt attttgtcat    36060
gtgatgaaga atgtatgtca aagcaccact gcagaaatag tgcttttcta tttacttgca    36120
ctcttccatc ttagaagagc tggtgataga caaccgactc ttcttttatc ttggtttcta    36180
caacacagag gttgctaagc gactttaatc cctttttaaca caggacaatc aacaacaaat    36240
tccttctttc tttagattca gatatttcac ttagaaaatc tagcaaataa aaaatggttt    36300
aaaacttctt taaaatgtgt aattctgtac aatctcctac atctgtaacc cctgccccaa    36360 atattttttta cttatgctat ttcttgagca ttatgatatg cttattcata ggcaatcaac    36420
ttgtaagtag caatagtgta gccccttcta ggaaatcgaa gatgtgaaaa tccagtttaa    36480
tgtgataatg agttactttg atgaaaaaata ctatgtcaca atttgttata aaaatactca    36540
```

```
tttggatttc tgattcactt atattaccct ccaaccttaa gtatgattga atttatagct   36600
ttttatacta ctttctttat ttagggagga gtgtatttaa attctgttat ctcggttatt   36660
acttgaaagt tcaacctcat actttcattt ttatataatt ttaatattat gaaatatttt   36720
tatgtaattt tatgtataat tcgaaaacat ttttaaatat tgcatcttta aattttatt    36780 tcttttatca aattttccct atcatttgtt ctctggctac aaccaaagtt aatagttaca   36840
ttttttccca gtgacaaatg gtaatttgca aagacttgta acagttgctt aatacttttt   36900
tatcccttat ttaagaatca tgcaaacaac cagagctgat aggcagcagg tgcacatgag   36960
tgtggctgtg ctgatggtta ctgaaagatt tccaaggtag ctagtaattc tgctacccta   37020
agccactata gctccttccc cattactccc tgggtctacc caccatcctg cagctagaat   37080
aataaatggc atgtaggttc ctctaggatc ctcctccagc actatgtctc atgcctggac   37140
atatgagctg ttaaatattt tgattatcac tcctgtgtgg taagggagac gtctacttgt   37200
cgtaacttga tgtttactaa actactttta agattacctt atgataaaag tagacacttg   37260
caattttgca gaatgcatag tttgttttta acaaaccagg taaacataac tgcagagttt   37320
tcctatacgt tttgaaatct ttaaaaaagt attttttatt tgcctttcta ttagaaatag   37380
attagataaa aatttccttg tttcaatttt tagaatgaac attagagaat attgttactg   37440
aaggaatttt tttaaaaata gtgactgatc aaatgtcagc agctttatac tatagtgtaa   37500
aattttattt tgtagtttgc catcccatta agcattagaa tttttataat tgatcctttg   37560
atgtttatat tcatgatatt aatgtaatgt ctttaaacct tagctcatat aggtcatatg   37620
acttaaagca tccttagatg aagatatttg ggctataaat aatttatgac ataagtgatt   37680
taaaaattca ttctttccat ccattttgaa gaaattgtaa ggtagggttc atgtatacct   37740
aatacttatc cccccaaaat acgaaaaata aaatcatttt taaatatct gggttaatgc    37800 tatagattgg aagcagtttt taaaaagcac ttaaagtcta ccagtttatt gatcctcaat    37860
ctgtggctgt tttaaatgga tgcaattagc agttcagtct aagagaacca tggtagtaga    37920
ctcattactc cccagaaacc attacatcat ттттgтaatат taattacta aatataagga    37980 atagaatata tattgtaaaa attgctttgg aatcaataat aagтaтттgтg gctatcaatt    38040 atagttatat atacaatgt aagggatatc cttttataaa cttaatatca cacaagtaga    38100
cttagaataa ttccattaat ataattttgc ttgtgttttt atacctatt atttcaataa     38160 ctcттттттcc tatatatt tttatctca aattcgatag tatctaaatc atggaatcat     38220
aaaaccttaa agctgggttg gaacagaaat aатacaатттт aacatcttat aggctctcta    38280
gtcctcagtt tcctaagtg atcggctcaa gatcatgaat ttatggagga ttagagtcag    38340
aattagaacc caagattaat ttatactttg ttatctcttc tacagcctac ccccttagtt    38400
tgcctgtggg tttatggaag ttacaggaga gacattctga gattcagcta aaaacctagc    38460

tcccaataga attattgccc tgtagtcagc cgcgcaaata caatcacaaa tacctgaagt     38520

tccttgtgtg aagaaaaaga aatgactat taaagcatca aaatcaatgc aagttacctt    38580

tctttgcccc tttcttcccc tttcactcct tcttctcct atactactt aaatttctag     38640 cggggatctc taaaatgcct ggatgttagg aatggtaagt ctattgtaga gaattatat     38700

тттcтаттття gtggatgaaa aataaaccat acccttaaga ggcтттттcaa agttaagatt    38760

ttgagcacat ccttcattgg cccagtctct gaccagtgag gtcaagtatt agccagtgtc    38820
agaatgtcgt gaaaagtttg tgtttcagat gcagaattt tttttgcatt tctgtgtga      38880
```

-continued

| | | | |
|---|---|---|---|
| tgtttatagg | gtattttctt | ctgaaatgtt | ttccatcttg gtttttaaaa atatctatta | 38940 |
| ttttaaaaaa | tattccctca | taacttcttt | ttattttcgg aaactatata aattgatctg | 39000 |
| ataatctata | cacaatgcct | tgtgaattta | tacctgtacc tctcatgttc cagtgtttgg | 39060 |
| ttcttaaata | atcactttgt | ataatggaaa | tactatgtta aattgtttat aactggtggt | 39120 |
| tgatatttca | gccttgtttg | gctatcgtag | ttatataaag actgttaatt agaaacaacc | 39180 |
| tcatatggtg | tatgcttgtt | tttatcttca | tggaatttgt tctgcaaaca ctgagttctt | 39240 |
| tactgggagt | caccactttg | tctatgttag | gaggagcagg aagtgaatac atttaaggtc | 39300 |
| tttaattttc | ttcttaaaac | tttgactact | gtagtggttt tttaaagcat taacaggaga | 39360 |
| atagccatca | ctgccaagta | gctgacattc | tgaaatagca cttcccttta ggcactgtac | 39420 |
| agttggaatc | atttacttgc | agagaggtgt | gtgtgtgtgt gtgtgtattt atgtgtgtac | 39480 |
| tcatgtgtat | aagaatagga | gaaacactt | gtgggcatat cctgctgagg tgagtaacgt | 39540 |
| gctgattagt | gaactccagt | ctcatcccat | ttaaacctgg aggagaacca catcaagcac | 39600 |
| agaagcagcc | aaagcagcat | ttcaacagga | aggaaacatc tattactggg gctttgaaga | 39660 |
| aacatgccat | gaaggtgtac | taatatcaca | aagggaaggg aaggactaaa ttcagcatga | 39720 |
| taaacaaagt | ccctttttg | taacggaagt | gtttgatgat gtttgatcaa tggtggatct | 39780 |
| atctcttgaa | aggaaaatgc | atttaaaccc | caaatggagg attcttatat aaggtgccta | 39840 |
| gcttgtaatg | atatattcat | gtttataggt | agagtgactg gtttttagag aagaggtttt | 39900 |
| tttttttcct | tcatttttga | acgaaaactt | gtctgtctct aggctttgaa atgtagaatt | 39960 |
| atttacctt | ccccaaaatg | aaatgtttca | ctgaatctcc tacaagcttg tggaggccat | 40020 |
| gaagcatgtt | gaataagagc | acaggctctg | gaggccctgc cacccacaaa gggtgtgcta | 40080 |
| aggtaaacaa | ctgatagtat | tttgaaaatt | agatgactta gaatccattc aataaatttt | 40140 |
| agctattttt | attgtctttt | ttttctaaat | ctatttggaa aatattgcag ataaagtaga | 40200 |
| taataccttt | ctaaaacaca | gtgagaccag | gcgcagtggc tcatgcctgt aatcccagca | 40260 |
| ctttcggagg | ccgaggtatg | cggatcacga | ggtcaggaga tcgagaccat cctggctaac | 40320 |
| acggtgaaat | cccgtctcta | ctaaaaatac | aaaaattagc caggcgtggg ggcatgcgcc | 40380 |
| tgtaatccca | gctactcagg | aggctgaggc | aggagaatgg cgtgaaccgg ggaggcggag | 40440 |
| cttgcagtga | gccaagatcg | caccactgca | ctccagcctg ggctacagag caagactctg | 40500 |
| tctctaaaaa | ataaaaaata | aaaatagaac | agtgaatagt ttataaagat aaaatagaat | 40560 |
| aggcttcaat | ttagggaaca | aaggaaaata | tgtttaggaa tgatattatg ctcaaaatga | 40620 |
| ttgcaacttt | gatggtgaag | tgtattttat | tcaattaaaa atgtagatat ggctgggcgt | 40680 |
| ggtggctcac | acctgtaatc | ccagcacttt | ggaaggttga gcaggtgga tcacttgagg | 40740 |
| ttaggagttt | gagacctgcc | tgggcaacat | agtgagacct catctctaca aaaataaac | 40800 |
| aaaaaatgtg | ctgggtgtgg | tggtacatgc | ctgtagtcct agccacttgg gagactgaga | 40860 |
| tggaaggata | gcttgagtct | gggaggtcag | tgctgcagtg agccgagatc gtgccactgc | 40920 |
| acttgagcct | gggtgacaga | gcaagaccct | gtctcaagaa aacaaacaaa aaacaaaaa | 40980 |
| caacagtaga | tatgtgtgtg | ggaatgagaa | catttaaatg tgctcatcgg cttagatttt | 41040 |
| tctttaaccc | ccttcatggc | ccttatctta | acctctgtct tcagcactac ccttcatatg | 41100 |
| tttgttccgt | tttatcttct | aagtgatttt | tttataactc tcaatgtatc atggcagaag | 41160 |
| gaaaactcag | tgtataagct | gactgtattt | tgcatttct tttttttttt tttttttttg | 41220 |
| agatggagtc | tcactctgtc | acccaggctg | gagtgcagtg gtgcgatctc agcttattgc | 41280 |

```
aacctccgcc tcctggaggc gattctcccg cctcagcctc cccagtagct gggactacag    41340
gcttgcacca ccatgcctgg ataattttta tattttagt agagacgggg tttcatcatg    41400
ttgtctaggc aggtctcaaa ctcctgacct caagtgatcc acccaccttg gcctcccaaa    41460
gtgctgggat tgcaggcatg agccaccgcg gcctggcttc atgatccaaa atagcatcat    41520
taagcttctc tttcaaaaca tgtatataag cctgtgagtc atcactgtat ttatcagaat    41580
attatcatat tggagacttt gcaaagctga acaaagccag aattattggc tactgaggaa    41640
ctatattcta gcaagagact attctatttg ttggggatca cctctttta ctaaagggga    41700 ctgttttggg catataaaac tagaattcat ggtttctcct tgatagtttg ccagcttgat    41760
tcccagtcaa ccagataact gctggtagtg acactcatgt cctccaggac tcccaatctt    41820
gtgccagctc agagagggaa atcccctag aactgctcac accattccaa gaaccacaag    41880
caccaccttg gtatagttaa aaatgtgata ccaactcaaa ttctgataaa aacaagttct    41940
ataaagctta ataagttat attttttact ttttaagttt tgtttacta ttttaaacag    42000 aaaacagaag gtaaaaactc ctctgccttc ctcagtattt ggtttgtcag ttgctgaact    42060
cagatttaag agtctaatca tatacaggca ataaccctct tctaatctta ataatgtttc    42120
tttgatcatt tctttaaaaa gaaaaatgaa atagccttat gactccaacc ctgacctcct    42180
gtacttcacc tgcctgatga atatttattt ggaatacata agttttttca aatgcatcat    42240
gtcaagaatt tgtcatttca gattcctttc tagaattatc tatttatctc attagtagca    42300
tcattctttc agacaaccaa actcaaaagc tttatcacta taattgaatt tcttttttct    42360
tcttacattt aaaatgttac taaatgccat tcatttcttt atcagtaata tttctgtttg    42420
atcattttat ttcatttatt ctgccaccct ctcattccaa ctattgctta tacttgagta    42480
ctgcaataag ccaatatctt gcatatgatt atttataaca cctaaatctt ctaccacttc    42540
acactcactg ggatggatat aattttaaa acatacaata acaggtgtta gtgcggatat    42600
ggaaaaattg gaaccctgac acattgctag tggaatgtaa aaaggtgcag ccactttgca    42660
aaacagtttg gcagttcatc aaaagattaa gcatggaact accataagac ccagtagttt    42720
cgctcttagg gattccactc tcaagagaat tgaaaacata tgcccataca aaaacttata    42780
aacattgtat atccatgttt gttgcagcat tattcacaat agcctaaagg tagaagcaac    42840
ccaaatgcct acagatggat gaatggataa acagaatgtg gtatagacat acaatggact    42900
attattcaac cttaaagagg aagaaaattc tgacacatgc tagaaaataa atggatcttg    42960
tatacattct actaagtgga ataagccaat cacacaaaga aaaatattat gattccactt    43020
acatgaggta cttagaatag tcaaattaat agaggcatac agtagaataa tgattgccag    43080
gggctgggag gaggagcaaa tgggaagtta ttgtttaatg agtatagaat ttctgtttag    43140
gaagatgaaa aagttctgga gatgggtggc agtgatggtt gcacagcaat gtgaatgtac    43200
ttaatgccac agaatagtat acttaaatat ggtttgaatg gcaaactttg ttacatacat    43260
tttatcacaa ttaaaaagtt tgaaatgaat atccaaagaa gcattattta tgaggctaaa    43320
agtggaagta acccaaaagt tcatcattga tagctaaagg aaacatggca tatcaaaaca    43380
gtagaatatt agtcatacaa aggaataaag tacagacaca tgctgcaata cagatgcacc    43440
ttaaaaacat tacactaagt gaaagaaacc agacgtaaaa ggccaaattt tgtatggttt    43500
tatatatata aagtcgttca aaataggaaa acccataaag actgaaagtt gattagtggt    43560
caccaaggcc cgggggagga atgaatgaaa actggctcct aatgggtact gggttttttg    43620
```

```
gggcgagggg gacagagtga tgaaaatatt gtagaatttg atagtaatga taggtgagag    43680
tggcataatt ttttttaata tactaaaacc cactgactca tatactttac aaggatgtat    43740
tttatggtat gtgaattata tctcaaaaca ccccttaaat tttaacgtat ggcttttatg    43800
atgccatgtt tctaaagaag caacgtgtcc cagtctcagc ttactatttc taggcatgtg    43860
actttgagaa aaaattaaga gacctccctt cttactctgt aaaatgggaa taataataat    43920
gatgataatg ataataataa tgatcttacc agattttttt gagtgttaaa tgaggtaaca    43980
tatgtagtgc atctagcata gtgtctggca tttaccaaga accccgggaa cctgagcttc    44040
aactgcttct gatactattc cagatactat ttcaggatat tccaatactg tttccatata    44100
ttcaggacaa tggaccaact cctttagcca ttttatcaaa actctttaga ttctgtttca    44160
aatcggtctt tccaaagtct tcttgtgctc ctttgtagac actcttcagt cagagagagc    44220 ttttttaatct cctccaattt gctgcagctg tatctgtgcc tcaaaacaac gctttctccc    44280
cattcctctt ttctctctgc ccttggaact ctgtggactt ctctcatgtt tttaacctac    44340
tcccttttat cagtgcatgt catctccact tatttgtagc acccaatatt tttactacat    44400
ctttgaccaa ttaagtctta cttgggttat gttttttaaag taggtatctt attaggtggt    44460 cctttttaaag tatatgtcca gtctctccag ctaaattaaa acccttgagc acagagacca    44520
catgttataa tgttttacct tttccatagc acttagcatg ttaccttgac atggcatata    44580
ctgaatgaat gcttgctatt tatgagttta gttagtgcca catctcatga agtacaggga    44640
cttaatgatt ctcaatcctg acttcatctt acagtcacct ggagaataaa gtttcctctt    44700
agctcaacaa gtcagaatct ctgagcaaaa tcctcaactt cttacctagg tgatactctt    44760
gtaagccaca ctgtgaacca ctggattcaa cagatgaagt aatataagcc actggctctt    44820
aagcctcatt gattattgcg gtgaagatgt gaagactaaa gatgctttgg gcatggcaaa    44880
gtgttctaca gatattagaa ttgttattat ggtacatttg agagtgtcat tgctttgaga    44940
aagattctct aagttttta acagccacac tgtaatggaa atatccaatt ataggtatcc    45000
aaaacctttt aaactcttta tatcaggtgt atatacctg ttccttttg ctaacttaaa    45060 aatgttcaaa ctctgtcttc tctaggctgg caaacattca gcagcacacc ctctcaagat    45120
tgtttacttg cctttgctcc tgttgagtta caacgcttgg aagcaggaga tgggctcagc    45180
agcagccaat aggacatgat ccaggaagag cagtaaggga ctgagctgct ggtaagacag    45240
tggagacagt tgacacttgt ttgtcaagta tgaatttatt cctaatgtaa tggtaatctc    45300
tctcccaaac ttcaacttca agttaccctg caccctctca aatactttc tttattgtct    45360 atgcttagga cacatggatt agattgttaa gatttgtgaa tttactaaag ttgtgtactg    45420
acttatgtat agctgtattt ttctggagaa agatagattt ttatcaattc tcaatgtcta    45480
tggagttttt aaaaagaggt aaggattatt caaatgtaac tataaacata agaaaatgtg    45540
atatctataa ccagttgtta gagtatttat cgcctccatt ttgcttcact tgtagccact    45600
tcgtctcaat cttgttaagg accaaataaa tggtatttgt ggttacttgc tgatctgaaa    45660
agtgagtacc tcctgcacct ggctagtcag tcttgtgaca atttggtgcc atagaactag    45720
cagagaacta aattatggaa tgcagatct caggagcagc tatgtgattt tacatacggt    45780 ttgttttaa tggatagaga cagagtctgg ctatgttgcc caggctgctc tgaaactcct    45840
gggttcaagc catcatcctg ccttagcctc ttaaggagct gggattacag gtgcatgccc    45900
ccaggcccag ttcatatgat tttctgaaaa tacaaaagaa agagggagat acaaaatact    45960
tttttaatca tgttcttata attatcttaa taaaaatcaa tttgctctga atgccatgac    46020
```

```
ctgctgagtg tcccaaccta agggttgtca gaccattttc tcatatatgc atgtatagaa    46080
gtagggaact aatatatttt tgtctaaaat gtttaagatg aagatgagaa tgaattctac    46140
aatatataat tttgcctgaa ctatataaga cagttaaaat tatagagaca ttgcaggaga    46200
gactctggat tagatagaaa aaaggaagaa ttaggctttt tttttgtcta taatcctttt    46260
agtaggtaat tcagcttcag tttcactaaa tcttgtttat gcattcagca taacaaatct    46320
tctaataagc ctgtatagct ctaatctctg ccttactgca gacacctgag gatataagta    46380
tccactctgc cacttgatac ttctcagaga ctgttctggt gctgagaaat cctttccagt    46440
gtgtcctcag ttgaactccc atgattcctg gatgttgcca ttttcaagac acagggcaag    46500
cgcatctgtc tagattacct ctctaccttg ggaattttaa gtcactctgt gagggaaaga    46560
gaactcagta tagtagtaac tctcagaatg aaaattttcc ccttgcatgt taatattttt    46620
agagtaatca ttgtcactga aaatagactt cctctttccc ctctcatgct ggaaaatctt    46680
aggtaattat gaataaagca ttctttactt ttcccctcct cccttgatga ttgctttacc    46740
tcactctgtg agaactgtga ctactcattc tgctcttgtc ttttacatga gaactgagag    46800
cgcattttta agatggaatt ttcctcctta atgaagtcat aacattagtc agaagatttt    46860
ctcttcttga acgttaagcc tgggtaagga ataaagtgca gaagtttatg gaaaattata    46920
agataactta aaaaaaaaac gaagacaaca aattaaaata ttagccattg agggaaaagg    46980
ttttacaggt agctctctga ggagttcttc cctcatatct cctcaaaaat cttgttttgc    47040 attttaatttt ttacagttgg ataagctcag cccttgacat attttcaata gcaaataagc    47100
ctagagttta tttttagtac atttattagg aatgtgttct tgggaaaatt atttaacctc    47160
tgtaagccct gctttaaatg gcaaagaaga aagtaggtaa taatagataa taacaggatt    47220 atttttatgca ttacctgtac attgcccaac atatagtaag ttctcaatttt tatattggta    47280 tttgttttat tattaaccac ttttattaat gttgctttta gttttttgaaa tatgaattca    47340 ttcaaaaata tttcttgagc acctgccaaa taccaggcac tcttctagga actagagtgg    47400
cattaatgag taagaggcaa aaatctcttc ccttgttgag cttagaatcc attagagtaa    47460
gagacagaca catacaaaat aaaatgtata atatagtaaa taccaagaag tgctaagttt    47520
taaaaatgta aagcagaaaa aggaaattga gtggcagggt taggtagtaa ttgaagatat    47580
agtagtcaag taaggcagct tcaagagaag attatgtctt aaataaaaat ctgataaaga    47640
tataaaaaca agccatgaag ttatctgaag gaattgcagg tagtggagaa cagccaaaag    47700
acctggagta gtaaaaggtt ttatgcagag tgatttaaaa agaatcacag tatcttatac    47760
atcagtaaat atttacacat acacttaagt aagtgatatg gacaagaact ttggaagttg    47820
aatagcaagg tccatctgga ctataacaga ggaggcttca caaggaagg tgacagggca    47880 tggcctggat cctgaaggac aggaagaatt gggatcgata acaaagaatg acatcccagt    47940
ggagagaagt ggaggggaaa cagcatgaaa tggagtgaaa taagaatgtt ggcctttagg    48000
gcaggaatgg gccaggcaga gggcaagtgg gaagcaggaa aaaggcgacc ttgtataaag    48060
ttcatgttgg caaatagaga gaagatggga aagcagggta aggccaaatt tagtaaaatc    48120
ctaaagtcaa gctaaagatt attgcatgct atcctgaaaa tattgggaaa taattagagc    48180
agatgagtag aaaggtgaat tcttgtattt agctatatca ttatttttac aaatttaaac    48240
aaataaggaa atgaggcag tagttggagt aatttaggag ataaattgaa aatggatttt    48300
gttaagagag aagggaagat agatttttata tattttaagg aaaaatcatg aggatttatt    48360
```

```
tgctgactgc acgtaagaga taaaagagag gagtcaaaga tttctctaaa attttcaaaa   48420
tgattaatta cgtgttggta ttaaaagaaa tagggaagtt gggacatatg agtttgaatt   48480
cagcatgagt cagttaagac aatcagatgc agatattctt aaggcaacta aagttcattt   48540
gatatttgtc ataggctg aattaagttt ctaagagctg ttttactat gcattaaatc   48600
cgtgtaatac taacatagta caaaagttgt ttgctatcca aattttgtat ttttataata   48660
agttggagag acagagaatc aaaaaattat tgatttggaa ccattagaca tcagctagtc   48720
caattagttc attttgtgga aggaaaaagg atacccagag atgttacatg actttatagc   48780
catgcctcta gctagtatct aacttggtct agcccaggtc tccatactga gactctcctc   48840
ctgctaataa aaaataata aaaagtatt agtggtttgt attttgctgg cttgcttgtg   48900
gagaatagga ttagaaggtt tgacttgcct gttagcactc tcttgtagcc attttctaa   48960
ttaacataca cattttaccc tttctcatga aacagatcta acttgtttag aagcttcagt   49020
cttcttgatt taattaatca ctttctccca cctttagtca ttgttgaagt ttcctgattt   49080
acaatgttat ctttttatct tttcagtagt ataaggagga atgatatttc tactgttgta   49140
ctattttct gtttatcttt cagaagaaaa atagcttttc ttattggccc aaaaaaccat   49200
caccctacag gaaataaatc acactctttg cttgattttc ctgatctggc tactgatttc   49260
tcttcaaatt taagccaata cttagacttt aagacttcat tgttacttcc ttacaggtca   49320
ttcttatgaa ctaaaatcca tagtcattgt tctagcaagc ctgagcagtt tattctttga   49380
gtcacaggat tataaaagaa aaaatagacc ttagagatca taatacagtg ctcttcaaac   49440
tgtactcttc aatttttcta ctacttatca gttgttttt attctaataa aatataatta   49500
cctagcaagt gagcagacat gtatttacag tagctttaca attctttata cacttcttta   49560
ctctctccat tacacatgcc acatggtatg atacaagtca taactcaact atgtgaaagc   49620
aaaaccactc ttatacatgg tgtcttgcat atatattaag gcccagagtg gtatcagtag   49680
tctctgtgtc ccaagagact gaattaaaca agactgttga ccttcttgtg gcatttatct   49740
gacaaccttg gcaatcccta aattcacaaa tagctgtata gcatttttg catttaatgc   49800
atatccacat atgatgtgtc ctttgatttt agaacaagta aagcatgcta aaatagactg   49860
caccttatga aagtcatttt cactattctt gtgtttcagt ttcctcatca aaaggtgaaa   49920
tatcagctgc ctctgttgat ctcaggatct tttaagtaga aatggaagag tcttagtgaa   49980
aacagtttgt attctgaaag aaaattgcaa tgtaaataca ggcactaaaa acgtttattc   50040
atctttacag atgttaatct gaccagacat ttttctcaaa atgtgaaaat agtatggatt   50100
ttcttagctc atttaatatt gaaagactag aaaaacaagt aatgatgttc tagaagaatc   50160
tatgatcata taattacagt tgtccttcag tatctgtggg agattggttc caggaccccc   50220
catggatatc aaaatctgtg gatcctcaag tctcttatat aaaatagtgc agtatttgca   50280
catgatttac atataccctc ccatatactt cgaatcatct ctcgattatt tataatacta   50340
caatgtccat gctatgtaag tagttattac actgtattgt ttagggaata gtgacaagaa   50400
aattaatctg tacatgttca ttacaaacac agcaatccat ttttttctg agtattttga   50460
tctgtgattg attgaatcca cagatgctgg aatccatgaa tacccatggg gggctgacta   50520
taatgttgtc tatgtgcgta gcaattttgt aattctcaac caaggacacg tatagtcctt   50580
gaatcttggt aggagtcttg gggactttc ttaaaatatt ttgaccatct tctcaagatc   50640
ttgactccta cccccacttg tacacgtgca catacttgtg cacactcaca cacaataccc   50700
ttccttaagt cctgctcacc agcttgcttc ctattgcatt gagagcattc aacctgtaga   50760
```

```
ccaagaactt ctaccatatt tttccacctc taccccaaaa cacagtttag acatatccat    50820
tcttttcatt cttcagagtc atctcaccac ttccataaat tatttcctaa ttgttccctc    50880
tgcctctgtt cttttttttt tttctgatga tcagttcaaa gtacctctgt atgcccattc    50940
ttaagtgcaa atctgaccat ctatacccct tcttaatatc ctttcttttta tggatacccca   51000 tttcagactt tattaaagga gtggaagctt cccctcccc acctcaccac ttgaagtttt     51060
tgcaattaga atggagttta tttggttaat gcaaaaatag atgtgatgta gaattcttgg    51120
ggacacctac ttatccccctt ttcagagtgg ccctgaatag ctctgtgaac ccaggaatct   51180
gaagaactca gtacagaaaa ccatcagcct acagaaagta gatcaaactc tatgcttgat    51240
attcctgatc tggctcctgg ttactcttca aattcctcct tactatattg tcccttcaga   51300
tttgtaaatc tttaccgtga catcgtattt tacacactga acctttgtac cgctgttcct    51360
ctcctgatga acttcccttt tctcttaact acacagctca gatttctcat aagggaagct    51420
tcatatttgt tgtggcactg ttgttcctca aacatcctac ttactgtagt catttgttta    51480
tgcttgtctc ctttgcagat tctgaaattc ctagggcaaa ggctgcatct tgtcttctta    51540
ttactaatat tttacacagt atctggttac atagtaggca ttcaatcata caatttaaaa    51600
gaagaggttg actttgtgat ctttttcata tgttttattt ccctctcccc ctactggcaa    51660
cttcttccta cttcttaaaa tagatacagc acttgcccac taagtggagg gaagaggtgt    51720
gggagtcgag tagttggaac ttcaagtgtc aaaacatgat aatctcattt gcaaagttac    51780
attatatcgg agcttgaacc tcagagatac ttaattataa gcaacacttg tggaacattt    51840
gatacctaca ttttttcac taaagtatcc tatcaaaatt aaatgtgttg cagttgagat    51900
ttgtgaggtt ttagctattt agagactta gggatatgtt tagtgttcta attctaatag   51960
tattgatgaa tataaatgtt tcactgtaga aagagaagtt tgagagctgt tgtgaatgat    52020
atttgatgtc tattaggtga taatttctga tgactaaaca tgctcaagac cttagtgaga    52080
aatacatgaa tacagaaaat attttgaaaa ttatgagaag tttatcattg attatagatt    52140
ttcttatcca gcagttttttg gttgtgttct gttttttcact gtcagagaag cagaaagtgg    52200
tcagtggact ttagaatgta ggctcttgta ggaggccata tgtttgagag tgctgtccag    52260
gtgctttgtg atgtggctga aatggatgc aggcttgcag ggaaaaacta atactgtaga    52320
tctctagaga gcattttagg aaagacttct aagcttaggg ttccctgacc aaagagtaaa    52380
aagtgattct taatatccat agctatagag gaaagtaaat acacttccca catcaaatgt    52440
agaattaaat atttaggcat ttcaagtgta tttcatttag aacaaaataa aatcatatat    52500
tcactaatga aatataaaac cagatggtct ctgaaaggtt tttcccttta ctcactttca    52560
gagtaaggca aggaagagta gttttgtttt ttaatttata tttaattgt ccctttctgt    52620 ttttccaaaa gttttatttt ttgaaagtga gtcaccttt agacatttga aaattagaa      52680 ttactatgat gtttatttta ttagtaagtc ttcctagagt agcaacgtag aaaagcatct   52740
ctgaatgcct acatagtaag tatttaataa atgttttttg ggccaggtga ggtagctcac    52800
tcctgtaatc ccagcaattt gggaggccga ggcgggtgga tcacctgagg tcaagagttt    52860
gagaccagcc tgaccagtat ggtgaaaccc catctctact aaaaatgcaa aattagctgg    52920
gggtggtggt gcatgcctat aataccagct actcgggagg ctgaggcagg ggaatcgctt    52980
gaactcagga ggtggaggtt gcagtgagcc gagatcgtgc cgttgcactc cagcctgagc    53040
aacaagagtg aaactctgtc tcaataaata aataaataaa taaaatacat aaataaatgc    53100
```

| | |
|---|---|
| tttttgattt aacgaaggtg tcattgtcct atgaaaagga aaactatcaa aatatatttt | 53160 |
| ttaaaactta gcttttgata atgatatgga agatatttct cttaattaac ctaagtcaga | 53220 |
| aactaaaata tgttataaaa tgctaacatc aaatatttga gaccagttaa aggagacaga | 53280 |
| aggaagttat ggagaaagaa gcagtagcca gaaaataagg gcaagaaaat gttttctaaa | 53340 |
| tttatgagaa tcagaatgtt tacaaaattg ctattattat catctggaaa aaatatgcct | 53400 |
| tgtaggctga aaaaatgaac attccctttc cataccatgc aggaaccttc tttactgcat | 53460 |
| tcctaagagg actagtctag cacctaattg gatacttgtg gtaatatttg ggaactcact | 53520 |
| gatctggtac atcagtgtgg gagtcgagta gtcagaactt caagtgtcaa aacatgatag | 53580 |
| tctcatttgc gaagttacac tatattagag cttgaacctc agagatactt aattataatt | 53640 |
| aacacttgca gaacatttga tacttacatt tttttttcac taaagtgtcc taccaaaatt | 53700 |
| aaatgtgttg cagttgagag ttgtgaggtt ttagctattg ggaaacttta gggatatgtt | 53760 |
| tagtgttcta attccaatag tattgatgaa cataaatgtt ttactgtaga aagagaagtt | 53820 |
| tgagagcaag ttgagcaaga atctgtcact ctaggtcttc tactctttat taaagaatgt | 53880 |
| tggattcatt tataacttac tggtccctta aatattaaag tttggtgttt ggtatcttaa | 53940 |
| acatgattac atccttatag ggctctcttc taattgcctg gatactgcac atctattaat | 54000 |
| acagtctcaa agcacacttg cttttttgat agtaagagcg tacgatttaa tcacattgaa | 54060 |
| gttagtccgc aaaggttttt gtctttttt caggcaagca gctgatgaat gaatctctac | 54120 |
| tatccttcac tttgtgactg tgattttcta aataaatgtt ggagatttta acttacaatt | 54180 |
| tattaatttc catcttgttt cttcaagtcc ctcctttaag gaaatttatg gaaatctttt | 54240 |
| tccataccat caagtggctt atttcttttt aacttttttc cttaagttca ggagtacacg | 54300 |
| tgcaggtttg ttgcataggc aaccttgggt catgggagtt tgttgtacag gttatttcat | 54360 |
| cacccaggta ttaagcctag tacccattag ttatttttcc tgatcctctc cctcctccca | 54420 |
| ccctccaccc tctgataggc cccggtgtgt gttgttcccc tctgtgtcca tatgtcctca | 54480 |
| tcatttagct cccacttata agtgagaaca tgcagtattt ggttttctgt tcctatgtta | 54540 |
| gtttgctatg gataatggcc tccagctcca tccatgtcca tgcaaaaaac atgatcttat | 54600 |
| tctcttatat ggctgcatgt tattccatgg tgtatatata acacagtttt ttttttatcca | 54660 |
| gtctattatt ggtgggcatt taggttgatt ccatgtcttt gctattgtga ataggactgc | 54720 |
| agtgaaaata tgtgtgcatg tgtctttata atagaataat ttttttttcc tttggtatat | 54780 |
| acccagtagt ggggttgctg ggttaataga tatttctgtc ttgaggtctt tgaggaatcg | 54840 |
| ctacactgtc ttccacaatg gttgaactaa tttacattcc caccaatagc atataagtgt | 54900 |
| tcctttttct ccgcaacctc actaacgtgt tattttttga cttttttaata atagccgtcc | 54960 |
| tgactggtgt gagatggtat ctcattgtgg ttttgatttg catttctcta atgatcagtg | 55020 |
| atgttgagct ttatttcata tgtttgttgg ccgcatgtat gtcttctttt gtaaagtgtc | 55080 |
| tgttcatgtc ctttgcccac tttttcaatg gggatgtttg tttgttgtt tgttttttcct | 55140 |
| gtaaatttaa gatccttata gatgctggat actattgtca gatacataaa ttgcaaaatt | 55200 |
| tttctcccat tctgtaggtt gtctgttttc tctgttgata gtttattttg ctatgaagaa | 55260 |
| tgtctttagt ttaattagat cccatttgtg aattttttgct atgaactgga tctgatataa | 55320 |
| gcatatgttt aattttaact cccaggtcac actgtttttt tttgtttgtt ttgttttttgt | 55380 |
| tttttgttttt gttttgtttt tttgggagat ggagtctcac gctgtcacca gtctggagtg | 55440 |
| tggtgataca atcttggctc attgcaacct ccacattccg ggttcaagca attcttctgc | 55500 |

```
ctcagcctcc tgagtagctg ggactacagg cacacaccac catgcccagc taattttttgt    55560 atttttagta aagatggggt ttcaccatgt tggccaggat ggtctctatc tcttgacttc    55620
atgatctgcc cgcctcagcc tcccaaagtg ctgggattac aggcttgagc caccacacct    55680
ggccccaggt catacttttta atcaaaatga gaaaaaagat tgacttcact ggagtgctta    55740
tgtcttgttt tatattcaag ttttaaattt atgttcttga gattattaca tcttgagtta    55800
cttgataata ccacggttga aatccatgtt gttgaatcct tcaacccctt gaggactgag    55860
aattcccttt aattatctgt ctgaatcatt aaatacttgt aaatcaagag ttcaatttag    55920
aaatgttata cttgatacat tttttaaagc tggataaatt aacctattaa acaaaattat    55980
ctcttcttca aaaaaaggc atcacttccc ccacaaatgt gtaatttagg aattgttttc     56040
tattggagtg gttcacgctt atatatttta gttgctctaa tgcaaggtgt ttcctaaaaa    56100
gtttaaggaa agtataactt tattttcatg tatgatagta aataatacaa taggggggtgc   56160 atttgtgcta tgcttgtttt tgttcccatt tcagtgctca attactgtag cttctaataa    56220
ataaaattat cagttgctaa catttaaatc aaacagttcc acaagtggaa gtattgctta    56280
tttgtgagag ttgtgttttt ttaaacttaa ccttactgag gggttttaag gactgctaat    56340
tatagattgt actaagcaaa gtataaagta atagaaggtt accaagttga ggctagaatt    56400
caattagtgc caatacagtt aaaatggtat cattaacaga acatcttcat ccaggacctt    56460
tttttttttt tttttttttt ttttcagaca gggtttcact cctgttgccc agactgcggt    56520
gcagtggcct gattgaggct cactgcagcc tcaacttccc aggctcaggt gatcctccca    56580
cctcagcttc cagagtagct gagaccacag gggcatgcca ccacccctgg ctaattttt    56640 gtatttttttg tagagacagg gttttgccat gttgcccagg ctgttcgcaa actcctggcc    56700
tcaagcaatc cacctgcctc ggcttcccaa agtgctggaa ttatgggaat gagctgccac    56760
acccagcccc tccggaatct ttagattacc aacttctgtc ttccaggttt ttatgtcctt    56820
ggaaatttat gcatattttt agaggtaaga cccatcctca tcttcttcct aatccttgac    56880
atattgtgaa cacagatata tatcaatta agtagttccc tgagttacaa atatacttaa    56940
atatacttta acttattata gaaggcttac aaaaactgtg gataaataac atatatttat    57000
cttagttaat gaataactga tgctgaaaat aatgtgaatg tcaaattagt tctctttttt    57060
tctagccctc acctttgaaa agcctgagcc tctgagatgt gagatgactg ctgtaaagtg   57120
aagcagcgaa tttctagagg ctgggttcac gcttcaggtc ctctaaatcc taggtcgctt    57180
cccactacta catactaccc taaaaaatct gtaattcgca aatttatttt ttgatctttt    57240
tcataactta ttaaattttt attgaacaaa tacaggaaac agttttaaat tactcattgc    57300
tcttgaatac attggtgatt atttttcttc tctgaaattc tgttttcctt aaaggcagtc    57360 atttttggt ctcttctaaa tgacacttag tattttttagt aacatcataa cttcagtggc    57420
cacagtgagc cctcattttg caacatatgc ctacttttca tatctggctt gccttttatt     57480
atttataatt taatgaaaag aaagtaccac tctttccata gttttgtaat agaattgctg    57540
tcaacaaagt agtggatgca ctatgttata aagatttcat tgtgaaaaca tgaaatggct    57600
gttaactata catcaggcaa aataaaaaca ggaaatataa acatttcctg gaacagggca    57660
gagtatgagt aataaggtat caaatataat tggatacctg accaaatatt tttaaatgtc   57720
ttaagaaatg tcactggaaa gactggagta cttggatttg tctcttattc ttattttgat    57780
tcctaacact gtgcttggca catggtaggt aattaataaa tgtgtgatgg atgaataatg    57840
```

```
attgtcattc aattagtgac taagagagtt ggaaagggct atcaatttca aattggttcc   57900
tttaagacat ttttacgtaa gatttgggag aaaagtaaaa gagcaccata tgattatgct   57960
ttactaagag ctgcttccat tcctacattg accatgtgga ctcatatttg gcctatataa   58020
ttacattaga ataaacaaag caccaaaagt tggaaaagga agtagtagta ggagagggtt   58080
ttaagctatg tatttactgg gaaaaaaagt catgttttct tttttaaaaa tgttctaaac   58140
agtactgtaa tcacttggga attgaatgtg cttttgtgtca gacaaaggtc tttgtataca   58200
atacattaca ttttgtatac caatacatta cattacacag aagggagtgc ctggctttgt   58260
atacaataca ttcatttttg tataccaata cattacatta cacagaaggg agtgcctggc   58320
tttgtataca atacattacg ttttgtatac caatacatta cattacacag aagggagtgc   58380
ctggctttgg gaaacacatc tacctaaact cttaacatag cacaatgctg ccatacggta   58440
ggtaatacca agacaaatca gggccgttat taacaacctt gaggaaatgt cttgggaaat   58500
atttaaataa tttttgttta attataataa ggaatctaca gcctctgtga agtcatccca   58560
aactcttcga ggcaaattta gtctcctccc accctgttt tttaatgttt ctaaaggatg   58620
ttatgtataa tctattagaa aactggccaa gtgcagtggc tcatgcctgt aatcgcagca   58680
ctttgggagg ccaaggcggg tagattacct gaggtcagga gtttgagacc agcctagcca   58740
atatggcgaa accctctcta ctaaaaatac aaaaattagc caggcgtagt ggcaagtgcc   58800
tgtaatccca gctactcagg aggctgaggc aggagaatct cttgaacccg ggaggcgagg   58860
ttgcagtgag ttgagttcgc gtcactgcat tccagcctgg gcgacggagt gagactccgt   58920
ctcaaaaaac aaaacaaac caaaaaaaaa aaaatatat acacacacac acacacacac   58980
acacacacac acacatacat acatacatta gaaaactaat tacattgttt tcttaaaatg   59040
ttttaagcat ctctcttcct caaggacaag aatcttgaat ccttagtgca tatgaggtac   59100
ttaatagata tttaaatgaa tagtgagcta ctattgccta aaaatattag acatcatgta   59160
atatcaggcc tacagttgat agaaaaagta ttctcaacta agaataattt accaatggag   59220
aaaactgtta gttttcccctt ctttttcttt gctttataaa atttaaatga cattaagagt   59280
tacgtttctt ggaaaattga aaagaatatc tgtggcacaa tgggctctgg gtataattgc   59340
aggataattt gaaaagttta aagaatattt tcaataggta taagtttatt taggctctgt   59400
gtctcctctt gagatgactt tagcagtata tatttccctg gaacaccatg cactctaggt   59460
tttctaattt attggtttaa aatacatggc attttactac gtaaatattc tctgtatctg   59520
taggtacagc acctctgtgt acactaagtt agtgtatga tttttttaaa attgccttag   59580
ttttgctatt cactagatta ttttccaagg aacctactct tagatttatt aagcctacta   59640
tatatatttt gttattaact aattctctta tttttaaaaa ttacttttcc tttctttgct   59700
taaatttgct ttgttttcct aaattagtga tttggaatac ttaattgttt ttattttgtt   59760
ttgttttgtc aataaaagag ttttaagact ctagttatac tatagctata gccaatgcat   59820
tttgagaggt gcttacatat tacaattatt ttcagaaatt ccttatttca aagctttgct   59880
ttctttgaac aaagagttat ttaggaaaag aaaggaataa aaatctcaac ttattctcca   59940
cttgactagc tttattattt gcagtattct gttttttact tgttctaata cttcttttata   60000
ttttgttgtg gaattatgtc acctaacaat attttcctta acttcttaat tttagcctgt   60060
tttccaagtt aatcatttat ctgttgtttc aatgaatacc taagaaaatt ttctttgtca   60120
ggataaggca catgaggtct aagatttatt tctagaacag taagcaaatc atttctgaaa   60180
gtgtgttctt ctactattaa gtaacatgtt tattttttgtc ttttagttga agtccccccc   60240
```

```
aacccaatag gtactattct gatttgttct cctattcaca cattcttgaa ggagagctga   60300
tttatctgta cccacaaaat tataatataa ttttctcaga gtattcaaaa cattgtcttt   60360 tttattttc ttttttttga gttttcact cttgttgcct aggctggagt gcaatggcag     60420
gatctcagct cactgcaacc tccgcctccc ggtttcaaga gattctcctg cctcagcctc   60480
ccgagtagct gggattatag gcatgcacca ccactcctgg ctaatttttt tctattttta   60540
gtagagacgg agtttctcca tgttggtcag gccggtctca aactcccaac ctcaggtgat   60600
ccacctgctt cagcctccta aagtgctagg attacaggcg tgagccacca cacccagccg   60660
aaaacattat cttaatggag catttagaac gttatcactg acaaactttt ttctattgaa   60720
aatactgctt aaaagatcag gtcatgccca ccccacaacc cacacccttt gtatttctct   60780
tttacttgtc ttggcctcta gttcagattt atagtttggt aatgtctgat tttctttgtt   60840
agtgcttcag cccatctggt tggggaacag ctctatccca ctgggacctc tccctttcct   60900
catgagtgac gccagggtcc tgctgcccat aagcattctg tttgctgagt ttgtatatat   60960
ttcctttccc cagcttcgct gcctttggct gctttgtgat taagtaagac atacccatgt   61020
ttcctaaagc ctccttcgcc tttagtcctt gatgctgggg accttttggt tgggaagaca   61080
gcttccttat gtcagggtga gcctgctaca caggtatgta actcagacag tgacctactg   61140 ttgagttct gtttagtgtt tctttgtctc cctcaaatgg tacaaacgtg agggcttca    61200 actgcagtct acctttgtcc tgttagtttt gtctatcaca gcccatgccc tccaaataag   61260
agatgatgga gcagtctgct tattttctgt agcactccac aactgacttt aaaagaggga   61320
ctgggattgg gctcttagtg atgactttta atgtggattc atctgcattt tctctagaaa   61380
ttctttaaac tctctgcctc tcagctggca ctattccatg gtattttagt gctaatgggg   61440
gatcttttct aattttttgtt tttctttgac tgtttaaatc atttactgga aagagggctt   61500
agatatctgc tcatatgctc ctgctagtct acaagtcctc cagcctgatt ttgttcatga   61560
acatgatgga aataagcttc ttaaatgcct ttaatattgg atactgcttt caaggaaatt   61620
taaaatagca agcaggcttt caagaagaga gaataaatta tcagccagtc tcgcaagaac   61680
aaaaataagc caagtcatat aaaacaagtt tggagtaaac ttgttttac atttcaaatt    61740 cgagttgaac tcttcaagtg aagcttcaga gatataaaaa actttaactg ataaagattc   61800
caaacattaa tatatggaaa tgtatgagct cactgaaaat tttacataaa ttttactaga   61860
agaggtgact gaccagttgc ttttataaga ttctcaaaaa gatctcaaat cttagggact   61920
aatattgtaa gtatacgggg aaattaagac aaagatttac tatcttgtga gtttttagtt   61980
tggataatga acttaattc acaagaaatt gctttagcac aaacatgaaa accttaagca    62040
tgagaactct cctttgaag tacaaaggga gactaaagtg aataactcaa actggaaatg     62100
tagaaaattg aatttgctat gatttgaagt cctttcagaa tagccaacag attttaaaca   62160
agagttttat tgcatagttt ctttgggata tacattgaag gagaaaggag gagggagttt   62220
taaaagacaa gtggaaagcc ctttctgctt gttttggcta tggcttccat ttcagtgtct   62280
gtatttaagg gatcataaaa ggaactggaa agactggtca caatggcagc tctgtacctg   62340
tatgatttcg gatgtgaaaa gagtttagcg atttccttgt taacctatac tgctgtgaa    62400 gtcattcatt atgcagttag gcattagcag aacaaataaa gttcacagct ctaggaacca   62460
aatttaactt tatcactctt ctgatttaga atattttcat atgctttcat atgtcctaca   62520
gacgataaga agatagaatc aatacttggt gattgatagg ttatttttta aagggaaga    62580
```

```
aagaattaaa catccatggt ttcttcttaa gtaactgggg ggatgatagt atccctcaca    62640
ccaatgggga gtatagatga caggtttgga gtgaaagaca gtgaattcca ttttggataa    62700
gttgaatttg aagtgcctat gggacataca ggtacagatg actaggagac aattgaaaat    62760
ccaaattgtg aactctgctg aagattagaa gtacagatct gagattaaat tgctacttga    62820
gttcatggga ataaaatagg tcattctgca aatggttatc tcaatatctt cctggccatc    62880
tcttgggtca ccttgccaac ttttcattct ctttacaatc tctaaattct catgttttta    62940
aggctctcat cttaggccaa cttatcttgg gtcaccttgc taacttttca ttctctttac    63000
agtctctaaa tttgtgcttt taaggcccca ttctcaagct ggcttctctg ttttggtggg    63060
aactggtagc aaacattcat ttgtaaacaa cccaaatggc tagcattgag caggactccc    63120
caacatactc ctctgaatta cattttgagt tatctgaagg atcaatatct caaactagga    63180
aactgtagct ttctcattta ttttcatcat ctaattattt ttcttgcctt taagtataag    63240
ggatagagac ttgattgatt tttatgtaca acaagttaaa aaatttaatt aggcgtcttt    63300
gccatttaat cagtttatac ttcttgaatc ttttccagtc atcaaaaagt tgctgagcat    63360
gcgcagcttt acttactagc ttatagcatg aagaagagta aaataggagt ggataaaggc    63420
acagtggtga gtagtcagtg tttccaatta atctcaaagt ttaggattaa tttagcgtga    63480
attctgttct tttgtgtctt cctgcttttt gacgtggtaa cctgccataa caaaaggaaa    63540
cagcaggaaa cttggtacca attaaaacag tcttcttccc ccaaagaacg aactgtcagc    63600
aaacaatctc aaattcaaag tgataagtgt tttagagtga acaaggata aagagacaag    63660 gctattaaat tttaacatct gctggaacac aaagcgcatg ccagtagaat taagtttggc    63720
atttaataag atacaatttg cacatcagaa atgaaataga tgcctcaagg catggtatat    63780
atatatatat atatatatat atatatatat atatatatat atatgtttga gcgaggggca    63840
cttctagcaa aactgaatac actggtataa atgtctgcgt gaaaattttt ttatccattc    63900
acttttggtg tgtattccag ctgtgagtta ttcaaccagg ctcactaagt ttgagtctga    63960
ttaataacgt ttaaggtcac atctgattaa cagtatttga agtttgaatt tgttctaaga    64020
tgactcaagc gcaataacat tttctatatc aaaatgaatt tccatccaaa tagggaggaa    64080
atctgaaatt tcagttccag tgttgactga gatgctctgg atgagcctgg actcagagct    64140
caccaacttt ggatctttat gttaagtagt cagtggggtt gacttctaga ctagagatca    64200
aaatgttcta cacctcttga tataggtcag tggctgatgt aatgtgcttc caacaacttt    64260
cttttaacta aaacagtaca tataccaagt tggtttgtca caatgggaac aaaacagaaa    64320
tctgacaaca gatttctcta attttttgtg tgtatgtttc tgaatgggct aaaatacata    64380
attttactct tccttggtga agatgctttt ataagaggac gtgtttaaga aaattaagaa    64440
atgttgtagg tagccatgaa agaattattt taaacagaat tagtatagag gtgtgaagat    64500
ctactgaagg gtgataagta agtgtggaag agatggtgtt cagcattggg cttcagtatg    64560
aataggtaga agatgagcaa ggcttagaga caagaagttc attcaatagg ctgttgcggt    64620
tatccagcaa tgagatggtg acagcatgag ccatggtagt aaaagtaagg acatggataa    64680
tttgtgggtt ctacagacaa taagaacata gaaccgatag gttatttttt aaacgggaag    64740
aaagaattaa acatccatgg tttcttctta agtaactgcg tggatgatag taccccctcac    64800 actgatgggg aatgtagatg acaggtttgg agtgaaagaa tgaattccat tttggataag    64860
tagagtttga agtgcctatg ggacatacag gtacagatga ctaggagacg attgaaaatc    64920
caaattgtga actctgctga aggttagaag tatagatctg agattgaatt gctacttgag    64980
```

```
ttcatgggaa taaaataggt cattcagtaa attgttatct caatatcttc ctggccatct    65040
cttgggtcac cttgttgact tttcattctc tttacaatgt caaaattctg gtgtttttaa    65100
ggccccaatc tcaggctggc ttctccaact gtactcttac ttgggatgat cttatctagt    65160 catgggcat taaataccat tggtaggtta acacagttca caattttctc cagcttagac     65220
cccttgctga tttcctgact tgtacactca actgcctgcc taatataccc actttaatga    65280
taatgtacat ctcaaactga gcttattcga aatagaagcc ttaatttttc tgtcagtcat    65340
attgttccca tttacccatc ctaacaaata gcaccatcat caacctttta gctcaagaca    65400
aaactctagg cattatcttg ctttcattcc tttcatgtac tttctcacat ctaatccatt    65460
accaagttgt tctgtttctg ccttcaaaat gtgtcctaaa tttatccatt tctctgccac    65520
tgctattctc tagttcagga cattctatcc tttctcttgt attactgcgg tctctaaact    65580
tcatgtatct atgttttata cttttaattc attgtctata cagctaccag agtgatcttt    65640
taaaggtcta aatcagttca tgtcactgct ttatatataa tgcacctatg gcttcccact    65700
ggatttaaat aataatctta acactttact cctccatggc ctttacatac ttctagccgc    65760
acctcaaaac actcctcttg ttcactgaga actaactaga ccagtttctc ttctcctcag    65820
ctatatcatg ctaatttatg cttcagtgcc ttttgtactt ttgttccctc tagctgaatc    65880
attcttccag gtcattctat cattggcttt tcattcagt tcagatagat atcagcaaat     65940
caagagagtc tttccttacc tgctctatct aaatagtcct gttttagtcc tctttatctc    66000
atcactcaga tttatttccc tcatagcact catcagtctg aaattgtttg tttatttggc    66060
tacttgtttg tctagataaa cttcactggt gaaggaatcc agactatctt gttcatccct    66120
acatccctag aacctagaac aatatgttaa agataaataa ataaatagat gaaagaatgt    66180
tgaagagaag agggtccagt ccagccccct gaggtgacca gcatttaggg aataagccga    66240
ggcagaggag ggccattaag aaggagcaat gagagataga ggaaaactaa gaacaaggtg    66300
tccctaaagt gagagtgtcc taacacaggt ctaaatgaaa ggatagttca gaagagggca    66360
ctgcagctgg ctgaaagaga acaagaaagg ctgtaaggtg gaggtgaatt tttaattgag    66420
ccgtgaaaga tagggaaatt ctgtatgaag gagtaaatgg aggcatagag gcatagaggc    66480
agaagatgca tgcctgtttg gggaatagtc atcccatttg tctttcacat atctcattta    66540
atacttctca tttaatcctt ttagtgttaa tgttgtcact agattaaaaa acaaaggctc    66600
catcaggatc acacagtaaa cagaagaata tggatttaaa tggagatcta tctgactgca    66660
aagactactt actgtaactt aagtcattga gattccttat ggccacctca tattcaccct    66720
gcatataaca gtatgccaat gtaggaatga ggcgtgaata agcagggtaa caatagaaac    66780
atattctcac cttgattatt cctttggtag cttcaaggga aattgagttt gaggataaag    66840
taactcttcc catgtcagca ctttatctgt cctgaaacat gagaaattcc aaatgttcaa    66900
gccatgcagt ttttatctag tcagatggtt gagaagtcca ggttacccat agttgtaatg    66960
aatacctcct ctttatcttc ttaatgttct gctttgccaa atgatctata aagattactc    67020
agtgtacctt tcagattgag gtccagcaga ctttcagaac actacattta attacagaaa    67080
cccaactaat aaaataataa gctcatgtta gtttcaggtg ttgatttgtt tttaatgtag    67140
tcaataatat ttacatataa tgactggcaa cttaacagag ttataataga ttattcacct    67200
gtatttgcct ttatttgtgg gtatacacac atatatacat gccttaaact agagtaaaat    67260
catttatgca tactaaatca aatttgagag tcccaaaatt ttcaaattgt gtatggctgg    67320
```

```
tctatatttt ctaggactgt cctttctggt ttaaatgaaa ttaaaaattg aattaatgat    67380
attagtctct tttaattttc tattttttc atgattaaaa aatattaatt tccagccagg    67440
tgcggtagct cacgcctgta atcccagcac tttgggaggc tgaggcgggt ggatcacctg    67500
aagtcaggag ttcaaaacca gcctggccaa catggtgaaa ccctgtctct actaaaaata    67560
caaaaactag ccaggcatgg tggcacgtgc ctgtagtccc agatacttgg atggctgagg    67620
caggagaatc acttgaaccc aggaggcgga ggttgcagtg agctgagatt gtgccactgc    67680
actctagcct ggtcgacaga gtgagaatct gtctcagagg aaaaaaaaaa attaattttc    67740
cccattcccc cacccaccca ccaaaagact ccattggagt tttatttac aaatgcatct    67800 gctcatctac ttcttttaa gtgcataaac tagttttaca agcttgagtt taaatcttaa    67860
ctcctcaatt cttttctga catagaaata tacaggtgca ttatgaaata gctaatagtg    67920
actattttct agggctgtaa ctcaatattt ataagcataa tgatataacc tgctgaagtt    67980
tgacacgtca gtatagttct tttgttattc taagtcataa aggcagaatt tggaaaaatt    68040
cacagctttt caaatatgca gaagaggaaa aattgagagg aagcatacta aaatttcttt    68100
agccaatttt aatcaaattg agtttgaaac ttacaggatt atgcttcaaa gcttgtaatg    68160
atcgtcaaaa gtagccttat tcaaaatgac acactaattt ctaccacatc tgtattcttc    68220
tcattgtaag atgttacata tacctatgct tgaccaaatg gacttcctgc tatttttaaga   68280 tattttttctg tgttttaagt ctttctacaa attttctcaa gcatttccct ttacctagga    68340
tgttcttctt tcactgcaag tgaagacatt ctaaaaattc ctaaagcaca ctaccaaaag    68400
cccttcattt ggatgaccca ccttcctatg agtctcccata gttgcatgtc tgatggcatt    68460
tattttaact ctatgatctg cttctaaatt agataaaagc tctcagagag aactatgacc    68520
aattgtcatt ctgtttccca tggcacctag tacagtactc tgctcacagg ctcaataagt    68580
aatgagttga gctacgtttt tttaaggcag agtctccctc tgtcgcccag ggtggagtac    68640
agtggtgcaa tctctgctca ctgcaacctc tgctgctggg ttcaagtgat tctcctgtct    68700
cagactcccg agtagctggg actataccac catgccacca tgcctggcta acttttagta    68760
gaaacaaggt ttcaccatgt tggccaggct ggtctccaac tcctggcctc aagtgatcca    68820
cctgccttgg cctcataaag tgctaggaca aaagtttgcc attgtcatgt tacgatatat    68880
attggttttt gtccatggtt tctggttcat agctccaata tccccttttt cagtcttttg    68940
ttagaatgtg gggtgtgttg gacctcgggg caggcttag aaaacagaat ctctcctgcc    69000
ttcctttcac ttgtccccg agggagattt tttttttttt tttttttttt gagacaagac    69060
ttccctgtgt cacccaggct ggagtgcagt ggtgtgatca tagctcaccg cagcctcagc    69120
ctcctaggtt caagcaatcc tcccatctca gcctcccaag tacctgggac tacaggcaca    69180
tgccaccaca cctggcattt tttttttttt ttttttttt gtagagaggt ttcgccatgt    69240
tgcccagtct ggcctccagc tcctgggctc aagtgatcca cccaccttgg ctcaaaccac    69300
cacacccaac cctgagggag attctaatct tccccaccct tctgattttg agtcttaaaa    69360
ccccagagaa ggtcccaccc tttgcactgg ggaaaggaat gctgatgatc atgaagcctc    69420
cataaaaact caggaggatt gagtctgggg agcttctgga tagctgaacc agtggaggtt    69480
cctggaaggt ggctcatcca gggaggactt agaagctccg tgcactttcc ttatacttca    69540
ccctaagcat ctcttcatct gtatccttg ataaaccagc aaatataagt aagtgtttct    69600
tgagttatgt gagctgcttg accaaacgta ttgaacccaa agagggtgtt gtgggaaccc    69660
caactcgaag ctggttggtc agaagttctg gaggcctgga tttgtgactt gtgtctgtgg    69720
```

```
caggagcatc ttgggaactg agcgtttaat ctacggggtc tgacactgtc tccgggaatt   69780
aaattggagg acacccagct agtgtctgct gcttgttatt ggggagaaac cctcacacat   69840
ttggtcacaa gagagaagtt ttctgttttg aatattgttg tgatgtgaga gcagaggaaa   69900
aatgcatttt ggagaggttt tttcctacac agccataggc agtgataaga atatgatgct   69960
tttttccaga aaatgctaca tgagaccttt ttataaaatc taattttctt caactgagta   70020
gcatttaaac taaaaagaat aggttatttc agtgtctctc tgtaataaca tcttacaatc   70080
acttgtcaga ccatgaaata atgttctaga aaatcagtga aagagctttt taaactttgt   70140
gacatttgac ttatatttat taccaaaaag cctgaattat tattcagcac attataattt   70200
tatttaaaat ttaaattaga gatgaaatac ttgtaaatgt ttataagatt ggtagctgtg   70260
tgggcttcca gagttagaaa tgcctctgag aaaagattta gagttttgaa agtattttga   70320
aaaaagaaac agaaaggaat acaacatttt tcccagcact gcttcaataa tgcagtcttc   70380
agcatcatct caaagcaata actgcagtac agatgagatc agccagtttt tttttccccc   70440
ttatctgcag tgattttacc atctcttcat gctacatctt accacaaaga gaacattgaa   70500
acatgggaaa gagtttgctt tgatttcaac cagaatgcca actcatttct ggggttctaa   70560
accataacct ttttagcag agcagtgtag aatttttata cgataccata aatggtcggc   70620
ctgagtaaca ttttaactgt aagtcaaatac ctttgaagag acatgtctga caactcagag   70680
ttctattttc tccatgtgtg actaaagtac cttttctatt aagagatcaa ccaccatttc   70740
cttctactct ttgttctccc cttaaataaa gttaattcag cttcaaaata tttatgatc    70800 ttgattacta actgtgggtc tttagaagac aatgtaaaac atttccatgc tgtgaatatt   70860
agagctagta tacttggagt ttggctagta tttctggggg aggtagaaga ggagacatag   70920
agtacaaatg agtattttta aagccacgct gactaaaaca aaaggaatgt tttatacatg   70980
tttatttcat agtacttctt tgaaacaggt cgggggagg agagttaaaa tattgctttg    71040
aattttaatc aaagttcttt catggaattg ttggtgcttc tggtaataac agttctataa   71100
tctttgtgag ttaatctgaa atgctctttt tcttcatcgt aattcagtgc ttgtcttaac   71160
tggtggactt attttatggt attatgttta taagatggca actaaaatca gattttttat   71220
actcctaaaa gatggatacg atagagggga aaggggtaa gctacaactt ttaggttgtt    71280
ggtgatattt gaagtgttta ttgcttctga tttacattta tatattatat tcaaatataa   71340
acttaaaaag taatgatttg ccacaggtta aagcagaaca tttatatgat atttcctaga   71400
tgttttcctc tacaatcctg ttttttgttct atgaaaaatg ccataaaactt ggatcattca   71460 ctaattaatt tgaagctgtt ttcaaacaaa aagctaattc atcttttagc ggatttagtt   71520
ataatcgtga taacagatgt atagctaagt ctgttggaca aactgttggt cacatcaatc   71580
ttaaatgcat catacagcgt gatgtgaatt tatgatattt cctaggtaat gttaaggtta   71640
tatgaaaatt tctttgcagg tagttaagtc ttatttgaa ttcaaatgtt attttcaata    71700
catacgtgga agtgtatttt ttgtttgtcc taaatgttta gatttttga gtttacaatt    71760 ttttttgtgtg ttcttttcttt gttccttgccc ctccctgcat tctctatgaa gatacatgtc   71820
agcactatgc aacactaaaa taacaatcaa ccaaattata tcctatgaac agacctttct   71880
cttcatttca aaggcataac ttggatggtc tgtttagctc atggtgaaaa aaaaaagtta   71940
tgattttgta tttgggcaaa gtacaggtga agagcgtgaa tcattagaac agcaatataa   72000
ctggaagaag atagtttagt ttttacaagt taaatttgaa gctaaagcaa aacttgcata   72060
```

```
ggtatgtgtc ctttgctctt gaaaatgaac tcagaactct acatctgagt ggttttatga    72120
atttatactc tcctagtcca caggttctca tcagtgcctc aagatctatg cacagattaa    72180
aattacataa gatatcatat actacatctg aattagggtt ttccaaagta tgctattcca    72240
tggaaatact gttttattcag ggtgctccat aaacaatgat cctgtgtttc attatgtcca    72300
ggaaatgcca cacagcacct ttccagacat cctatcatca tattaaagac tttgaggcca    72360
tgcattaaag aaagttttaa attagaaaaa aaataagttt tcttgcttga gcacagaact    72420
ttattttttc tcaggctggt tctccttttt taaaattaca cgttaatatc ccaaagaacc    72480
agtcccatag atagatatca catatgataa gaatctgttt caatggtgtt ggtgtacatg    72540
tgtgttcagg tacctacaca ttaggacaca tctctagttt attaatactg cacttataaa    72600
gagacatggt agagacatca agaagacatc atttttgggt ggacaccatt gcctaggacc    72660
tgcttcttaa tgtcaaaaat tcagaaccc aatttatct ctcccgcaga gttgactcga    72720
gtgaaggaaa ttgagttgtt ttaattaaac tcacatgaga ttgatgttta aacaaaattg    72780
taagtttatc aattaataat caagaattct gattttaat tttcaaaata ttatttatgt    72840
ccactgtcca gggtacttgc tttaagggca cccagtgatt cttgaagatg aagagtctta    72900
ggaatattta ttttctagac ctcaatgaag aaagcttttt aatcatcctg ccccatagaa    72960
gaatttatgt tcctagtgat gtgatcatat tggccaatcc agtgtttctt ttccaaggac    73020
agtactgata aggagcacca aatctacctc tttgtcctga acagatcatc tccatctatt    73080
catagtttgg ctcagaagtt ggacaaggct gcattttata tctacttctt cctcatgtcg    73140
gctatgccat gccgtttcgt tcttttagct tgtttactta tgtgtaaaat gaggtaaaaa    73200 ttacacccctt caaaccgaaa gtggtcttcg tgatgagtta tttaattgaa gccccagtag    73260
atatttatca ttgccagttt tagagaatca tagcatttta gaacacaaga tgaccttaga    73320
tgtaatcatg ttcattcccc tcgtattata aattttttaaa aattgagatg tggggtggtt    73380
gtgacttgct cacaaaccca catttagaac caaaactcag cattcttgtt ctgactgtgt    73440
ctatgtcctg taggtatatg tcttgtcttc tcagttaaat aattaaagat tcttaaagat    73500
agagaccata ttttatgcaa cttctggatc ccataaatta tgtttccaga gaacctttt     73560 gtaatgaaaa aatatatata atgtctatat tatatatata gtctattact attttgataa    73620
tctaaaacat gctatataat tttaggcgat cttaacctat ttatcagagc ttttcagatc    73680
aaagaaaatt agagtaatct tcatcatgta tgggaacatt gatgtatttt tctgatgaac    73740
acatggttat atgatactct tttaaagcat ctgtattact ctttcttctg atagactggt    73800
tattttgttt atgttatgaa ataatgttgg cagcttttca ttagaactga tacatattga    73860
aatttcttaa attgatagct catggatgtg cagttggttt aatggcatct ccattattaa    73920 tcttaagaa gatcttcatc ttactctcaa aaataaccgt aatatcctac aaattaacta     73980
aaacatgatc attgctagtt gttccaaaat aggaagaata aaaatgacca gattgttatg    74040
gtaaccagtt gattaagact agatcaatag gaaaacgaat ttattcaagt ctgtacaaaa    74100
cttctccaaa acatagatgg catgcctttt gaggcaatgg tagggaacaa atattttttg    74160
agaaggagca gatttaggg atacagtaca gtacataatt gccaaaatgc ttgtgttaca     74220
aggattcctg gtacagagtt tttaaataaa atgctaggta tgtcatgttt gtttcacatt    74280
aatattgtag agtccctgg ggatgtgaca atttagttga ccaactctaa tatagttaat     74340 ttctacccttt tgatagcttt gtggggtttt gtttgtttgt tttttgtttt gccattcttg   74400
attttagggc tgaagatatg agacaatgta tcaaacagta aagaattatg cattgattaa    74460
```

```
gatcatcttg gtgaattaga tgtttattat ataactcgac tttaagactt tgttcagatc    74520
tcactatctt aatgagattt accctcatta tatagtattt aatagggcaa ccactccccg    74580
atactcttga ttcctcgtta gctgccctat tatttctttg ttttcccctt agcactcaac    74640
attttcttac cacaccacat aatttacttt cttattgtgt ttattgtttt tctcctcatt    74700
agaatatcag gtccaagaag acaggagtat ttatctcttt tgttcagtgg tgtgttactg    74760
gtgactacta gagtgcctga cacatagaat atgttcaata atattcgtt gcatgaaaga    74820 atgaataccT tgacagatta ttttTataac tctaccagtg tcattatata actacactga    74880
atgattatga gccctcctag aaattacata aagttcttat atattattag aacccatttg    74940
ttggccttat gtaatggttc tattggaaaa atcatacctc cgtatataaa aatgaaagta    75000 tttttttcT acaattgccc ctcatatata ctattatagt ctccttcacc ccattcagcc    75060
attaatgtct tcttgaccag gtaacataat ttttacagca cctttTggtt attagaacaa    75120
ttttatttgt ctttcaaact cagtcctatt cattttaaaa ctcccaactc aagcctgagt    75180
cagtgttctt ctcccagcac aaacttaaac actggctcca acccTtggag ttgaaagtag    75240
gggagcctca ctcctgatac ctcccctccc cctctaccgt gagcaccagt gcctaggaga    75300
ttgggcagga ctgaggaagg atgaaaagga gctcagggct ccTtaagcac ctgaacaaga    75360
ctggaggact ttggatgttg ctattttTct gcctggcatt gactggctat tggacgccct    75420
ctgtgaggca ggcatccgaa tactggcttt cttgacatat atggagcgtt ctttagagag    75480
gcctacaagg gctctcactg cacagtaccc tgataggaga gatctgtcct tatttcttct    75540
atcaccatag ctacttcagc tttgcctgct gagtccaccc cacagtctct ttctgctggg    75600
gcatccttgc cctggacaga ttcttagagc atgaccaagc ctaaacaact tctgcaattt    75660
ttctaagtac acttTtattt aattgaaagt ttcaagcatt ggataatata aatgtatcct    75720
agacagtgtt ccagtaagga caaccagctc acaattatcc attctaataa tgggagtcaa    75780
ctgaaataga aaaatataga ttttTaaaat aatttatgag aaacaaatat ttgtgacaca    75840
gtacatttct aattatgttt atcttTatta ttattattat cgtttccttc agtacacact    75900
agtttggtga gacttggaga aaggccagga ataagcccaa attcaaaaaa caattccagg    75960
attaacagat aagtggataa tagagaattg acaaagatc atgctcattt taccaataag    76020
aaactggttg gttaacttgg gttgcaaact gaaagcagat ttatactaaa ctggcaggtg    76080
tctccagatc ttaaatgcag atctctatct ctgagttaat ctgcctctca tcttcaatgg    76140
cattcctctg aattttTctc cctcaaataa tctatatatt attaaattTt gtttatactg    76200
ccattttaag aaacagattt taaaacttta aacatgggaa ttaaataggc cctactgagg    76260
attatgaaaa acctgacaaa acctcctatg cacatgattt agattaggag cagtgcacac    76320
gctgtatgtg tatgtgcagc tacttgtcca attaacacct tttcagaaat ggaggaactt    76380
tctctgagga ctTtgacata tttgtgtgtt cagcagtcct ttttcttTtt ttttattttt    76440
tattttttTa ttattatact ttaagtttTa gggtacatgg gcacaatgtg caggttagtt    76500
acatatgtat acatgtgcca tgctggtgcg ctgcacccac taactcgtca tctagcatta    76560
ggtgtatctc ccaatgctat ccctcccccg tcccccacc ccacaacagt ccccagagtg    76620
tgatgttccc cttcctgtgt ccatgtgttc tcattgttca attcccacct atgagtgaga    76680
atatgcggtg tttggttttt tgttcttgtg atagtttact gagaatgatg atttccaatt    76740
tcatccatgt ccctacaaag gacatgaact catcattttT tatggctgca tagtattcca    76800
```

```
tggtgtatat gtgccacatt ttcttaatcc agtctatcat tgttggacat tagggttggt    76860
tccaagtctt tgctattgtg aatagtgccg caataaacat acgtgtgcat gtgtctttat    76920
agcagcatga tttatagtcc tttgggtata aacccagtaa tgggatggct cagtcaaatg    76980
gtatttctag ttctagatcc ctgaggaatc gccacactga cttccacaat ggttgaacta    77040
gtttacagtc ccaccaacag cgtaaaagtg ttcctatttc tccacatcct ctccagcact    77100
tgttgtgtcc tcactttta atgatcgcca ttctaactgg tgtgagatga tatctcattg     77160
tggttttgat tttcatttct ctgatggcca gtgatggtga gcattttttc atgtgtcttt    77220
tggctgcata aatgtcttct tttgagaagt gtctgttcat gtgcttcgcc cacttttga    77280 tgggattgtt tgttttttc ttgtaaattt gtttgagttc tttgtagatt ctggatatta     77340 gcccttttgtc agatgagtag gttgcgaaaa ttttctgcca ttttgtgggt tgcctgttca   77400
ctctgatggt agttcctttt gctgtgcaga agctctttag tttaattaga tcccatttgt    77460 caatttggc ttttgttgcc attgcttttg tgttttaga catgaagtcc ttgcccgtgc      77520
ctatgtcgtg aatggtgttg cctaggtttt cttctagggt tttatggtt ttaggtctaa     77580 cgtttaagtc tttaatccat cttgaattga ttttgtata aggtgtaagg aagggatcca     77640
gtttcagctt tccacatatg gctagccagt tttcccagca ccattatta aatagggaat     77700 cctttcccca tttcttgttt ttctcaggtt tgtcaaagat cagatagttg tagatatgtg    77760
gccttatttc tgagggctct gttctgttcc attgatctat atctctgttt tggtaccagc    77820
accaggacca tgctcagcag tcctttttca agagatgtga agtacatctt cacagatttt    77880
taaatattta gatagaaagt tcttacagaa tgagaaataa aaagttagct ttgccttaaa    77940
aatattaatt caccttatat tctccatact taatccatat aggaaacatt atattccagg    78000
tctaacatgt ggcttgctta cattaatttt gctgttgaaa aatatatgtt ttggattatg    78060 ttttaaaat tttagcttta atatttaaat attaaataat gttaacttta aattaacgaa     78120
gaatagtttt taattttata agaaatgccc tataaaaaac actttcttta cctcaagagt   78180
gagacttggc aaccatacca atattacata gtaatttaa agtcaaacga atggagaga     78240 acttaataga tacagaagat aagaatttaa actaacattt tgctcgggat tttagaacac   78300
tatacagagg gaaatttagt agacaataat gaagtccata gcattgcaca catcttgaaa   78360
taagtgtata attgacacaa gctatgtccc atgttgatag gaagaatcca aaatagtttt   78420
ggagaataat gccatctatg caggaggtgt ggccatatac atcatcttta ctcagtgttt   78480
ttcatgtcaa taaatattta attcctaaca ctctgaatta ctaatagagg tgaagcctgt   78540
cagtggaagt gacagagaga tacacagtga ttcccgtaag tttgatcctg aaacacagtg   78600
cctttagcag atatagttcc cataagcaag cagtctgaag tatttacccct cagtaatctg  78660 aatgtataaa taaacaggat tcatgatggt agagtaattt atatatactt gtagtattag   78720
gacatgcaaa acttattta tggaaaaaaa taatttacta ccttatagta tggcaactat    78780
acaaatctat aaaattgactc ttttgtcccc ttgaaaaaaa gctgacataa aatttaaatg  78840
atgtgtattt tttcttagag caataaaaga tatacccca cctagaaaag caataaacca    78900
aaaaataaaa caaaaacaaa atcaagccct cttcacaaat ttgagcatat ctacagcttt   78960
atgtggtgag agatacagct accattcttg agtaatccga agagtcaaat ggtatggagc   79020
aaaattacag tcctaaatgc atattggtga aatgagatgc tgatccattt gcacactaat   79080
gtgctatttt taagtcatgc atcatagcat cttcaaagag gcctgtcata attatgatgg   79140
attagactgc agagtcagtc ctagatgcag taattgtttc acagatgctg ccaatgcgac   79200
```

```
tagaatttat aataaattat tttcagagag gcgggagaag gaacaaaatc aaaggaaaac   79260
tgctgtggct aaaacctgtt ttggtcttag gaaaccaaaa tgttagctag tagtcaaaag   79320
gccagtattt tcaactgaga taaacatgct tcattaatac atgcctctga catagaagat   79380
aaaggttaac ataattgaca tatcagccag tctctctctc tctctctctc tctctctctc   79440
tctctctctc tctgtctcgt agcttatgaa aatttattct ggggcattag ctgaaattat   79500
tgagtggcca tataattgtt gcatgtttct atttatgtta aattgcctgg ttataatttg   79560
acctttagaa tttctgaaaa aaatggtggt atttatagta aatagaaata ttcttttttgg  79620 ttccttggaa gcccatgcat tacaaagaac attagattat tggaataaaa ggatagacat   79680
acataatatg actagtggga tctaaattat aaccttttaa aattgtaatt taattagtct   79740
gtcatttagg caaatgataa tttctaaaac tgccttttta gacttaaaaa aataccaaag   79800
ttcttataac tttagcatta tgttttgttc attcttaaag tttaattcac tttgttgcct   79860
ttttggtaaa cctatgaaga aatctcatgc tgcaccatat agtaaaaaat cgtgtgtgtg   79920
tgtgtgtgtg tgtgtgattt gaataatgag ctatgtgtta tattttgata agcaaagata   79980
agtttatagt gaagcagata aacatgccat gtattttcct aggttaaggg ttcaataatc   80040
agaagagctt ctacaactca tttgccttct cactagtttt tttgaaattg cgctctatga   80100
gttttttatg tggtgttctc tgtacttgct gactactgat gcacatttct ccttaggtca   80160
ctggttctcc tccctcagca atgttgtagg tagctttgat gaacattcgt tgtcagcctt   80220
ttacctttga cttagtgttt ttctctcata ctacggcaag aagaaatgaa gttaaatttt   80280
acaagagtga cttgggtggc tgatatgccc acattgacag ggacaagagc tctagtcttc   80340
ccctctcctg tattcccatg gcacttcagt agtctcattg cctcaacata accacagttc   80400
agggcagtag aggatgtttg catctttgtg ttagctccat gccatggcaa ctgcactgag   80460
tgaggattca actcagtgca gcaggactga aaaaataaat gaactaatgt gtcttgagct   80520
ccaattctct gagtgacatt atcaggggag attcataaat catcctcaaa tattctagag   80580
aaaaatcatc agcagtccag cattgcaaag ataatctggg aaggtggcaa agaagggatc   80640
agaataactc tgtggcagct tcaaattcca tgtcctaaaa gtttacgttt tctttttat   80700 tctatcccaa accacataaa gaaatgattt gttggcaaaa gacatgcaaa atgcccttaa   80760
tcatcttaat aattacagac ctacagatac gtagccaaaa tacttgtttt ttaatcctaa   80820
accttaaaaa aaaagcttaa attgttggct aaatgtgaat ttaataacaa aacttactcc   80880
tttaattatg cacttgtctt agtattgtgt ggtgggaaga gctttagaga gctgccagag   80940
tgcttaggcc tagtccctgt gggagcctct gttttggtgc ttcaccatgg gcagattcct   81000
cagttttcac atctttaaaa tgagaaaatg gtactagatc cttgctgcta ctctgaaatg   81060
tttatacatt gttaggacca ttgttacata ttattactta tatttgagtg tcaccttaga   81120
atttcttagc cgtgtgatat ggtttggttg ttggctcctc taaatctcct gttgaaatat   81180 aatcccagt gttggaggtg ggggcctggt gggaagtgtt tggattattg gggcagatcc   81240
ctcatggcat ggtgctgtcc tcctgatagt gagttctcaa gagatctggt taagggtgtg   81300
tggcacgtcc ccctccctgt ctccttccct ccctctctcc ttccctccct ctgtccttcc   81360
ctccctcttc ctcccctcttc ctctctcttt ttctcccact ccagccatgt tagatgcctg   81420
ctcccctttt gctttctgcc atgattataa gttttgtaag gcctcaccca aagcagatgc   81480
cagtgctttg cctcctatac agcctgcaga accatgagcc aattaaacct attttcttat   81540
```

```
aaattaccca gacagctatt tctttatagc aactcaaaaa cagcctaaca tacctttcaa    81600
aaggttaaaa tgctatttag tcattccaga agcaagatct ctttgtccag aattctggaa    81660
ataaagatgc caaaataata tggcatgtat ttgatctcag ggaattttca ttttttcaaa    81720
aggaggaaaa aagagtaata taattttta atattttggt agctctaaca gtgcttagaa     81780
ccagttctca agagcacatt gtgaaacttt caggaattgc atgagctgta ggttgataac    81840
atgatgccag ctataaccca taagagcatc tcctgaggaa tatgttaaaa actgtattca    81900
ttcttaaatt ttaactaaat gcaatgagtg aagtattgac atcatgaaaa tcatccctgg    81960
gtaaacaatt agtcactcca ggttttccca aaggttcttc tgtctctgtt cttgtatata    82020
aacttcgtaa ccagtttaac aaccccaaaa aaggccttaa ttttgattgg ccagcatcct    82080
cttaggaaag acattgccat cctcttgtaa agttgcttct cattctaaaa taagaattgt    82140
ttccatctag ggaatgattt ttataggtag aatcttattt ggcatggact cttttgcata    82200
cagtgaatta caatgtgtag accttcaata gcaaggtgtt tgaatattta gttgcacaat    82260
agagcagtat cttaatattg tataccatat taattttgtg ttctctggtg taagaaaaaa    82320
tagaaggatg tttaatttca actaaaaaat caatcatgat aattcaaaat atttctgatg    82380
agtcatttat aagagcagat atgaattaaa attatatttt tgttcttagt ctctgagaag    82440
caaaaatcac acaaataatc tccatagcaa aaatttatat ttatctgaaa aacagtttaa    82500 cttttgaaaaa cttttctttg caatcattta aattcataaa aaaaattcat taactctact    82560
ttcactgaat agcaggtgaa tagcaggtca atatctacaa aaattcatct ttgaagattt    82620
ttttatctta cgcaaaaatt attgacttca tgtagacttt ttatgcaagc ttgaaaacac    82680
tgtgtaaatg accccataaa aactacagca tgaaagcttt ttcagtattt ctacaatgag    82740
caaaatgcat aggtctcatt tccttctctt ttattaagca aaataatact ttatcaacat    82800
cagtatgcaa gcactaagag cttgaaagag tactgtgcaa gtgggttact ggatcataat    82860
attccagggt atgtatataa aaagtgtgat ttagcacata ttaaagtaaa agaaaatatt    82920
gcatttttct ccttctaaaa tggcagttta ttagtttaaa tttcctgaaa taagatttaa    82980
agaccaataa caaattttcc tcattctaac atataacttt cctgcccttc ttgtgaaaaa    83040
gttaaccatt aaacttttca cacaaatggt tgtataaagg acttgctgtc acagacaaaa    83100
tagttctgta taatgtttaa aaatggccat tgtgtttaaa actccatatt gaaatacatt    83160 tctttttag tcaccttcat ttcttagtag ctattattat actcaaagga tttgcccttg     83220
acactttaaa gaatgtccaa aattatgtgg aatggattat aataaaagat aatatattaa    83280
atgcttaaaa tattttatac cttagaaagt agaaaaacat gtattatgta cagatcctac    83340
aaattttata taatttatca taaatgtaca catgtatata catgtaaata cctttttgatt   83400 gctctgtata tgaattggtg ttttacagtt accaaaagaa aagtgccttt ttttggtagt    83460
atctggacag gtaattgact ttcttttctgc aggatttatt tagatttatg tctatgctcc   83520
ttaatttttg aaaagtgata gtgtcctgat tttggagaag cctctcatat caaagactac    83580
aaatcaattt tcatgatttt aaaacctaaa gtttctttat taggtgttat tgatgattaa    83640
aagccattgt ctcacccaaa ttttctactt gttcaataga aacataatgt aagccacatg    83700
gaattttaca ttttctagta ctcacattaa aacaagtgaa aaagaaacaa attgatgata    83760
cgtttgattt aacccaatac atttaaaata gttcaacatg tattaaatat ttttgagta     83820 tttttgtgtt ttttaacac taatctttg aaatccaaac taatgttttt catagatacc       83880
acatctcaat ttggactaga cacattttaa gggctcaata gctatatgtg actagtcact    83940
```

```
gttggatgat gtatatctag accatctctt aatgtatgga aggaagtaaa tctagcagaa   84000
ataaaaacat cactttgttt tctttgtcca atatgagtta taactttatt tttttgagac   84060
agagtctcgc tctgttgcca ggctggagtg cagtggcgcg atctcggctc actgcaacct   84120
ccgcctcctg ggttcaaatg attctcctgc ctcagcctcc caagtaactg ggactacagg   84180
catgcgccac catgcccagc tacttttgt atttttagta gtggcggtgt ttgaccacgt    84240
tggccaagat ggtctcgatc tcttgacctc gtgatctgcc tgcctcagcc tcccaaagtg   84300
ctgggactac aggcgtgagc caccgtgcct ggccttttat tttatttatt aagtaataca   84360
catgcttgga agttatttaa aaaaaaaaaa aaggaatagt taaaagtaat cccctccca   84420 gtgcttttct ccagctgccc cattcctttt cctggaggca aattattatg gccagttcat   84480
tatatattct ccagagatga tttttttta ttttacaaag gtataggttg tagcattctt    84540
atataaactg ttgtgtagct tcctttattc catttaatta ctgggagata cttccatctg   84600
aaaatataga gatactaatt ttaatagcta catggtatta tattgtgtgg ctgtaccata   84660
aattatttaa cataacccctt attgatgtag gttgtttcta accttttatt actgcaaaag  84720
attgtgccta catcatttaa tgtatatatg agcatatttg tcagatatat atatatatat   84780
tttttgagac agtgtctcac tctgtcaccc aggctggagt gcagcatcac aatctcacct   84840
cactgcagtg tccacctcct gggttcaggt gattcttctt cctcagcctc caagtaact   84900 gggattacag gtgcctacca ccatgccctg ctaattttg tatcttttta ggagagacgg    84960
gatttcacca tgttggccag gttggtctag aactcctggc ctcaggtgat ccactggcct   85020
tagcttccca aagtgctggg attataggcg tgagctacca cacccagcct gtcagataaa   85080
ttcttaaaag ggtcaaggaa agtgtttctg aaatttata catattgcca aattgtcatc    85140
ctacatgata tttgtggcag ttttgactct caaaagccac atgagagagt atctgttttc   85200
ccacatgctt gccaaacata gtatagtatc aagcttactg atcttcacta attggagaag   85260
agaaaaaaac tgtaccttgt tgcagttta atttgcattt ctttttatga gcaatagtag    85320
atatcttctt aaatacttaa gagccattca catttcattt tctatgaact gtccatgtcc   85380
cttgtccatt ttttagtatg tggttattca tttatttgta ggcgtcctat atgttaagaa   85440 aagtttata caacttttaa ctcttttttac atgtttattt tggcacatat aaattttagc    85500
aaactttccc atcttttatg acttctagat tttgtttcac aaaaaagag cttagccagt    85560 cattagattt ttttaagttt tctcagattg tttttaactt tggggggggt tttatttcct   85620
gtattcaaat attaaattca tctagaattt atcttaaagt gtaagggaat gatcccactt   85680
tatcattttt tcaggagatt acccagttgt tctaatatca agtatgtctt tgaaatccca   85740
tccttatctt gtagcatatt tctgtggttt gggtctattt ttgaacattc tgttttattc   85800
cattgatcat attaatatta tatgtgcaaa cacaaactat tttaagtata gtagctttgt   85860
tgcttttaaa tatcttttaa tttggctact aggcccccata caattctttt tcagaatatt   85920
cctggctacc caatttgttt attttttccaa atgaactttg gagtcaactt ccttaattcc   85980
tcaaaatatt ctgcaagtac ttttagtaag agtatattaa gtgaataatt tgacaactat   86040
ctaagaacat attatagctt ttcccttgtt ttgtttttgt acttatatat tagtatagtt   86100
ttaaagttat attaaaatag gtcttccaca ttttaaaaac ttattcctag tgtattaatt   86160
tcttctatta taactacagt attttattcc agtaaaactt ctgactggtt gatgctctta   86220
taaatcaagg ctataaattt ttcttcagct actttgctga attctcacaa actgtaacca   86280
```

```
tttttttactt gattctctag gttgaccagt atataatctt tttatctgta aacaataact    86340
ttagcgttgc tttcaacatc tatattctta ttctatttca ttttttcttgt ttatcaagaa    86400
atagctgttt taatagagtt gttttttcgcc caaaaagaaa atagtctttc tttttctact    86460
tatatcttta aaataaatgt aatgagaaag actgtgggaa aataaagcag acaccttata    86520
caatggatta atttttttag tgccatttct tctggctttc tctattattg ggactctgaa    86580
atcttcgtta gtactactct caaaaatgtt cgaatgaatg caatcagatt caagggtaca    86640
agtgcaggtt atataggtga attgcatgcc ttgggggttt ggtgtacaga ctattttgtc    86700
acccaggtaa taagcgtagt acttaatagg tagtttttttg atcctctccc ttctcccatc    86760
ctcaaagtat ccctgctgtc tgttgttccc cctctttgtg tccatgtgtt cttgctgttt    86820
agctgccact taagagaaca tgtggtattt ttctgttcct ttgttagttt gtttaggata    86880
atggcctcca gctccatcca tgttgctgca cagaacacga ttttgtgttt ctttatggct    86940
gtgtagtatt ccatggtgta tatgtaacac tttctttatc cagtctacta cttacggaca    87000
tttaggttga ttccatgtct tcgctatcat taatagtgct gtgatgaaca tacgtgtgca    87060
atatgccttt atggtagaat gatttatatc cctttgggta atatgccgaa taatgggatt    87120
gctcggtcag atggcaattc taagtcctct gaaattaccg cactgctttc cacaacagct    87180
gaactagttt acattcccac aagcaataag gggataagtg ttccctttc tctgcaggaa    87240
tgattaattc ttttagagag tcaaagatgg aatcctaggg aagatgatat ctgaggcagg    87300
tttagagtca ttgggcaaat aaggggatta agaaggcatt ctaggcagac agaaaaccaa    87360
aggcatgaag ctctgaaaca gcttactatg tttggatatt tataagctgt tgttattgtt    87420
ggagtataaa ctgtaagaga gagtaggagg acagaaaaaa cagcctgtat gcgggggggaa   87480
gaaaacattt aaacagaaat tctcaaaaga tttgggcagc cagccctct agagaaaaac    87540
atagaatcac ctagaaaggg ttttttcataa agtacacttt tcatcacccc tattctgtca    87600
cctggaatat tgataacact gaagggagtg tgccttatct ctcaggtgta tttggatgaa    87660
atagtttgag aaccatgcag gcaagtttaa gccagtgtgt taaagagaat atgacatcag    87720
atttgcattt tacaatcttc cttttgataa caaagggaac cttaaagggc tggagggggaa   87780
gggcagacgg ggctagggga ggagaaccct tttaaaaagc tactgcaggt ggggtgcggt    87840
ggctcacacc tgtaatccca gcactttggg aggccaaggc aggcagatca cctgaggtca    87900
ggagttcaag accagcctgg ccaacatagt aaaacccat ctctactaaa aatacaaaaa     87960
ttagctaggc atggtagcag gcacctgtaa tctcagctac ttgggaggct gaggcaggag    88020
aattgcttga acctgggagg cagaggttgc agtgagccaa gattgtgccg ctgcactcca    88080
gcctgggcaa gagagtgaga ctccatctca aaaaaaaaaa aaaaaagct actgcagtag    88140
atcaggagga ggcacagtga taaagagaag atctgagcta tgaagtggca gtcaagatga    88200
ttaaaggaat atataggaag tacagttgat agaacttagc aagtgattag gtaaatgaag    88260
tgctagagaa aataaagggg atatttttca attgttttta gcattttggc aaaaaattat    88320
ttaggaatga aattgatgct agtaactaag agtatgaact tcccacatta gctggtaatt    88380
ttgatcaccc ttgttctcca tgaccataaa tattttagag ttgctatgaa gacaagaatg    88440
tttatttcct gagtagctgt cagttgtcac tatgaaacat gaaaataaat atcagtttgc    88500
tatgtctagg tattccgata tttatccaca attattcctt aagatatatt agtattttta    88560
tagatagata gatagataga tagaaataaa cacatttttaa ttttttgttttc catgctcttt   88620
agaattcaac tagagggcag ccttgtggat ggccccgaag caagcctgat ggaacaggat    88680
```

```
agaaccaacc atgttgaggg caacagacta agtccattcc tgataccatc acctcccatt    88740
tgccagacag aacctctggc tacaaagctc cagaatggaa gcccactgcc tgagagagct    88800
catccagaag taaatggaga caccaagtgg cactctttca aaagttatta tggaataccc    88860
tgtatgaagg gaagccagaa tagtcgtgtg agtcctgact ttacacaaga aagtagaggg    88920
tattccaagt gtttgcaaaa tggaggaata aaacgcacag ttagtgaacc ttctctctct    88980
gggctccttc agatcaagaa attgaaacaa gaccaaaagg ctaatggaga aagacgtaac    89040
ttcggggtaa gccaagaaag aaatccaggt gaaagcagtc aaccaaatgt ctccgatttg    89100
agtgataaga aagaatctgt gagttctgta gcccaagaaa atgcagttaa agatttcacc    89160
agttttcaa cacataactg cagtgggcct gaaaatccag agcttcagat tctgaatgag    89220
caggagggga aaagtgctaa ttaccatgac aagaacattg tattacttaa aaacaaggca    89280
gtgctaatgc ctaatggtgc tacagtttct gcctcttccg tggaacacac acatggtgaa    89340
ctcctggaaa aaacactgtc tcaatattat ccagattgtg tttccattgc ggtgcagaaa    89400
accacatctc acataaatgc cattaacagt caggctacta atgagttgtc ctgtgagatc    89460
actcacccat cgcatacctc agggcagatc aattccgcac agacctctaa ctctgagctg    89520
cctccaaagc cagctgcagt ggtgagtgag gcctgtgatg ctgatgatgc tgataatgcc    89580
agtaaactag ctgcaatgct aaatacctgt tcctttcaga aaccagaaca actacaacaa    89640
caaaaatcag ttttttgagat atgccatctc cctgcagaaa ataacatcca gggaaccaca    89700
aagctagcgt ctggtgaaga attctgttca ggttccagca gcaatttgca agctcctggt    89760
ggcagctctg aacggtattt aaaacaaaat gaatgaatg gtgcttactt caagcaaagc    89820
tcagtgttca ctaaggattc cttttctgcc actaccacac caccaccacc atcacaattg    89880
cttctttctc cccctcctcc tcttccacag gttcctcagc ttccttcaga aggaaaaagc    89940
actctgaatg gtggagtttt agaagaacac caccactacc ccaaccaaag taacacaaca    90000
ctttttaaggg aagtgaaaat agagggtaaa cctgaggcac caccttccca gagtcctaat    90060
ccatctacac atgtatgcag cccttctccg atgctttctg aaaggcctca gaataattgt    90120
gtgaacagga atgacataca gactgcaggg acaatgactg ttccattgtg ttctgagaaa    90180
acaagaccaa tgtcagaaca cctcaagcat aacccaccaa tttttggtag cagtggagag    90240
ctacaggaca actgccagca gttgatgaga acaaagagc aagagattct gaagggtcga    90300
gacaaggagc aaaacacgaga tcttgtgccc caacacagc actatctgaa accaggatgg    90360
attgaattga aggcccctcg ttttcaccaa gcggaatccc atctaaaacg taatgaggca    90420
tcactgccat caattcttca gtatcaaccc aatctctcca atcaaatgac ctccaaacaa    90480
tacactggaa attccaacat gcctgggggg ctcccaaggc aagcttacac ccagaaaaca    90540
acacagctgg agcacaagtc acaaatgtac caagttgaaa tgaatcaagg gcagtcccaa    90600
ggtacagtgg accaacatct ccagttccaa aaaccctcac accaggtgca cttctccaaa    90660
acagaccatt taccaaaagc tcatgtgcag tcactgtgtg gcactagatt tcattttcaa    90720
caaagagcag attcccaaac tgaaaaactt atgtccccag tgttgaaaca gcacttgaat    90780
caacaggctt cagagactga gccatttttca aactcacacc ttttgcaaca taagcctcat    90840
aaacaggcag cacaaacaca accatcccag agttcacatc tccctcaaaa ccagcaacag    90900
cagcaaaaat tacaaataaa gaataaagag gaaatactcc agacttttcc tcaccccaa    90960
agcaacaatg atcagcaaag agaaggatca ttctttggcc agactaaagt ggaagaatgt    91020
```

```
tttcatggtg aaaatcagta ttcaaaatca agcgagttcg agactcataa tgtccaaatg    91080
ggactggagg aagtacagaa tataaatcgt agaaattccc cttatagtca gaccatgaaa    91140
tcaagtgcat gcaaaataca ggtttcttgt tcaaacaata cacacctagt ttcagagaat    91200
aaagaacaga ctacacatcc tgaactttt gcaggaaaca agacccaaaa cttgcatcac    91260
atgcaatatt ttccaaataa tgtgatccca aagcaagatc ttcttcacag gtgctttcaa    91320
gaacaggagc agaagtcaca acaagcttca gttctacagg gatataaaaa tagaaaccaa    91380
gatatgtctg gtcaacaagc tgcgcaactt gctcagcaaa ggtacttgat acataaccat    91440
gcaaatgttt ttcctgtgcc tgaccaggga ggaagtcaca ctcagacccc tccccagaag    91500
gacactcaaa agcatgctgc tctaaggtgg catctcttac agaagcaaga acagcagcaa    91560
acacagcaac cccaaactga gtcttgccat agtcagatgc acaggccaat taaggtggaa    91620
cctggatgca agccacatgc ctgtatgcac acagcaccac cagaaaacaa acatggaaa    91680 aaggtaacta agcaagagaa tccacctgca agctgtgata atgtgcagca aaagagcatc    91740
attgagacca tggagcagca tctgaagcag tttcacgcca agtcgttatt tgaccataag    91800
gctcttactc tcaaatcaca gaagcaagta aaagttgaaa tgtcagggcc agtcacagtt    91860
ttgactagac aaaccactgc tgcagaactt gatagccaca ccccagcttt agagcagcaa    91920
acaacttctt cagaaaagac accaaccaaa agaacagctg cttctgttct caataatttt    91980
atagagtcac cttccaaatt actagatact cctataaaaa atttattgga tacacctgtc    92040
aagactcaat atgatttccc atcttgcaga tgtgtaggta agtgccagaa atgtactgag    92100
acacatggcg tttatccaga attagcaaat ttatcttcag atatgggatt ttccttcttt    92160
ttttaaatct tgagtctggc agcaatttgt aaaggctcat aaaaatctga agcttacatt    92220
ttttgtcaag ttaccgatgc ttgtgtcttg tgaaagagaa cttcacttac atgcagtttt    92280
tccaaaagaa ttaaataatc gtgcatgttt attttttccct ctcttcagat cctgtaaaat    92340
ttgaatgtat ctgttttaga tcaattcgcc tatttagctc tttgtatatt atctcctgga    92400
gagacagcta ggcagcaaaa aaacaatcta ttaaaatgag aaaataacga ccataggcag    92460
tctaatgtac gaacttaaa tatttttaa ttcaaggtaa aatatattag tttcacaaga    92520
tttctggcta atagggaaat tattatcttc agtcttcatg agttggggga aatgataatg    92580
ctgacactct tagtgctcct aaagtttcct ttctccatt tatacatttg gaatgttgtg    92640
atttatattc attttgattc ccttttctct aaaatttcat ctttttgatt aaaaaatatg    92700
atacaggcat acctcagaga tattgtgggt ttggctccat accacaataa aatgaatatt    92760
acaataaagc aagttgtaag gacttttgg tttctcactg tatgtaaaag ttatttatat    92820
actatactgt aacatactaa gtgtgcaata gcattgtgtc taaaaaatat atactttaaa    92880
aataatttat tgttaaaaaa atgccaacaa ttatctgggc ctttagtgag tgctaatctt    92940
tttgctggtg gagggtcgtg cttcagtatt gatcgctgtg gactgatcat ggtggtagtt    93000
gctgaaggtt gctgggatgg ctgtgtgtgt ggcaatttct taaaataaga caacagtgaa    93060
gtgctgtatc aattgatttt tccattcaca aaagatttct ctgtagcatg caatgctgtt    93120
tgatagcatt taacccacag cagaattct ttgaaaattg gactcagtcc tctcaaactg    93180
tgctgctgct ttatcaacta agttttgta attttctgaa tcctttgttg tcatttcagc    93240
agtttacagc atcttcattg gaagtatatt ccatctcaaa cattctttgt tcatccataa    93300
gaagcaactt cttatcaagt ttttcatga cattgcagta actcagcccc atcttcaggc    93360
tctacttcta attctggttc tcttgctaca tctccctcat ctgcagtgac ctctccacgg    93420
```

```
aagtcttgaa ctcctcaaag taatccatga gggttggaat caacttctaa actcctgtta    93480
atgttgatat attgacccccc tcccatgaat tatgaatgtt cttaataact tctaaatggt    93540
gatacctttc cagaaggctt tcaatgtact ttgcccggat ccatcagaag actatcttgg    93600
cagctgtaga ctaacaatat atttcttaaa tgataagact tgaaagtcaa aagtactcct    93660
taatccatag gctgcagaat caatgttgta ttaacaggca cgaaaacagc attaatcttg    93720
tgcatctcca tcggagctct tgggtgacta ggtgccttga gcagtaatat tttgaaagga    93780
ggttttggtt ttgttttttg ttttttttt ttgttttta gcagtaagtc tcaacactgg    93840
gcttaaaata ttcagtaaac tatgttgtaa aaagatgtgt tatcatccag actttgttgt    93900
tccattactc tacacaagca gggtacactt agcataattc ttaagggcct tggaattttc    93960
agaatggtaa atgagtatgg gcttcaactt aaaatcatca actgcattag cctgtaacaa    94020
gagagtcagc ctgtcctttg aagcaaggca ttgacttcta tctatgaaag tcttagatgg    94080
caccttgttt caatagtagg ctgtttagta cagccacctt catcagtgat cttagctaga    94140
tcttctgcat aacttgctgc agcttctaca tcagcacttg ctgcctcacc ttgtcctttt    94200
atgttataga gacagctgcg cttcttaaac tttataaacc aacttctgct agcttccaac    94260
ttctcttctg cagcttcctc attctcttca tagaactgaa gggagtcaag gccttgctct    94320
ggattaagct ttggcttaag gaatgttgtg gctgacgtga tcttctatcc agaccactaa    94380
agcgctctcc atatcagcaa taaggccgtt ttgctttctt acctttcatg tgttcactgg    94440
agtaatttcc ttcaagaatt tttcctttac attcacaact tggctaactg gcatgcaagg    94500
cctagctttc agcctgtctt ggcttttgac atgccttcct cacttagctc gtcatatcta    94560
gcttttgatt taaagtggca ggcatacaac tcttcctttc acttgaacac ttagaggcca    94620
ctgtagggtt attaattggc ctaatttcaa tattgttgtg ttttagggaa tagagaggcc    94680
cagggagagg gagagagccc aaacggctgg ttgatagagc aggcagaatg cacacaaacat   94740 ttatcagatt atgtttgcac catttaccag attatgggta cggtttgtgg cacccccaa    94800 aaattagaat agtaacatca aagatcactg atcacagatc gccataacat aaataataat    94860
aaactttaaa atactgtgag aattaccaaa atgtgataca gagacatgaa gtgagcacat    94920
gctgttgaaa aaaatgacac tgatagacat acttaacacg tgggattgcc acaaaccttc    94980
agtttgtaaa agtcacagta actgtgactc acaaaagaac aaagcacaat aaaacgaggt    95040
atgcctgtat tttttaaaaaa agcttttgt taaaattcag gatatgtaat aggtctgtag    95100
gaatagtgaa atattttgc tgatggatgt agatatatac gtggatagag atgaagatct    95160
taattatagc tatgcagcat agatttagtc aaagacattt gaaaagacaa atgttaaatt    95220
agtgtggcta atgacctacc cgtgccatgt tttccctctt gcaatgagat accccacact    95280
gtgtagaagg atggagggag gactcctact gtccctcttt gcgtgtggtt attaagttgc    95340
ctcactgggc taaaacacca cacatctcat agataatatt tggtaagttg taatcgtctt    95400
cactcttctc ttatcaccca cccctatctt cccactttc catctttgtt ggtttgcaac    95460
agccccttct ttttgcctga ctctccagga ttttctctca tcataaattg ttctaaagta    95520
catactaata tgggtctgga ttgactattc ttatttgcaa aacagcaatt aaatgttata    95580
gggaagtagg aagaaaaagg ggtatccttg acaataaacc aagcaatatt ctgggggtgg    95640
gatagagcag gaaattttat ttttaatctt ttaaaatcca agtaataggt aggcttccag    95700
ttagctttaa atgttttttt tttccagctc aaaaaattgg attgtagttg atactacata    95760
```

```
taatacattc taattccctc actgtattct ttgtttagtt tcatttattt ggtttaaaat    95820 aatttttat cccatatctg aaatgtaata tatttttatc caacaaccag catgtacata    95880
tacttaatta tgtggcacat tttctaatag atcagtccat caatctactc attttaaaga    95940
aaaaaaaatt ttaaagtcac ttttagagcc cttaatgtgt agttgggggt taagctttgt    96000
ggatgtagcc tttatattta gtataattga ggtctaaaat aataatcttc tattatctca    96060
acagagcaaa ttattgaaaa agatgaaggt cctttttata cccatctagg agcaggtcct    96120
aatgtggcag ctattagaga aatcatggaa gaaaggtaat taacgcaaag gcacagggca    96180
gattaacgtt tatccttttg tatatgtcag aattttccca gccttcacac acaaagcagt    96240
aaacaattgt aaattgagta attattagta ggcttagcta ttctagggtt gccaacacta    96300
cacactgtgc tattcaccag agagtcacaa tatttgacag gactaatagt ctgctagctg    96360
gcacaggctg cccactttgc gatggatgcc agaaaaccca ggcatgaaca ggaatcggcc    96420
agccaggctg ccagccacaa ggtactggca caggctccaa cgagaggtcc cactctggct    96480
ttcccacctg ataataaagt gtcaaagcag aaagactggt aaagtgtggt ataagaaaag    96540
aaccactgaa ttaaattcac ctagtgttgc aaatgagtac ttatctctaa gttttctttt    96600
accataaaaa gagagcaagt gtgatatgtt gaatagaaag agaaacatac tatttacagc    96660
tgcctttttt ttttttttc gctatcaatc acaggtatac aagtacttgc ctttactcct    96720
gcatgtagaa gactcttatg agcgagataa tgcagaagaa gcctttcata taaatttata    96780
cagctctgag ctgttcttct tctagggtgc ctttcatta agaggtaggc agtattatta    96840
ttaaagtact taggatacat tggggcagct aggacatatt cagtatcatt cttgctccat    96900
ttccaaatta ttcatttcta aattagcatg tagaagttca ctaaataatc atctagtggc    96960
ctggcagaaa tagtgaattt ccctaagtgc cttttttttg ttgttttttt gttttgtttt    97020
ttaaacaagc agtaggtggt gctttggtca taagggaaga tatagtctat ttctaggact    97080
attccatatt ttccatgtgg ctggatacta actatttgcc agcctccttt tctaaattgt    97140
gagacattct tggaggaaca gttctaacta aaatctatta tgactcccca gttttaaaa    97200 tagctaaatt tagtaaggga aaaaatagtt tatgttttag aagactgaac ttagcaaact    97260
aacctgaatt ttgtgctttg tgaaatttta tatcgaaatg agctttccca ttttcaccca    97320
catgtaattt acaaaatagt tcattacaat tatctgtaca ttttgatatt gaggaaaaac    97380
aaggcttaaa aaccattatc cagtttgctt ggcgtagacc tgtttaaaaa ataataaacc    97440 gttcattct caggatgtgg tcatagaata aagttatgct caaatgttca aatatttga    97500 ttgcctcttg aattcatttg ctaattgtat gtgtgtgtgt ttctgtgggt ttcttaagg    97560 tttggacaga agggtaaagc tattaggatt gaaagagtca tctatactgg taaagaaggc    97620
aaaagttctc agggatgtcc tattgctaag tgggtaagtg tgacttgata aagcctttgg    97680
tcttaaatct tgggcatttt gatttgtaaa tctgaccctg agaattgggt tacccagatc    97740
aaagactcat gccagttaaa aagaacatta cctgtatttt ttatcatgtg ttatctctta    97800
agaagaggca gattagttct aaaatcaaca aattgtattt aattgaaata atttagtgat    97860
gaggaagagg tccattctag tgcctgctaa atgtataatc cttcttagaa tgtgaagttg    97920
tccttaaact tttaaatacc ttcagttaat ctttatattg tcatttatga aaaccttgaa    97980
ctaagactta tgtatctttc atctagctct ggttttaatg caggtagcat ttaattgtcc    98040
ccactgtact gggtatagtc tgctaaacat taaggagtag ttttgcatct ctccttgttc    98100
tgatactagg gtcaaagccc acttttata gatgggcagc aaaaggcaca ttggacatgc    98160
```

```
tgataaatgt tgccctaatt gtgatctaaa catgataaaa tatacataca taagtgccct    98220
tatctgctgc aagtgaccct tgttttgttt tggttggggt gggggtgtt tgggatggaa     98280 tggtgatcca cgcaggtggt tcgcagaagc agcagtgaag agaagctact gtgtttggtg    98340
cgggagcgag ctggccacac ctgtgaggct gcagtgattg tgattctcat cctggtgtgg    98400
gaaggaatcc cgctgtctct ggctgacaaa ctctactcgg agcttaccga gacgctgagg    98460
aaatacggca cgctcaccaa tcgccggtgt gccttgaatg aagagtaagt gaagcccagg    98520
gcctctcccc tctttgcggc cactgatagg aaagcccaat ctttggttga aggaagaga    98580 gttcagcgtg cacttttaca tttataaaat gggcatcaaa atgcctgttt ggcagtcatg    98640
cgataagaag ttgtatttgc taatgtgaat aacttgagat gatttcatta tctgaattgt    98700
acagtttagc cattaattag gagcagtcag agtgtctgta accacatggc ctcagttata    98760
ccataaactt gaaattgttt atgtgctcac atgctacaag tgacggctcc tgtgtgcctg    98820
gccactatat tagtatgtat tgactccact tccatgttgc agtatctgaa acagaaagta    98880
agtctaatga gaaactttgg gattcccagg tcaaatacct tccatatgta tgtagcaaaa    98940
acaaaataca aagcctagaa gttctgtaga aatagaactg attttttactt tcattcaaac    99000 tattcattat ttccacaata gtaatcaaaa ctgcttctac ttttactgct gctaaatgat    99060
cagcaaatta ctggatatgg atatatatta ttttccagga atataagaat ttagaataga    99120
actgcaagag tatgcactta aatatattta gtgcatccag ttgctaatgt tttgttttaa    99180
acaccatcca ctttgcatga agtctaaacc ttcagttgga aaaagcctca ttttttaatat   99240 tcctctactg tgctgataat cctgtataac actaaaagaa tagatgaatg ttcacggtgc    99300
tacacagaaa tgtttttttt tttttttttt tttttttga gatggagttt cgctcttgtt    99360
gcccaggctg gagtgcaatg gcgcgatctt ggttcaccgc gacctccacc tcccaggttc    99420
aagagattct cctgcctcag cctccctagt agctgggatt acaggcatgt gccaccacac    99480
ccggctaatt ttgtattttt agtagagaca gggtttctcc atgttggtca ggctggtctc    99540
gaactcccga cctcaggtga ttgcccacct cggcctccca aagtgcctta caggcatgag    99600
ccgccgcgcc tggccagaaa tcttacaagt tattttgccc acgattggtt ttaaaataat    99660
tttaattttg cactatttcc tttagtgtct ttttctctgc atccaccaaa ctatagaatc    99720
atttgctgag cttataagaa atgctcatac tgctcattgc aacagctagc caaatttgtc    99780
ctttgctgtt taaaactcta actagcatgg ttttactaaa tttatgttaa cacagtttct    99840
ctctctgggt tgtggggaga caaatcaatt ataaataatc tctttagaaa agttactctt    99900
tctatatgaa agtgtgactt gactttctat gataattatg atccaaaaat tttatggtgt    99960
gtacctgacc acttttacaa atgattaatt ggaaggtaga aattgctgat tcataacatg   100020
taacttataa acttatgatg gactacttta agcataaatt tttttttttt ttttaagaca   100080
gagtttcact ctgtcaccca ggctggagtg caatggtgcg atctcggctc actgcaacct   100140
ccatctcctg ggttcaagca attctcctgc ctcagcctcc cgaatagctg ggattacagg   100200
catgcactac cacacccagc taattttgta ttttttagtag agacagggtt tctccatgtt   100260
gatcaggctg gtctggaact cctgacctcg ggtgatccgc ccgcctcggc ctcccagagt   100320
gctgggatta caggcatgag ccactgtgcc cagcctgaaa tattttttta atctaccctg   100380
actcctcttg ctctttctga agaaaaattt ttaaaaatgt atgtaggtgc ctttaattag   100440
aaaaaaaatt aaaaattaag gcaacttgtg ctcatattgg taatagcatt tctttcaaga   100500
```

```
actcagtaat actgcattgt ctttaaagca taatatctct tagacttgac ggtttgagat   100560
tctaaatcac tgaagaacct cttgtgaaaa tgatagtttt aaaatttctt ttcaaaaata   100620
gtcctattgc aaaatgtttg attttcttga agtttcctgg aaactatatt tcattcattg   100680
taatgaattt aattttcatt aacatagatc tctaatattt ttctcagctc accacaacct   100740
ccacctcccg ggttcaagtg attctcatgc cacagcctcc cgagtagcta gaattacagg   100800
cacccacccg gctcattttt gtattttag tagagacagg gtttcaccat gttggccaga    100860
ttgatctcga actcctggct tcaggtaacc cacccaccct ggcctcccaa agtgctggga   100920
ttacaggtgt aggccaccat gcccagccag ctttttccata attcttataa atgccaatgc  100980
ctgaaatgga atctgacata taaaaaatta catgaagaac ttttattatt ttgcatttga   101040
aaaccatgaa aaatagttgg accagagtct cagaaagctt gtagtttgtt agtttaactg   101100
ctctaaatgt caggcagata caaaactatt aaaagacatg cttcaaatat gaagacaatt   101160
taaaagcaca gctgtacact tttgcttttt gtctagtttc aaggtaaaga tgaataatca   101220
tttagataat gcttaagcta tgcttatgca tacttagagc aattctccaa aataaaaaat  101280
tttaatactt aaatacatga ttaaaataga cacgtatcca atgtcaatac agactttact   101340
cagaaatagc ttttgaagtt tcttctaccc cataaataga ttttatttta tggctggcag   101400
aaatgaaaat tacaactttt tgccaagaac agagaataga ataatctcaa attggggctg   101460
cggactcagt tttatgttca aagctgtgtg aacctcatca ctgagttctt acaaatccct   101520
gtgtccacat gctccaaacc acccactgtg agttcagaaa agaactctga gtgcatcttt   101580
cagtaggaaa gtaaaaactg attttttacat ttcctttgag ccaaaccagc tgtttcttct  101640
ttaaagattt ccctttgaga tttccatttt atgactaagt ctaaccagta ttttttttggc 101700
aagtaagagt tgtgggagtg tatctgtcat cataaggaaa tcaaagccag aaatgccttc   101760
tgccatggtg ggtgatgtta aacatttcaa ggaactttat attataaaaa ttgtcaaaca   101820
taaaaggaaa agtgcaatat aatgaattcc atggacccat cacacagcat caatatttat   101880
caacatttta tcaatatttt ttcatatatt tttcccacat ccactcccac tagtgtttga   101940
aagcagaaga cagataactt accatcttac ctgttaacat ttcaggatgt atttctaaca   102000
ggtaaagact ttatcatttta atatttagac tgtgtttgtt caaattatct gattagattc   102060
tatttcagaa aacacacaca taaacaaaaa tgataatgag aaaaagaaag cccttccaca   102120
tgattgacac ttctgagtag tgtgatccca gttcatgtcc attgtctggg atagctatta   102180
aataaaactt cctctcataa aattctctcc atttagaaga taaattctgt gattcacaag   102240
cctctttttta tttataatag cccttcccct ttctttatga atttgaattt gttttttaaa  102300
gaaactgtga ttttctctgt aaaattcccc acattctgga tttggccgat tcatccttgg   102360
ttcttttgtt tactttaacc tattcctcta tccccagtat cttctgtgga ctggtagttt   102420
gactggttct ttttcttttc ttttttttt ttttttttt ttttgagac aggctctcgc      102480
tctgtcgctt aggctggagt gcagtggccc aatctcagct cactgcaacc tccacctccc   102540
aggttcaagc tattctcatg cctcagcctc ctgagtaact gggactgcaa gcatgtgcca   102600
cctcatcctg ctgattttg tactttagt agagacgggg tttcgccatg ttggccaggc    102660
tggtctggaa ctcctggcct caagtgatcc gcccaccttg gcctcccaaa gtgctgggat   102720
tacaggcatg agctatcacg cccagctgat ttttaagtaa tataagtatg tgtgcatgta   102780
tagtatacat tggcaaaaac acttcataag tagtgctaaa atcatcttat ttatatacat   102840
caggagacac ataatgtctg tttgtttccc attttagtga tattaagagt gtttagcatg   102900
```

```
tttagttgtc agcctgatcc atcattatgt tcttcatcaa actttcacca gatagtttca    102960
catcaattga tgatcattgc ctgtttctat tattttgttt tcaagttgac agttttctct    103020
cacttgatgt tgtgtaaatt tagttatata aagttaaatt attttgctat tttttctatg    103080
ctgtatacat ttgaataact gacctaattt ttactttaaa aatatttttac aattagaagt   103140
ccaaatagta aatcaaaggt taagaatttt tgcagaaatc tgttatatag atgacatttt    103200
aatatttgcc ctttatatca tttaccatga gccaaatttc aagtcatatt aaaatgactg    103260
tcatgtgcta attctaacaa tatttgaaag accectatca aaataaatat acctttttagt   103320
agccactttta ttagaaaatc aactttaagt tatttccccca tgttttttttc taattgagat 103380
ataattcaca taccataaaa tttaccettt taaagtatac aattcagttg tttcagtaca    103440
ttcacaaagc tatgcaaatg tcacctctac ctagtttcag aacgttttca tcattcccag    103500
aaggaaaccc tgtatttatt aggcagtcac ttccccttct cccettcttc cttcctctaa    103560
gtggcaacca caaataaaca ttcagtttct ctggatttac ctattctggg cattttgtat    103620
tagtgaaatc atgtatttgg cctttctctc tggcttcttt catgtacctc aatgttttca    103680
agtctcattc attttattaa aaaaaaaaag tacctttttt cttttttcttt tttttttttttt 103740
tgtccacgta tatattcaca ccacattttt tgagacagag tctcgctctg ttgcccaggc    103800
tagggtgcaa tggtgcaacc tcagctcact gcaacctctg tctcccgggt tcaagtgatt    103860
ctcatgcctc agcccccaag tagttgggat tacagttgtg caccaccaca cccagctaat    103920
ttttgtattt ttagtagaga cagggtttca ccatgttggc taggctggtc tcaaactcag    103980
cctcaagtga tccttctacc ttagcctcct aaagtgctgg gattacaagc atgagccact    104040
gtgcccagcc acattttctt tttccattta ttagttaatt gacatttgga tcgtttctac    104100
ttttttggcga ttataaatta tgctgcaatg aacatcggtg tacaagtttt tgtgtgaaca   104160
tgttttcagt taccttggga tatacaccta ggagtgacat tgttagtaat atggtaactt    104220
tatgtttaac ttttttgaaga actgccaaac tgttttccaa agtagcttta tgcttttaca   104280
tttctgccaa caatgtatga aggttccagt gtatctccac atcctcaaga aaatgttatt    104340
gtcttttttaa ttgtaaccat ccaagtgggt atgaagttta tctcgtgatt ttgatttgca   104400
ttttcctaat ggctgatatt gggcatcttt tcacgtgtgt attgaccatg tatttttttg    104460
agaaaagtct acttatatgt ttttaattgt attattttta gagttgtaag aatatgttat    104520
gttgatactt gaactttgtc aaatgcctgg tttgcagata ttttctccta tcccacaggt    104580
tgtcgcttca ctttgataat gtccttaaag tacaaaagtt ttaaattgat tttgatgaaa    104640
ctcaatttct ttttaattgg cagcttgtgc atttggggtc atatttaaga aatcattgcc    104700
tcattcaaga tctgaaagat ttacacctat gctttcttct cagagtatta aactttagt    104760
tcttacatttt agattttttaa ttaatgttga gttaatttga tggtgagaga taagagtcca  104820
acttcattcc tttgcaagta gctgtccagt tttctcagca ccatttgtta aaagactgtt    104880
ttttttcaat taactgacca agatgtatgg gtttatttct ggactcttaa ttctgttaat    104940
ctgcatgact tttcttatgc cagtaccaca ctgtgctgat tcctgtagtt ttgtagtaaa    105000
ttttgaaatc aagacaggta agtcttccaa ctttgtactt ttgcctacca tgtttcttgg   105060
gtttccatat gcattttaag atcagcttct ccgtttcctt tctggatttt tttttttttt    105120
ttttttttttt ttttttttggt ggagctggag tcttactata ttacccaagc tggttttgaa 105180
ctcctggcta aagagatcct ccctcctagg cttcccagag agctggggtt acaggcatga   105240
```

```
gccaccacat ccaacccect tctgggactt tgactggggt tctgttgaat ctgttggtca   105300
atttggagag tattgatatc ttaacattaa agcttccaat ttatgaacac aggctatttt   105360
tccatttatt cttaaatttc tttcagtaat gttttggatg aaacatgtac aaagtcctgc   105420 acttttatt tttttaaga cagagtcttg ctctgctgcc cagtccagag tgcagtgctg     105480
ccatctcagc tcactgcaac ctccacctcc gggttcaagt gattctcctg cctcagctgg   105540
aactacaggt gcgcgccacc atgcctggct aattgttttg tgttttggt ggagacaggg    105600 tttcaccatg ttggccaggc tggtctcaaa cacctggcct caagtgacct gactgccttg   105660
gcctcccaaa gtactgggat tacaggcatg agccaccacg cctggcctgt acttctgtta   105720
aaattttttc tatgtatttt ttttatccta ttgcaaaatc aaatttttg ttgataatat    105780 atggtcataa atttcatttt tatatattgg tctcatatcc taccaacttg ctgaactagc   105840
ttattagcac taacttttt tggtagattc cttaggattt gctgcataca agattatgtc    105900
atctacaagt agagatagtt ttgtttcttc acttccaatc tgggtggctt tatgtttttt   105960
tcttgcctga ttacccagtt agaacttcca gaaaatgtca ggtacaatta acaactgcaa   106020
acatccttgt cttattcatt ttagaaagaa attttagtt tttcaccatt aagtatgata    106080
ctagttgtag gttttgttta aaaaagact gtgtcaagtt cagaagttcc cttctgttgc    106140
tagtttgttg aataattta tcacgaaagg gtgttgaact tttctcaaat gctgtggcta    106200
catctaatga aatgatcatg cgttcttctc ctttattcta ttaatatggt atattatatt   106260
gattcatttt tatacattag attaacatta tatttctgga ataaatccca cttggcctca   106320
gtgtgtatta cttttatat attgctggag tctgtttgca ggtatttcat tgaggacttt    106380
cgcatctctg ttgataaggt atactgatct ttagttctct tgtgatatct ttggttttgg   106440
tgtcagagta attctgagtt cacaaaatgc attgggaaat gttcccttct ctatcttttg   106500 gaagagtta caaaggattg gtttaactct tttttaaatg tttgaggaaa ttctctaccc    106560
ctgggctttc ctttgtggga attttaaac attttaaaa tagattattt ttaaagcaat     106620
tttagggtaa aagcacattg aatgaaaggc acagagcttc cttaagtaca tgctgcccct   106680
gtatgtgcat agcctccctc attatcaaca tcctttacca gaatggtaca tttgttgcag   106740
tcaatgaacc tgcattgaca attgtcgatg aaagttcata gtttagagtt cacctttggt   106800
gttatgtatt ctgtgagtct ggatccatgt ttaatgatac tcattcacca ttacagtatc   106860
attcagagta atttcactgc cttaaaagtc ctctgtaccc tacctatttt tctctcctac   106920
cccactaacc cttagcaacc aatgatcttt ttatctcaat aattttgcct attccagaat   106980
gtcatatagt tggaatgata cagtatatgg agccttttca gactggtttt tgtcacttag   107040
taataagctt ttaaattttc caccatgtca tgatcgttca tttcttttca gcattgaata   107100
atattccatt gtctggttta tcacagttga tttatccatt cacatagtga aagacatctt   107160
agttgcttcc aagttttgac aattatgaat aaagctgtta taaaagtatg taggtttttg   107220
tgtggacaaa agttttcagc tcctttgagt aaataacaca gagcacagta gcttgattga   107280
cagtaagagt aagaaatatt ttttctcagt ctgtgtctta tttttcatt cacttgacag    107340 tgccatttgc agaacaaaca gaaagtttta attttaatga agtctaggtt atcagttaat   107400
tcatgaataa tgttttggt attgtatcta aaaagtcaac accaaggtca tctatatgtt    107460
ctgtgttatc ttccagaaat tttatagttc tgcattttac atttagggct gtgacccatt   107520
ttgcattaat tttgcaaaag ctataaagac tatgtataga ttcacttgtt tgcatgtgga   107580
gttgtccagt tgttcccgta ccatttctta aagactatct ttgctttatt gtattacctt   107640
```

```
tgctactttg tcaaagatca gttgattata attaagtggt ctgtttctgg actctttatt   107700
ctgttccatt gatatatttg tctagacttt caccaatacc acactatctt gttaacttag   107760
gctttagagt aagtcttgca atcatgtagt gtcagtcctc tgacattgtt tttctccttc   107820
agtattgagt tggctattct tttgcctatt actaagtaaa aaaagcagtc tgaaaaggct   107880
atatatacag tcatttattg gtcttttgcc tcttgatata aactttaaaa ttactttgtc   107940
agtatcctca aaatcttgca ggaattttga tagattgcac tgcatttcta gattgagtta   108000
gaaatactgc catcttgaca atacacatct tcctatccat gaacatggaa catctctttc   108060
ttggatatcc ttcattagaa tttttgcattt tccccatata gaccatgtac atattagatt   108120
tatacataaa tatttcattt ggggggggtgc taatggtaat gtatttttat ctcagattct   108180
gcttgtacat tgctggtatg cagaaaagtg atcaactttt gtatattaaa cttgtttcct   108240
gcaaccatgt tatataatca ctttagatcc agtttttttt tttttggtca ttctttcata   108300
ttttctaggt gatcatgtca tctagcaaag acaacttctt tctaatctgt atacctttta   108360
ttttcttgtc ttaatgtatt agctagcatt tccagtatga tgttgaaagg cattggtgag   108420
aggcaacata cttgccttgt tcctgatctc agcaggaaat cttcaatttt atgttagctc   108480
tatggttttg tagatattct ttatttacat taaatatgtt agctgtatgg ttttgtatat   108540
attctttatc aggttcaggt agttcccctc ttttcctagt ttactgagag cttttgaaa    108600 atcattaatc agtgttggat tttgtaaata cttttttttcc acctattgat attaccatat   108660 gattttttctt tagcttatta acgaaatgga ttacattaat tgattttcaa attttgaact   108720
agactggcat acctggagca aatcccacat ggttgtgata cattatttat gaatgcattc   108780
atggtcatgg ttgctattag tctgtagtta tcttttattg taaagacttt ggtgttggta   108840
ttaaggtaat gctgccctca tagaataagt tatgaagtat tttctctgct tctgtcttaa   108900
ttgagattgt agagaattca tataatttct tccttaaaac tttggtagaa atcagaatga   108960
accatctgtg tctggtactt tgttttgaaa agttattgct gattcaattt ctttcataga   109020
tataggccta tttagattat tattttgcat aaatattggt agttgtgtcc ttcaaggaat   109080
tggtccattt caccttgatt attaaatgtg tgggcacatt tgttcataat atttctttat   109140
tatcctttgt ttttgagaca gggtctcact ctggttgccc aggctggagt gcagtagtat   109200
gatctcagct cactgcagcc ttgacttcct gggctcaagt gatttaccca cctcagcctc   109260
ccaagtagct cggactacag gcacatgcca ccatgcctgg ctaattttttt tattattatt   109320 agagatggag ttttcctatg ttgcccagtg tggtcttgaa ctcctggact caagcaatct   109380
gcctgcctca gcctccaaag agtgatggga ttgcaggcat gagccatcac acctagcctg   109440
atggcagaac tttttaggaa caatagaatg gtatatggca ttttcaaaaa ttgttttccc   109500
ctcctcctat ggaagcatga agggattttt ctctagtatt cattgtgaga acctcatctg   109560
gctcctgaat gtagaaaact cacaaaactg tgaggaacct attatgactg gatgcctttg   109620
gagttgttca cactgaacct ccagcaattc atcaattata tttcagattt tcctatccca   109680
acactggttc ctacagaggt ttctgctcca gtaagctgta attcttttta tccatctgct   109740
tccttggttg tgagggcagt gattttccct gtgacctcat ttctctgaca gatctaagta   109800
gtcttgatta catcttttaa cctgttgtag gtatattcag attttctatt tcttcttcag   109860
tcaattttag tagtttgtgt ttttctagaa gtttgttctc tagctctgct ttagctccat   109920
ccaataaaat atgagtatgt cgagttttca tttacaacaa ggtatttttct aatttctatc   109980
```

```
atgttttttt gattcctgac tgtataggag tatatttta cctattaccc aaatttgctt    110040
gttattcatg tataatttta tcagaaaaca cactttgcac aattttttgca gtgttacatt   110100 tatttagact tgttttataa cttgacatac agtccatcct ggagaatgtt tcacgtgtgc   110160
ttgagaagaa tgtgtatatt cagctgttgg tgggtggcat gttttataga tgtctgttag   110220
acctagttgg tttatagtgt tttttacaac ttctgttttc tttttaatct tctatctact   110280
tttagccatt attgaaagtg gattagtaaa ttatctattt attcctttaa ttctgccatt   110340
ttttgcttca tgtattttgg tgctctgttg cttattacat gtatgtttac atttgttaca   110400
tcattttaat ggcttgaact ttttattata aaatgtgtat atcttgtaga tatcgtatag   110460
ttaaatcttt ttaaaaattg atattgctag tctttgcctt ttaattttttc aatttatata   110520 catttaacat aattattgat aaggtaggat ttgtctgcca ttttgtctgt atcttgtctt   110580
tttttgtgtt caatagatat tttctagtgt actgttttaa ttcccttgtc ttttactaaa   110640 tttttgatg ttcttaatgg tttccctggg gattacaact aacttataac agctagtctg   110700
aagtaatacc aatttcatta caatataagg aaactttgtt cccatatagc tacattccct   110760 cttttactc tgtgctatta tacaaattac attttatttt atgcccatta acacagatta   110820
tgttttttct tttaaatcag attgatattg tcatttaaat caaatatgag aaaaatagtt   110880
acaaaaaaat acatatatga tttcatattt acctatgtaa ttatctttac tggtgctctt   110940
taagttctta ggtgtatttg aggtactgtc tagtgtcctt tccttcagc ctgaagtata    111000 catttagtat tttttgtagg acatgcctga aaacaataaa ctcttattta tcagagaatg   111060
tcctaattta ttatataata catttctgaa agatagtttt gcaaaataca gaattcttgg   111120
ttggcagtct ttttcttgtg gttctatgtc attctactgc cttctggtct tcattgtttc   111180
tgatcagaga tcagctatta atcttattgg gaatcctgca tacatgataa tcatacagtt   111240
ttcatgattt tcttgtgttg gctttcagca gtttggttat gatgtttata tgtatgcata   111300 tctttggggtt tatgttacat ggagttagtt gagcttcttg gacatgtaga ttgatgttgt   111360
tcatcaaatt tgagaagttt tcggccatta ttttttcaaat attcttccta ttctttattc   111420
ttcatcctct actttgggga cctgcattat gtctatgttg gtatgcttta tggtcttcca   111480
cagatctctg aggttctgtt tatgttttca ttttttcagac tgaataatct caattgactt   111540
atcttcaagt ccctttttcc cctccttttc aactctgcta ttgaacccct ctaatttttta  111600 ctgcagttat tacactttca gctttagaat tctatttaat aatatctttt tcttgagttt   111660
atctcatgta tttaataaaa tgctgtagtc ttactttagt tatttaaata cagttttctt   111720
tcattatttg ggcatacatg aaatagctga cttaaagtct ttgtccagtg gcctaacatc   111780
tggacttttt caggaatagc ctctattgac tactttatag gggccatact ttgtttctgt   111840
ttctcttaat tgtttagaca ttttaaacta atgtaatggc tgagagcagt ggctcgtgcc   111900
tgtaatccca gcacgttgag aggccaaagc aggagcatca cttaagccca ggagttcaag   111960
actagcctgg gcagcatagt gagaccctgt ctctacaaaa ataaaaataa ataaataat   112020 ataatctggt aaatctgaaa atcagattct accccctgcc cagaatatgt tactgtttct   112080
ggtggttgtt gttatttct ttttaactac tcctataaag tttgtattgt ttctcataga    112140
tagccatcga agtctttgct tggttaactt agaggtcagc taaggattag acagaattcc   112200
ttaggtgcct gagatcaata agtcagtctt tgacaaaggg gtctgtatgt gtgttggggc   112260
atgcattcaa cactcagcca ggctatttgc agctctggat tagcctttat tccctgcttg   112320
tgcagagtct caaggttaga ctgtggtgag agtttagggc tttctgaggt cttttgtggg   112380
```

```
ccctacagtt gcatgtggct ttctaaattc ccaggaatat attttcaaag cctcctgtgg    112440
atcatctcat ttcccaggta atttactttt aagcttttt agttatctta tgttttgctc    112500
cagttattag ctacacctga gtcagtgaca atattcaaca gctgcctatg attatttgac    112560
aaatgcctct gtggaaaagg tggttcacac taggtgaact ccaagttaga taagtaaag    112620 ataaccttac tagtgggatc ttccaggaaa ctaccaaaca ggtcaaataa tgtaaggtct    112680
ctgtgaatgg gactttagag tatatccaac cagtctagag tatatccaac caatctggcc    112740
tcctctagtg gcagcctggc tgctgctttt cataataaat gtgggctgtt ttgatttgaa    112800
ggctaccata gagctgtggg gaaagttaaa ataccacaga gctcactctt ctcactgaaa    112860
tcctgtcttt ttttcccttg aacaaattct ccctatattg ctgcaagctt tttgctaatt    112920
tccagatctg aaaaagctga ttctgacaat atttatcagt acttttattg cttttatgga    112980
ggataaaatt ttcagagatc cttattctgc cattttgct gacatgtgta aagtgatcat    113040
ttctaattgt aaaattcctt ttgcatttat tagctggaat actttacagg acttttcctc    113100
atcaaccgtt agttaccatt taatatagtt tgtaagaatg atagaataaa tgcatggcaa    113160
gaatctttac ttctcaaatt tcagagattt tgatgggaaa ttatatttag agatcacaat    113220
cagtgtctag atgtgctccc tgctatggag gtgtcattac ttttaggctt ttttaatggg    113280
caaatacatg aagtaattat tttttagaaa gaaaatctga gattaactca atcattaat    113340 tcatactgat ttttcctatt catagttgac agagtattat tatcttttgt tctgcttctc    113400
ttgtacactg aaattcttgg ttttgatat taacaattat ttacttatat cacaatatac    113460
atacattaat ttaaaaataa tttacagtgc tacctgaata ttttttcttg taagttgttt    113520
tatctctctt tgcttacttg tatgtttgtt tattgtcatt agaatgtatc aaactagggc    113580
tataaagctg taatactata ttttagccag aaactaggac ctagcactca aatgcccatc    113640
aatggtagaa taattcatca cattttata agatggaata tggtactcaa tgaaaatgaa    113700
taaagtacaa ctacatgcag tgatttggat ggatatccca aacataatgg aaaaagcaca    113760
cacaaataag cttatattat ataattccat ataccatgt atatatcaag tataaaagta    113820
ggcaaaacaa gctactgatg gtggcacaca cctatagttc cagctatttg ggaggctgag    113880
gcgggaagat cacttgagcc cagaagttca ggttcaacct gagcaacata gcaagacccc    113940
atctgtaaaa aagaaagcat tattaacata aaaataggca gaactactat attcttagag    114000
aagttactgt tagggagaca gacagtgagt gactgaaagg caaaatgagg ggaaattcca    114060
ggggatagta aatattttgt ttcttagtgt gggttctact taactgggta ttttccattt    114120
gtaaactgta aaattatgtg cactttctg tatgtgtatt acattgcaat aaaattgttt    114180
aaaagtcaat tgaaatagtt ctgtgtgtgg ttatgccaca gcttaataca gagttagatt    114240
agacttcttt tcaaactcat tttgcatata gacacctata atatcagctg cacagcctat    114300
ataatgctat ccatagcaat gaatttggtc ttttgatttt tcaggagaac ttgcgcctgt    114360
caggggctgg atccagaaac ctgtggtgcc tccttctctt ttggttgttc atggagcatg    114420
tactacaatg gatgtaagtt tgccagaagc aagatcccaa ggaagtttaa gctgcttggg    114480
gatgacccaa aagaggtttg tttacttcct gatgtataat cgctttattt ttcatagaga    114540
attcattagc ttagatgaag tgaacaatat gacatatctt ggtaagctct tattaatcaa    114600 agttttccc aaactgtaga tacacactat ttttaagtt ggcataataa tcatatttatg    114660 ccaaaataat agataaaatt tgagcaacaa aaacttcctc tttggtcttt tatgttaatt    114720
```

```
ccaaagttttt aaagggggtgt cacttcattg ttaaaactaa atgagaattg gtgatgtttt   114780
tcatattttg actctgaatt atggaagtta cataagtact acattcagaa aagaccattt   114840
ttagtcacat ttatgtgcaa tgagattcaa ataatttaaa gtcactgtaa tgaatgcatt   114900
taataaagtc actgtaatga atgcatttaa gtaactaaaa catttagatt ttaatataac   114960
tctgtaatgg aaataaatgg acactaattt ctcactgaag tcattggttt ttgtcttgtc   115020
tgtagaatac gtatttctta taatttgcaa attgataaat ttacaaactt tgggtggca    115080 tgtagtctag agtatagata cttcttgact tatgaggaga ctacattcct ataaatccgt   115140
tgtaaaatga aaatccattt aataccccca ataaacccat cctaaagtaa aaaaaaaacg   115200
aagccattat aggtcaggga ctgtctccgt actaattgaa tgatgagaaa acctcagtat   115260
atttagcatt tagctatgac cacattttca gtcattctat acacttacaa ttatcttttg   115320
aatttcgaat acaattaaaa tatttccata ctatagatat tataacattg atgagtccct   115380
ttaaatgaag aatttgttaa ccttattaag ctttcactta ctattatagt cacagttaat   115440
aaagcaagtg caaaaactcc tgaaatcaca gtataagttt tttaaaggat gttttcaata   115500
attaaagttt acttaaatgt gcgagacatc atttcataag acaagaatat gaatattaat   115560
aacttaatga aaagtactga ttttgcttgc tgtcattta  attttctaca gataactttt    115620 tttttaaccca ctgttttatc aagtgataaa tgtttatcac tttcacgagg tttcatgtaa  115680
accaaatcca gaggatacca agtaacttat tgcctctgtt gggtaggaga gctctgttca   115740
gaaacctcct caccttctaa aatttacatc tctgccaggt ggttatgtct cacaactttt   115800 ttttttttaga gaaatatcaa tctgaaatga agacttctaa gtataaatgg agcagctaaa   115860
tatgatcacc taccattttt taacagtata ttacttggaa aatctgttct tcatgagcag   115920
ggcaggtggg ggtgtaactg agcatttccc cttttcaagta aattctgcaa aggttttcat   115980
gtatcctgca ttctagttct gaagcatttt atccatattt gaagtgtcca gtaaatttta   116040
gttgctctat ggagagatca ttccaaatta tttaaatact atctttataa acataaaatg   116100
taaagattag aaatagacaa attaagctaa agaagttctt ttaatagttc atcttccttg   116160
gtagctaaaa aatgtgaccct ctttaagacc atacggctta attccctaa ccctactcct    116220 ggcacaggct tgtgtgtata aaatgcaaaa tatctgcatg cagttagaaa atcaatctta   116280
tgaaaaaaac aaatagctag atatttacta gcacatatga aattaaatga tagtcatgtt   116340
ttaaagatgc tttatttagt aataaaggca ccatatattg tgtttgggat tcaaaatgta   116400 agggggaataa tctaactgat agtctctttt acatagagaa aatggactta gaattaata   116460 tgtagaatta ttcactttat acaggaagag aaactggagt ctcatttgca aaacctgtcc   116520
actcttatgg caccaacata taagaaactt gcacctgatg catataataa tcaggtaagt   116580
ttaaataatc attggcagca attgtaacaa cttacttgtt actaatgacc tatgtccaaa   116640 aatattttttg aaacaatgat ttttaaatat tattctaact tttcctctta attgttgaaa  116700
ccactgcagt gttcagtttc gagtatataa aaattatacc atacaaaagt acattttttt   116760
tgtcttttag ctgtaaagac atgcgcttct aaaagtcaca ggctgttcta tctactaatc   116820
ttgttctcat atgaataatt ttgtttctgt aaacagacta tggagattac atcaaaatta   116880
tgtggcccaa gctataggtt ctaactacct attttttactg caagtctata agtataaatg   116940
agtattcata agaatttata gacttacaaa tattcacata aagctatgca tatactaaca   117000
ttgtaagtat atatatttcg gtccagatgt gtcagatttt gctgatcttc ctttttgtt    117060 tgaccttgac ttcatacacc aagcaaaaac attttttttt tctatttttac atgtgtattc   117120
```

```
taaactatag ctagttaaga caggtagatg atttggtcag aaatctctca tcatgaaggc   117180
aaaaaactaa aatcttcact gtttcagtaa catcaacaac aaaagcatta agtgaaagtc   117240
tattacaaac taaacactgt gtttagtcac tgggaacata aaggtgagca gtgccatctc   117300
tgtctgtctt taagaattcc gtctttgctg ggtacggtgg ctcacacctt taatcccaac   117360
actttgggag gccaaggcag gtggatcacc tgaggtcagg agttctagac cagcctgatc   117420
aacatggaga aaccctgtct ctactaaaaa tacaaaatta gctgggtgtg gtggcaggca   117480
cctgtaatcc cagctactcg gaaggctaag gcaggagaat agcttgaacc tgggaggtgg   117540
aggttgcagt gagccgaagt caaaccattg cactccagcc taggcaacaa gagcgaaact   117600
ccatctcaaa aaaaaaaaaa aattcatctt taactgggtg cggtagttta tgcctgtaat   117660
cccagctacc caggagacca ggagtctgag gctgcggtga gccatgattg catcactgtg   117720
ctccatcctg ggtgacaaag atgacccaga ttctaaaaaa aaagcaaaaa acaaaagaat   117780
tccttcttta gtggagacag agacatataa aataaatagc aatttagaa ttacacagtt    117840 ccagctggaa tagaagaatg tgcacatttc taaaaaaatt taaaaacaaa acccaaaagt   117900
agactagatg tcacaagcag ccttagacgc taaataaaga tctttgaact ttattctgta   117960
ggtaaccatt gggctgtttc aagtgtgtgt tggggatgga agggtaaagt gatgtaattc   118020
gtattttgaa aaatttactt aaaagccaag taagggaaat ataacttaaa tctatgtaag   118080
attagagaga gaagaaagct attgcaatca ttgggcaaga gattttaagg acctaaagaa   118140
atggcaggaa ttaagtatgt acactaacta aggtggagct tagagaactt ggtgactaga   118200
tgtatggatg agaaaagaat ttggagatac aacaaatttc cagtttggac aggtagttct   118260
attaactagt atcagaaatt ggtaagaaat agtaagtttt gggatgggga gaagatatca   118320
aaattttgga catgctaggc ttctaggtta attagatgga gaatcaggag aaaaattcag   118380
gctagcactg tagatttgag agtcagaatg ctggcaggac ttaaagttga atacatagga   118440
atgaaaggag gttttcaaag tagagattat aaagaggaca aagggctgat gatgggattc   118500
tggagccatc aatcatttta ggcatgagtg gaggaagaga agccaatgaa gtaagaactg   118560
ggggagggag tagaagaaat gtagtaggaa aagtgaaaga gggagatgga tggatggagg   118620
aaagctggaa tgatgagaag acacccagag cagagtatac aggagcaata ggtatggggc   118680
tctgggatgg gtgctctgtc atttacttga taatattaaa gactctcgtg ggattagatt   118740
agtttacaca gcagacatgg acaagggact aatcctaaaa tgatttagct actcttcttt   118800
tccactgtgg actttaacgt cccaaacatt tttttttttt tttggttcga acaatagagg   118860
caaattaaac gatggtctat ttgtaagtta ttttatgtca aattatgttt ttagaaatgt   118920
gtatgaatat ctatgaaaag ttttttaaaca ctattaatag ttggattaat actgttattt   118980
tgtttagcta gtatcacaaa gtataaggag tgctttgata ctgtcgtaaa agtttaattc   119040
tcagcaagaa cttctgaaat aaatcaagct ataaaaataa ataatgaat gagtctatgt    119100 tgctagattt aaagttgggt catttttctat taaatgaatt tttaataggt gctgttaatc   119160
aaatggcttt acttgaggca gaataacaaa gcattgatgt tcttttttgct cccttgattc   119220 ttattatgga ccgtctcata cttgaaacta ttttatacat ttcctaaaac ttaagtaccc   119280
aaaatatgaa gccatcaaat atgttcaagt tttaatattt atatatgaaa atgtgttgat   119340
gtaatgtcta gataaaattaa gtcaattaat agttgtaaat ggatgagatg cttctgaatg   119400
gataaaatat ttttatattg catggtaggt actattggta atattcatcc atgtatgtta   119460
```

```
atatgcttta gagatcaaaa taatagccat gtgatgtttc cacacagtac acgggaagac   119520
catttgatgt tatagatgct gtcataaaac ctactatttg atctttacct cctttcccca   119580
actgagtgtc gtatctctat ttctcacatc tgaatattct tccttgcttt attccttgat   119640
ttcatgaagt cttattgcta aagtttagtt ggctctccac agcatctctt ctgtcagtcc   119700
catggaatta gagcttcagt tttctcaact taaatgtcct ttcttcgtgt ctatccagta   119760
gacatatatt tggctctgtc ttttctatgc ctgccttaca atttaacagt agacctgaaa   119820
tagcaggtgt caatctcaaa atcgtgtgct atttatcata catgaagatg acattttaga   119880
caaatgcttc taagagagct ttctatgaag atggaaatat tctctattta tgctgttcag   119940
tgtaataggc actagccaca tgtggttatt atttaacagt tgatacgtgg ctagtgtaat   120000
tgagtttaaa ttaatgtaaa aattaacaca aacagccaca tgtggataat ggttaccata   120060
gtgaacagca caaccttaga ccatgagaaa gttatgcatt tagaattgtc ttccagacat   120120
ttagatggat ttccagtaat tcattcacaa aatcctgcat ggtattttt aggagatggc   120180 ataagtgtaa tttctagctg attgtatatc tgttttttgtt caagaaacag aataaagcta   120240
actagaccac agcatgaact gaacggccac aaagcacaca tctatgttaa agagtagttg   120300
gtaccttcat tttcctttgg ccaaagtttt atgaggttag atagacaaat acatatatga   120360
atccaacagt aaataatatg aagccaccac aaactttat cctaatgcaa gttcatcttc   120420
tagccatgat ggagtaaaca gagactacat atgccgttac acatttaaga aaaaactgac   120480
aaaatatatg aaacaatggt ttttagacat agaataagaa attcaagaga cagtggcacc   120540
agagagaaag gaagtaaaaa ggtgaaccta taaataccc agtttacttc ctgaagagag    120600
tattaggctc cagtgtagcc agtaggaacc caaacacacc cagccttatc tctgtattaa   120660
ggagacaaag ttcaaaattt ggagaggcca aggtgacgag agttcactat tcagaatatc   120720
agagaggaga gagtgttatt gagaaaagct ccagagacct gcagagggtt ctgatccagt   120780
cttcagctga gtattaaaca gcacatgcat gtgaaaaaac tgccaaggct aggtagggaa   120840
agaaccatca gaagaagcag gcagaataat cccttgatct cacacaggac ctggaatagt   120900
tcttgatcat accagccaga cggagaagac ttcataatac tattcataat tgtattgcct   120960
tggtagtaga agtaaattgg gcagttctga cctcatctaa aaatgcttaa aatgaaaaca   121020
tagaagggcc aaactgattc taagtaattt aactgcatca cagtacaaaa attaaaaaaa   121080
aaatctacca acaaggtaaa atttatagtc tagcattcca tcagaaaata caaggcatac   121140
aaagaaaaaa gaaaatataa cctttactgg ggaacaggca gaaatcaatc aataaaaata   121200
gtcccagaac tgacatatgt gatacaatat gtaaataagt tcattaaaat ggctatcata   121260
tttcatatgt taaatgcca gaggaaagca tgagagtgat aaggaaagat cagaagatat   121320
taaaataccc tacaatgacc ttctagaagt gaaaaatata tatctagatt aaaaatacac   121380
taggcggaat taacagatta aggaacttga agacatagta atagaaattt ttcagtataa   121440
agaaaaaact gaaaaaaatg aatatataaa agacctatta gccaatattg ttacactaat   121500
atatgtgtaa ttggagtacc agaaggaggt gggagacaga aaaatattta agaaacaat   121560 ggccaaattt ttttcagatt tgttcaaaac tgtgaaccca cagatctcag cagctcagca   121620
aaccccagat taaaaaacaa agacataaaa aaagactatc aaaaatttat aatcaacttg   121680
cttacaatct gtgataaaga gaaactcaga aaggcaaatg gagaaaaaag gacatattac   121740
actaggtggg aaaaaataag acaggagact tcattcagaa aaaggcaaga gagaagatgt   121800
aagagaaaca tcttttaacat actaaaagaa aaaagactct ccacccagaa atatataacc   121860
```

```
aatgaaaaca actctcaaaa aagacagcaa aataaagaat atttttttcag acatacatac   121920 aaaagctgaa agaattcacc accaacaaac tagcactttta aaaatgttaa acgaaatcct   121980
tcaggaagaa agaacatgat accagacaga aatccagatc aacataatga aatgaacagt   122040
atcaaaaata gtaaacatgg ttaaaagact tttaaaaaaa tgataacttg ctatcttaaa   122100
aatatattaa caatgtatta tgaggtttat aacacgtaga agtagcacag aggctgagga   122160
attgaaagta tattattgta aagtacttat acgatatgtg gactgggtat attacttggc   122220
tgtaaactgt gagacgttag agtacactgt gtaccttaaa ccactaaaaa aaaaaaaaaa   122280
agtatatagc taatcagcca gtaaagacag aaaaatgaaa tcaatccaaa aatgttttta   122340
aaaatatata ggaccaaaaa aagataaata taaaaataaa acaaatagca agatggttta   122400
tttaaaccca actgtatcaa caaccacatt aaatgtaaat ggttttaaca cccctaatta   122460
taaggcagag cttgtgatat tgaaaaaaaa gcaaaaacca agaaaccac tttaaatata   122520 aagatacaaa taaattaaaa agatatttttt aacataaaaa atgatgttga aaagacataa   122580
caggaaaaaa tatgattatt gcagtaggta cagaaaaacc atttgataat attcaacatt   122640
cataaaagga aactttctca acctattaaa tacataaatg gaaagccaaa agctaatgct   122700
atacttagtg gtgaaagact aatacttgac ccctaagata aggaacaaga caacaatgtc   122760 cattttttaac caactgcttc tattcaacat caaactgtaa attttagaaa gtgcagtaag   122820
gcaataaata aagcagtcaa gattgggtag gaaaaaataa aactgtactt atttgcagat   122880
gacatgtttg tctacataag aagtctcaaa aaatctacca gaaatgaaa ttaatatatg   122940 aatttagcaa agttgtgaaa tacaaaattc aagtgtattt ttatatacta gcaataaata   123000
aatcaaaata aaccattaaa atagcatcaa aatataaaat tcttagacat acatttgaca   123060
aaaatgtata agattatata ctggaaacta aaacattgct gagataaatt atagaaaact   123120
tcagtaactg gagagataca ctatgttaat ggatcaaaag actaaatatt attaagatgt   123180
cagttctccc caaactaatc aatatgttca atacatgatg tttcaaaacc ccagcaggtt   123240
ttttgaaaga attggacaag atggctgtaa aatatatata cttggaaatg caaaggactt   123300
ggaatagtca aataatattt taaaataagg gcagaatttg agactatata ttgcatggtt   123360
ttcagattta ctgaaatcta taattgctac tgtctgtcaa gacagtttga tattgcccag   123420
gcgcagtggc tcacgcctgt aattccagca ctttcggagg ccgaggtggg tggatcactt   123480
gaggccagga gttttgagac cagcctggcc aacatggcaa aactctatct ctaataaaaa   123540
tacaaaaaat tactggggca tggtggcgcg tgcttatagt cccagctgct tgggaggttg   123600
aggcctgaga atcgcttgaa tccaggaggc agaggttgca gtgagcccag atcgtgccac   123660
tgcactccag cctgggtgac agagtgggac tctgtctcaa taaataaata aaatttttaa   123720
aaagtttgat attgacatac ctacatacac accattatac acaagtggat cagaatagag   123780
aatccttaag tagacccaac atatataata tggtcaattg atttttaaca aagatgattc   123840
aattgggaag ggataaccat tttatccagt agtatctgaa cagttggaaa gccataaggg   123900
aaaaaaggta atcttgaccc ttaatttcac accattttata aaaattaact ccaaataaat   123960
ccatttatat gaaattctag aaaatgaaaa tctgtagtga tagattagta gttgtctgag   124020
aacaaagcag gaagcatgaa ttatacaggg gcatgaggaa atttttaaga gtaatgaata   124080
tgtactttat tttggttgtg acaaatatat atcaaaactc aaatagcata ctttatggcc   124140
tcaataacac tataaaataa aaattttacc atgtcaagat atttgctcta ttttgtgtca   124200
```

```
ttccattttg tttctggata tatatttaag ttcaaaacat ttttttaaag ttctaaatgg   124260
tctaaatact agtgagtttt cggtgtaaga gtaaaactaa ctactttcgc attcacacac   124320
acttttattt ttcagattga atatgaacac agagcaccag agtgccgtct gggtctgaag   124380
gaaggccgtc cattctcagg ggtcactgca tgtttggact tctgtgctca tgcccacaga   124440
gacttgcaca acatgcagaa tggcagcaca ttggtaagtt gggctgagga cagcttagca   124500
gctgttgagt ctgttctcac actgctaata aagacatatg caagactggg taatttataa   124560
aggaaagaga tttaattgac tcacagttcc acatggctgt ggaggcctca caatcatagc   124620
tgaaggcaaa tgaggagcaa agtcacatct tacatggcgg caggcaagag aacatgtgca   124680
ggggaactcc cctttataaa atcatcagat ctcatgagac ttactctcct gagaacagca   124740
tgggaaagat ctgcccccat gattcaatta cctcccactg ggtccttccc aaaacacatg   124800
ggaattttgg gagctacaat tcaagatgag atttaggtag ggacacagcc agaccatatc   124860
agcagcatct catgttgagg agcagaacac tggaatttag tagcattcgg ttagagtaat   124920
atgttgtctg caggtttcac tggacagcaa tattttcatg aatgaattcc tgttgcaaag   124980
tgacctgctt tggcataact agcactctca tgataggttg gcacattagt ttcctgtcaa   125040
ttgtgttgac aagcacatga gaatcatgga atccttggt  gttaatctaa accagtgact   125100
atgcattgcc agttacagtt aacttccagg aaaatctcaa aattcagtgc cagttacctg   125160
gtagattgta atcagttaag caaaaagcca atacaagcc  attcaccta  cagagagaga   125220 agcatattca ccttacagag agagaagcat aaatgagaaa cacatcatca ttgtcacagt   125280
aactgtggta acctattgta aaagattcac agtgcaaaag agcctgacta catattacag   125340
tgggtaaaat ggatcggtct tgtaattgga ggcagtggtg aggggaaaat agatacatgt   125400
tatatatata tatatatata tatatgttct ataccaacaa agggttcagg gtataatttt   125460
gcatgtaaag gggtgaccca gagtagagat aaagaacaaa atattctgtt gaaaaaacta   125520
tgaatcaatc aacctaatga attatcaaca tggatgtagg tgtagttgaa gaagatggtc   125580
agtgagaata tggaaacaga tatcaggaat taaagtcata ttctagggca gaaaagcatt   125640
catggaggta ttagatgata gctgaagtaa tttgaagaag ctggtgtgaa gttttgttg    125700 agaagcagag aagatattaa tttaatgttc tagatcagag attggaaaac tcttctctat   125760
aaagggcaag atggtaaata ttttagggac tgcaggccac ataggatttc tgtcacattg   125820
tttggtgggg ttttttttgtt tatttgttt  tttaaaaact ccttgaaaat gtaaaaacca   125880
ttcttagttt actggccata caaacacaag ctgtgaggca cattagccgt aggttctggt   125940
ttcctaactt ctgatccaga agaacaaaca caaggcctac caaccacccc aacatctaaa   126000
atcatcacta atcatgtact cagcacctgc tcattattag gaggctatgc tagtttctga   126060
aaagcagaag tagtaaatga taactggggc tatagtgcat cctaatataa ccatgtttca   126120
ttccaggaag gtgacagaga gtaagatgat gagaaggatg tttagaatca agaagaattt   126180
gcctctgata gagcatgggt tctgtgaagt aaaatggaaa ggagcactag ataagaactg   126240
aatagggtta aatatgtatg ggaaaagtaa caaggtgctc agagacatga atttgaagac   126300
ttctgtgcag aaagtgacag gctcattaat accatctcat gttgaagtta tttctaaagt   126360
cagtccattg tgatcacatt tctctcaaga atatcttcta attttatttt agatcacatt   126420
agatcacatt gtctccattg atcaaaaaca ctaaatacta aaagttagt  atttaaaaac   126480 cacaaataat cttttaccaa agctagtgta attgtagtaa ctaaagcaaa aagtaccatt   126540
taattatcaa agcaacagag gtagcttttcc tccctccacc ccttacccctt ttcagagtac   126600
```

```
ccacttatat ggtcatattt cagaaaagaa atgaagaaaa gagaaagtta ggtttgacag   126660
agtacaaagg aggagagaca agagagtgaa aatagtatta agttgcatat tacctgtatc   126720
agccaaatct ttaccttttc atttttttata tttttacttc agttatctta tggaaatttc   126780
ttaaacagag agagttaggt gtcaggtatg tgaaaagaca tgaaatttgt gttcagaagt   126840
atgagatgag gcaaatgtga tactaccaaa aacagaggaa gtcatttcgt agaaaaaact   126900
tttagcctgt ttttgaagag gcttcacatc tagcacatct attttttgaag tgtgaaaagc   126960 aagagagtgc ttcattttgg gggagtgttg cttcttccca tagacagaaa catatgtgaa   127020
gaacaagggt caccacagct aactgttcct gatagactca gagaaagggt gggtgggcaa   127080
tgtcaatttg tcttatctcc ctgtaccatt ttgttgctat tttcattaat aacaggtagg   127140
atggttttat ggtaatatat atgtcactga tctggatcaa ctaggccacc aacacaaatc   127200
tgaatactga gaggagaaag atacacacac acacacacgt tttctttggg acctgtagtt   127260
gaggctgtaa tgtcttactt ccctaccagg tatgcactct cactagagaa gacaatcgag   127320
aatttggagg aaaacctgag gatgagcagc ttcacgttct gcctttatac aaagtctctg   127380
acgtggatga gtttgggagt gtggaagctc aggaggagaa aaaacggagt ggtgccattc   127440
aggtactgag ttcttttcgg cgaaaagtca ggatgttagc agagccagtc aagacttgcc   127500
gacaaaggaa actagaagcc aagaaagctg cagctgaaaa gctttcctcc ctggagaaca   127560
gctcaaataa aaatgaaaag gaaaagtcag ccccatcacg tacaaaacaa actgaaaacg   127620
caagccaggc taaacagttg gcaggtaaat ttaatgtaaa gcatttgtag ataaatgtgt   127680
tgtgtggtat attaaaaatg aaaattattt tggttttgcc cccatcaact tgtaagttct   127740
ggggtacaca tgcaggatgt gcaggtttgt tatacaggta acatgtgcc atggtgattt   127800 gctgcacaga tcaacccatt acctaggtat taagcccagc atcttcctga tgcacccta   127860 ccaataggcg ccagtgtgtg ttgtccccac tcccccacca tgtgtccatg tgctcttatt   127920
gtaaaatgaa cattgttaat tttggaaagt tatatcaatc atggtcttag ttctgtgcca   127980
gagtcttctc taaagtagca agggccaggc tttgttctca gagatggtaa tgagatattg   128040
caccatcaac atggaaaaca tggaaaagtc tggattttat tctataataa acagcaactt   128100
tttttaacag gtaagtgata cgatgaaatt cattgtaatt tggcagtagg ccaaattagt   128160
agaggagcta atagtttgga gataaacaca gtaaaccaga actgaggtaa caagaccttg   128220
aattttgttg gttagtagca aagatatagc aaaatgatgc aaatgagctc ttccaaaatg   128280
ggaaaaagaa aatacattgg tgacaaaaca ctggaatgaa agaagagaaa agtttaaaga   128340
tgaccccaaa gttttaaacc taaacttaac ctactgtttt aggtttctaa aacagtacta   128400
tttattgaaa taagtaagtt tgaaaatatg attgagagag agagagggga gaatgaaaca   128460
tttttcctta gacatgttga gtctgtggtt taggaggggt tctacatgta gattatgcta   128520
caaaactttt acccatcaaa atagattaca gctgtagtaa taacaataga acattattca   128580
tgaatactaa gttattgtct ttccatagcc tcctgcttta tgtctgcagt ttgtaaaaag   128640
aaaaaaaatc caaatttggg gatggtattg gcctggccat taacaaaagc aaaccagttt   128700
gcttaaaact agccatcttt gctgcttcat gaagtcaaat ttctctactg attcatttcc   128760
aagctcagag gaactaagtt aaataattta gaatatgcta aagatgcttg ataagtgttt   128820
attgactggt tgacttaaca ctaagtaaat actgttcact taggttagct gtgaaatata   128880
attagataga accttgtctc tgctcccttt taactggctt ctgcaggtaa taatcccttc   128940
```

```
tgttctcaga actgccattg cagtttcatc tatttgttct taactcatat gactttttaa   129000
agtgaggtca aaacagaagt atgacttttta aaagtttcat ttacaaagct gaaagtttct   129060
ttaaagtgtt atctacaact gtgttaactt cctttctgga aagcctgctt ataaagtagc   129120
acttgttgat tatataagat gcttttttgtg tttaaatacg tgtcattctt ttttttcaca   129180
acattcccga atcttacata ataaatctta ttttaattat ttagcaaatt ccattgcatg   129240
ccaggcaatg aagaagtaag taaaataaaa cattttcctt cccatttagg aatttactta   129300
ccagtggggg tgaagagagg gctaaaaaca taactataat acattgtgag tattgcttta   129360
tcagatctat cttttgcagtt gagtattaca aaagcactag aagatgaggt caaagcggtc   129420
ccttgaggaa gggatgacta caccaaggaa ggatagggag agagggagga aaagggaggc   129480
acttcaagca gaggcatgtt cagaagttcc aaagaacatt ttgctctcaa tggaatggct   129540
ttggatgttt attacatttt tttttttcact aagttttgta tttctaatgc cttagacaaa   129600
aaattgtgct ggacaatgat cagaaccctg actttgctct tatctttgct taatgggtgt   129660
cgtatatcac tagtggagtt tcttacctac atttaagtat cctcactagc cttcataaaa   129720
taatcatcaa catcaaagat acctgttttct gttctctctt accctgtcca cagaactttt   129780
gcgactttca ggaccagtca tgcagcagtc ccagcagccc cagcctctac agaagcagcc   129840
accacagccc cagcagcagc agagacccca gcagcagcag ccacatcacc ctcagacaga   129900
gtctgtcaac tcttattctg cttctggatc caccaatcca tacatgagac ggcccaatcc   129960
agttagtcct tatccaaact cttcacacac ttcagatatc tatggaagca ccagccctat   130020
gaacttctat tccacctcat ctcaagctgc aggttcatat ttgaattctt ctaatcccat   130080
gaacccttac cctgggcttt tgaatcagaa tacccaatat ccatcatatc aatgcaatgg   130140
aaacctatca gtggacaact gctccccata tctgggttcc tattctcccc agtctcagcc   130200
gatggatctg tataggtatc caagccaaga ccctctgtct aagctcagtc taccacccat   130260
ccatacactt taccagccaa ggtttggaaa tagccagagt tttacatcta aatacttagg   130320
ttatggaaac caaaatatgc agggagatgg tttcagcagt tgtaccatta gaccaaatgt   130380
acatcatgta gggaaattgc ctccttatcc cactcatgag atggatggcc acttcatggg   130440
agccacctct agattaccac ccaatctgag caatccaaac atggactata aaaatggtga   130500
acatcattca ccttctcaca taatccataa ctacagtgca gctccgggca tgttcaacag   130560
ctctcttcat gccctgcatc tccaaaacaa ggagaatgac atgctttccc acacagctaa   130620
tgggttatca aagatgcttc cagctcttaa ccatgataga actgcttgtg tccaaggagg   130680
cttacacaaa ttaagtgatg ctaatggtca ggaaaagcag ccattggcac tagtccaggg   130740
tgtggcttct ggtgcagagg acaacgatga ggtctggtca gacagcgagc agagctttct   130800
ggatcctgac attgggggag tggccgtggc tccaactcat gggtcaattc tcattgagtg   130860
tgcaaagcgt gagctgcatg ccacaacccc tttaaagaat cccaatagga atcaccccac   130920
caggatctcc ctcgtctttt accagcataa gagcatgaat gagccaaaac atggcttggc   130980
tctttgggaa gccaaaatgg ctgaaaaagc ccgtgagaaa gaggaagagt gtgaaaagta   131040
tggcccagac tatgtgcctc agaaatccca tggcaaaaaa gtgaaacggg agcctgctga   131100
gccacatgaa acttcagagc ccacttacct gcgtttcatc aagtctcttg ccgaaaggac   131160
catgtccgtg accacagact ccacagtaac tacatctcca tatgccttca ctcgggtcac   131220
agggccttac aacagatata tatgatatca ccccctttg ttggttacct cacttgaaaa   131280
gaccacaacc aacctgtcag tagtatagtt ctcatgacgt gggcagtggg gaaaggtcac   131340
```

```
agtattcatg acaaatgtgg tgggaaaaac ctcagctcac cagcaacaaa agaggttatc   131400
ttaccatagc acttaatttt cactggctcc caagtggtca cagatggcat ctaggaaaag   131460
accaaagcat tctatgcaaa aagaaggtgg ggaagaaagt gttccgcaat ttacatttt    131520 aaacactggt tctattattg gacgagatga tatgtaaatg tgatccccc ccccgctta    131580 caactctaca catctgtgac cacttttaat aatatcaagt ttgcatagtc atggaacaca   131640
aatcaaacaa gtactgtagt attacagtga caggaatctt aaaataccat ctggtgctga   131700
atatatgatg tactgaaata ctggaattat ggcttttga aatgcagttt ttactgtaat    131760
cttaactttt atttatcaaa atagctacag gaaacatgaa tagcaggaaa acactgaatt   131820
tgtttggatg ttctaagaaa tggtgctaag aaaatggtgt ctttaatagc taaaaattta   131880
atgcctttat atcatcaaga tgctatcagt gtactccagt gcccttgaat aatagggta    131940 ccttttcatt caagttttta tcataattac ctattcttac acaagcttag ttttaaaat   132000 gtggacattt taaaggcctc tggattttgc tcatccagtg aagtccttgt aggacaataa   132060
acgtatatat gtacatatat acacaaacat gtatatgtgc acacacatgt atatgtataa   132120
atattttaaa tggtgtttta gaagcacttt gtctacctaa gctttgacaa cttgaacaat   132180
gctaaggtac tgagatgttt aaaaaacaag tttactttca ttttagaatg caaagttgat   132240 tttttaagg aaacaaagaa agcttttaaa atatttttgc tttagccat gcatctgctg   132300 atgagcaatt gtgtccattt ttaacacagc cagttaaatc caccatgggg cttactggat   132360
tcaagggaat acgttagtcc acaaaacatg tttctggtg ctcatctcac atgctatact   132420
gtaaaacagt tttatacaaa attgtatgac aagttcattg ctcaaaaatg tacagtttta   132480
agaattttct attaactgca ggtaataatt agctgcatgc tgcagactca acaaagctag   132540
ttcactgaag cctatgctat tttatggatc ataggctctt cagagaactg aatggcagtc   132600
tgcctttgtg ttgataatta tgtacattgt gacgttgtca tttcttagct taagtgtcct   132660
ctttaacaag aggattgagc agactgatgc ctgcataaga tgaataaaca gggttagttc   132720
catgtgaatc tgtcagttaa aaagaaacaa aaacaggcag ctggtttgct gtggtggttt   132780
taaatcatta atttgtataa agaagtgaaa gagttgtata gtaaattaaa ttgtaaacaa   132840
aactttttta atgcaatgct ttagtatttt agtactgtaa aaaaattaaa tatatacata   132900
tatatatata tatatatata tatatatatg agtttgaagc agaattcaca tcatgatggt   132960
gctactcagc ctgctacaaa tatatcataa tgtgagctaa gaattcatta aatgtttgag   133020
tgatgttcct acttgtcata tacctcaaca ctagtttggc aataggatat tgaactgaga   133080
gtgaaagcat tgtgtaccat cattttttc caagtccttt ttttattgt taaaaaaaa    133140 agcataccrt ttttcaatac ttgatttctt agcaagtata acttgaactt caaccttttt   133200
gttctaaaaa ttcagggata tttcagctca tgctctccct atgccaacat gtcacctgtg   133260
tttatgtaaa attgttgtag gttaataaat atattcttgt tcagggattt aaccctttta   133320
ttttgaatcc cttctatttt acttgtacat gtgctgatgt aactaaaact aattttgtaa   133380
atctgttggc tcttttatt gtaaagaaaa gcattttaaa agtttgagga atcttttgac   133440
tgtttcaagc aggaaaaaaa aattacatga aaatagaatg cactgagttg ataaagggaa   133500
aaattgtaag gcaggagttt ggcaagtggc tgttggccag agacttactt gtaactctct   133560
aaatgaagtt ttttttgatcc tgtaatcact gaaggtacat actccatgtg gacttcct   133620 aaacaggcaa acacctacag gtatggtgtg caacagattg tacaattaca ttttggccta   133680
```

| | | | | |
|---|---|---|---|---|
| aatacatttt | tgcttactag | tatttaaaat | aaattcttaa | tcagaggagg cctttgggtt 133740 |
| ttattggtca | aatctttgta | agctggcttt | tgtctttta | aaaaatttct tgaatttgtg 133800 |
| gttgtgtcca | atttgcaaac | atttccaaaa | atgtttgctt | tgcttacaaa ccacatgatt 133860 |
| ttaatgtttt | ttgtatacca | taatatctag | ccccaaacat | ttgattacta catgtgcatt 133920 |
| ggtgattttg | atcatccatt | cttaatattt | gatttctgtg | tcacctactg tcatttgtta 133980 |
| aactgctggc | caacaagaac | aggaagtata | gtttggggg | ttggggagag tttacataag 134040 |
| gaagagaaga | aattgagtgg | catattgtaa | atatcagatc | tataattgta aatataaaac 134100 |
| ctgcctcagt | tagaatgaat | ggaaagcaga | tctacaattt | gctaatatag gaatatcagg 134160 |
| ttgactatat | agccatactt | gaaaatgctt | ctgagtggtg | tcaactttac ttgaatgaat 134220 |
| ttttcatctt | gattgacgca | cagtgatgta | cagttcactt | ctgaagctag tggttaactt 134280 |
| gtgtaggaaa | cttttgcagt | ttgacactaa | gataacttct | gtgtgcattt ttctatgctt 134340 |
| ttttaaaaac | tagtttcatt | tcattttcat | gagatgtttg | gtttataaga tctgaggatg 134400 |
| gttataaata | ctgtaagtat | tgtaatgtta | tgaatgcagg | ttatttgaaa gctgtttatt 134460 |
| attatatcat | tcctgataat | gctatgtgag | tgtttttaat | aaaatttata tttatttaat 134520 |
| gcactctaag | tgttgtcttc | ctgaagtttt | tttagtgctt | gaatgactgc cacctcaatg 134580 |
| aagaaaaggg | aataaaaaat | aattttaaa | gacactttta | agatagatag ttagtcttat 134640 |
| gttaaactat | atctaagata | atacccaaat | aattaaggcc | gaagtatttc tctggttaaa 134700 |
| tggtgtagat | attcactcac | ttttccttcc | aactaacttg | ttagtgtatt cactttgcat 134760 |
| gtgtagacag | tgtaaatcag | atagagagta | aagcacctct | aatcttagat tgcccctcc 134820 |
| agtgttttgt | gaagggtttc | agtgatatag | caggtgcact | aaggttgaat tcatattgct 134880 |
| tagaactaag | gccaactctg | ttttcagact | ctcaccttcc | acttcttgcc tactcttctt 134940 |
| aagggaagat | acttcttcct | gtacatcaga | aaggcagggt | ggtaggctgg aggaatgggg 135000 |
| agaggaggcc | tggaaggtat | cagacaaata | tacttgtcct | catctagtcc cacatggctt 135060 |
| caaggagctt | gaggctaaat | catcctcatc | tctacccatt | ctctgccatg tgaatcatcc 135120 |
| catatataat | atcagtgcac | tc | | 135142 |

<210> SEQ ID NO 2
<211> LENGTH: 20660
<212> TYPE: DNA
<213> ORGANISM: Homo sapiens

<400> SEQUENCE: 2

| | | | | |
|---|---|---|---|---|
| atttttagta | gagacagggg | tttcattatg | ttagccagcc | tggtctcgaa ctcctgactt | 60 |
| caagtgatcc | gcctgcctcg | acctcccaaa | agttctagga | ttacagacgt gagccaccgc | 120 |
| gcccggccca | aagtgagatt | tcaactctct | ctacaccagc | tggacctgac agcggactcg | 180 |
| cggaggcgca | gacgccgccg | gcggtcttag | ctcaagaatg | aagcagccgc actgggctaa | 240 |
| tgcgcctttg | ggttcagccc | ggcaggcgag | ggaagcaaga | gttcgctcag attggctttt | 300 |
| gggtttaagc | taaagcgtca | gaaactgaca | tccaggttta | catgggcat cctggagagg | 360 |
| gtcagcctcg | caagcggctc | tgctaatccc | ccagccctga | tcccgctcgc gggtcccggt | 420 |
| gggtctcacg | cctgtagctc | ctgcggagct | gggctttcag | cggcgcccag agaagcacca | 480 |
| gccgggcctg | gccgccgggt | cccggctccc | gcgggacgct | ggaggcgtcg gcggccctgg | 540 |
| ccccgcctcc | tccccggcaa | ggcccaatgg | ggcggcaggc | ccggcagccc cgccccggtg | 600 |
| gtgcccgcgc | ggccagcgcc | cgccaggccc | agcgttagcc | cgcggccagg cagccgggag | 660 |

```
gagcggcgcg cgctcggacc tctcccgccc tgctcgttcg ctctccagct tgggatggcc      720
ggctacctgc gggtcgtgcg ctcgctctgc agagcctcag gctcgcggcc ggcctgggcg      780
ccggcggccc tgacagcccc cacctcgcaa gagcagccgc ggcgccactg tgagtgccgc      840
gcggagggtc caggcaggcg cgcgccccca gctgcgacgt ggcggcttcc caggctgggg      900
ccgggaagca cgtcccgcca gcccgcagcc cggggacggc ggggtcaggc gcacaaaggg      960
ccgcgggggca gcttcgctcc gcgctccccc gcccggcgct tcccggccgt gccaggcgct     1020
ggggtgggga cttgagggac ggtggcaact ggtggcccgg gcgacggcca gctctgcgcg     1080
ggcgggggct cggggctgcc gcgcgcccct aggtatttcg ggagggggtc ctgagagtgt     1140
cccggacccg aagggtggcc tgcccgccct gcgccctgg aacgagacga gcaccgtgg       1200
ggggctggag caccccgcgc gctccccggg cgagagggag ggtcgtggct cggcccctgc     1260
tcagacaaag gctgggaggc gggagacatg cacttcccct tccttttcag ccaggcgcgc    1320
gctgatacca ggcccacgtc agctattttt ggagcctttt acacgacagc tggaggagcg     1380
tccttttaa ttttccccctt ttgtttggcc gcccccaccc ccaccccttc gccttcatcg    1440
ctgcacttga ggctccatcc tggggcctct ccttgacttg acctgccttg gcaggcacat     1500
gccctccctg cctggctcac tcgccgcaga gacctggcag cccgcgcaaa atgtcacttt     1560
gcggaatcgt tcccacggct tctgggtacc cttagttccc tgcttaggag ggaagacagt    1620
agtcgggtcg taataagcaa gacttagccc gagcctccgt tgccaacgca ggctgccttg     1680
cttggcgtgt gggcatcggc ctgccccctc accctggcta cccaacacag ctacaaaagg     1740
cagggaacaa tgtaggtccc ttggccctgc ctaatgcctg ttgccatgga aacccctatc     1800
ctaatctggc caggagcccc ttgcagtgag ccaggagagt gaggaagagg ggatggggcc     1860
cgctggccct gacctggcca gaggaggtaa tggttaaccg gattgtggga gcagctgact    1920
agagccgggg gggtagggag gcttgggccc cagtcctacc ttccctgcca aggagaaagg    1980
ggcatgtctg cttttgtacc tctgggaatc tacctcaggg atctgcccaa caactcccag    2040
gttccaagtg ccccaggacc caaagattcc catatagcac accaccttca gcaaaaatat    2100
ggtggaagtt agccacattc tttaattctc ccttttttc tgccttgatg gtaaaaaaa      2160
aaaaagaaa caacaaccc gaaaacaca cacaaacagg aacacaaagc gccttttaag       2220
ggtcctgaat ttggatacag aaaaagcagt cagttgcagg cccttctaga agtccccatg    2280
tgggttggtt atgaatgggg aaattgcttg gtgttggagt tggacatcag actctacagt    2340
tgcgactctg ccagcttgtt acctggcaac gcagctggag acagaatact tggcattccc    2400
cttgatgaca aggaaagaat atttttggggc taaaagagcc ccgtgtcttt gctgcctggt    2460
aattcctgca cgcatctttt cctatttgc aacgccatag gcttcagcg actgctggtg     2520
atgtttctgg taagttagag cttggggcag tgcggaccag ttctgtgaac ggctcagtgg    2580
cagaattact tatctagcct tccttcactc taacccaga aacttcttaa ttcttgcccc     2640
ttaagtgtgc agatctttct gccacgtcag ataaggcct agctgccctg ccagagctga    2700
ttggggtggt tgtgtttagg cctagtaggt actgaggaaa agcctctttg gaatggctga    2760
ggcctgctcc cacatcttct gtgtgaagtt gagggccctt gggctggttc cattcagggt    2820
atgaggtgct ggaaactgct ctcagattac tggaagccag ggtctgtggc cttccctggg    2880
gtttatactc tgtaaaccca tgttaaaaat accagcagat tgcaaatatt agtacactgt    2940
aggttgtaag cttcttcagg gcatggggcc tattgctgga gagagatgcc accgtgtac    3000
```

```
atctggtgca ggctgctggt aagaactcac tggcccctgt gtggcaatgc ataccagatg    3060
ggtgagaggg gaggaaacac attcagtgaa acagaaggtg agggcagggc agccctgacc    3120
acagatggag ttgacttcaa cttgaccttt atttatgtct ttgacaaaag tagtatactc    3180
ctactttgtg ccagacacca tgccgggtgc tggggataga gctgggaata aaaccagcag    3240
agactctttc aaaaccctta ggagctcaaa ttctgatgtg ggaggggca gacagtaagc     3300 aagatagatg ttgactagta tgatatatgg gtacaagagc taaggaaggc caggcactgt    3360
ggcttacacc tgtaatccca gaattttggg gggctgaggt gggaggattg cttgaggctg    3420
ggagctccag accagcctgg gcaatatagt gagaccccat ctctacaaaa ataaaaaata    3480
aaattagcca ggcacgatgg tgcatgtctg tggtcttagc tactcaggag gatcatttga    3540
gcccaggagg tcaaggctgc agtgaggtac aattgtgcca ctgcactcta gcctgggtga    3600
caaagcaaga ccctgcctcc cccttctccc cccaaaaaga gaagagctaa ggagaaacag    3660
gcaagaaagg tgtgtgcaca aaagtttgta tagggcagcc agaaaagtcc tcactgaagg    3720
aatcgctgag gagggagga agcaggccat tttcggtatt gggggaagag ggactcgcag    3780
gtgccaaggg catgatggaa gagcagagag gatggtgcga aggctggctc agcaggcacc    3840
aggtggagtg acaggatgag gttcggcagt gggtctgta gagggctcac aggccatttt     3900
tgagagcttt cgcttttact ttgcagggtt ttgagaggag tatcgttacc tgatttccat    3960
cttatcggga gcattctagc ttcagggacc tggcaagaga ggatgatggc ttggacctgg    4020
gtggtggcgc tggggatggt gaagaagtgg ttggattctg gatatatttt gaaggaggag    4080
ccagtagtgg ggaaaggttc caattcaggc gattttacat aaaaatctag atacgcagca    4140
ggcactcact tatggcaagg gtgggcttgt ctgagggtgg cttctggttt tggtggtttg    4200
gatgtgagaa agggaagga atgaaggatg acaccaagga gtctactaga gtttgttcca    4260
aaatggctgt tctggccgcg tgcggtggct cccaggactt tgggaggccg aagcaggcgg    4320
atcagttggg gccaggagtt cgagacctgc ctggccacca tggtgaaacc cggtctctac    4380
taaaaataca aaaattagct gggtgtggtg gcaggcgcct gtagtcccag ctactcaggg    4440
gctgaggcag gagaattgcc tgaacccagg aggtggagct gcagtgagc cgagatcacg     4500 ccactgccct ccagtgtagg cgacagagtg agactctgtc tcaatacata catacataca    4560
tacatacata catgcatgca tacatacata catacataca taaaatatac aaagttgctg    4620
tcctgccttc ttgagccccc aggaattgga acctttcccc actctctgat cttttgctgg    4680
gacatgctga ctgagcagcc tttctgctga gagcatgggt aggaatgtgg agggagcagt    4740
tatgcctggg gctggctgcc tgcggctgga cctctagcct cctgctggga gcagcaagaa    4800
gccagggatg tgttttgaaa tccttacttg gtattgggtg ctaggagccc cagacaggga    4860
ggagagtcag cctaacgtgc ctctggtgac tggtgtaatt ccatcctgca ctctcgccaa    4920
gaggacagtg tttgtgcaat gcatcagctg aagattcgtg gtggctgtca cttcggaggt    4980
tttcagggag gcctagctgc tgctctgtgt atttcaggta gcttgtcacc acttatctct    5040
cagagaaggg cagaccatgg ctgtatctcc accatacagg ctgaacagca gacagggtc     5100 tcaaactcca gtgccctggg ccacactgga gggcacttgg ctgtcatgga gtgaagggag    5160
aggccgcctt cagcccagcc catccttgcc atgagtgagt gcctgctgca tttctagatt    5220
tttatataaa atctcctgat tttttttgac tggtttaaat tttattatt ttggtaaaaa     5280 acgtataaaa cttaccatct tagtcattgt tcagtgtaca gtattgttaa gtacattcgc    5340
actgttgtgc agacattacc accatccatc accagaactt tgtcaccttg caaaaccgaa    5400
```

```
actctctacc catgaaacaa tacctcccca cttcccgtcc ccagtccctg gcagccacct      5460
ttttactttc tgtttctatg aatttgacta ttctaggtac ctcatgtaag tagaagcata      5520
tagtatttgt cttttgtgac tggtttattt cacttagtta gcataatgcc ccccaggttc      5580
atccactttg tagcaggtgt cagaatttcc cttcttttca aggctgaatc atattccatt      5640
gtatgtagat aacagtagtc ccccttatcc ttggaggatg catttcaaga tccccagtgg      5700
atacctgaaa ctgcaaagcc tgtagatact atgttttttt cctatacata cagatctatg      5760
ataaagttta atttatgaat taggaacagt aagagattag caataataac tagtaataaa      5820
atagaacaat tataacaata tactgtaatg aaagttacat gaatgtgatc tcttaaaata      5880
tcttactgta ctgtactcac ctattttcag actatggttg actgtgggta actgacacca      5940
caggtaactg acgtcatgga aataaaacct ttgataaggg gggactgtat cacattgtct      6000
ttatccattc atctgtgatg gacacgtggg ttgcttctat cttttgctgt tgtgaacatt      6060
gctgctatga atgtgggcat acatatatct ctttcagacc ccgctttcga tattttggga      6120
tgtatataca gaagcagaat tgctggatca tatagtaatt cttgtccttt tcttttcttt      6180
ttttttttcg agacggagtc ttgctctctt tcgcccatgc tggagtgcag tggcgcgatc      6240
tcagctcact gcaagctccg cctcccgggt tcatgccatt ctcctgcctc agcctcccca      6300
gtagctggga ctacaggcgc ctgccaccac gcctggctaa ttttttgtat ttttagtaga      6360
gtcagggttt cactgtgtta gccaggatgg tctcgatctt ctgacctcgt gatccacccg      6420
cctcagcctt ccacagtgct gggattacag gtgcgagcca ccgtgcccgg cagtaattct      6480 tttccttta gctaaggaac acccatactg ttttccacag cagctgcacc atttcacatt      6540
cccaccaaca gggcacaaga gttccaattt ctccacatcc ttgctagcac tttattttct      6600
gttttgtttt tcttttcctg atagtagctc tcttagtggt tgtgagggga tagtgggggtg      6660 atatctcatt atggttttga tttgcatttc cctgatgatt agtgatgttg agcatctttt      6720
catgtgcttg ttggccattt gtatatcatc tttggacttg aaatgtctat ttaagtcttt      6780
tgtccattat atttatttat ttattttgag atggagtctt cctgttaccc aggctggagt      6840
gcagtggcat gatctctgct cactgcaacc tccacctcct gggttcaagc aattctcctg      6900
cctcagcctc ccaaatagct gggactacag gtgtgtgtca ccacaccagg ctaattttt      6960 ttctattttt agtagacaca gagtttcacc attgtggcca ggctggtctc gaactcctga      7020
cctcaagtga tctgccctct tcagccttcc aaagtgctgg gattacaggc atgagccacg      7080
gtgcccagcc agtcttctgt ccatttaac gttgagttat ttgttttatt gttgagattt      7140
actgattttt aaaacttggt caccaattaa gattttttta aaaaccagt acctggaaca      7200 agcagaacaa gtctctgctg gccttggctc atgttgctgt tctcagttcc cctgggatgt      7260
ttgcttccag ggaggcctgg gcactcctga ctttggtgac agccctgctt gctctctctc      7320
tgttacctgt aggtttcccc ttccacattc actgcctccg ggcaggcact gttgtgtttt      7380
aggcatttca gtatcccagt ggggtactgg ataagtgctt agttagcacc tgccggtgag      7440
taaataatca ggtcctgtgg tctctgaggg tttgacacat caggtctttg atcttgacct      7500
tgaactctcc tagccatgcc tgcctgaagc ccaaccgtgg agcccaggct gaggctgaaa      7560
cctgaagaac tggccccaag tgagtctctc cttagggctc ctgattatga tagttcattt      7620
tttttttttt ttaacaaatt tgattagctg tcctcaaatt aactcatagg agatgctccc      7680
cagaactaaa ctagctctgc aacagctcaa cagactttcc gcaggttctg cagctctttc      7740
```

```
cactcaagct tcagaaaaaa gtgaaggaat attgtagatt gggttcaaaa tccccatcgc    7800
gtcttgggaa aggcagtaga gccagcagcc agccaccttt tgttctctag ggaatggaat    7860
agtccaaggc tgtgtttgtg ttctgcttct ctacatctga cccacgggtc ttccagaggc    7920
tgcatttggg tcagggacct gggctctatc ttgcctctga tgcagaccac actctctgag    7980
tctcattatt cccctaaat gatctctaag attatttta gattaaaaaa aaaaaacaaa    8040
ctctttgcat atctttggaa agtcagttgt ttgaggtctg ttaggcttta atcactttg    8100 ttttaaatgt gccgaggtgg tttctaggcc tgcttttcac aggtattctg tcccttgtca    8160
gttcttccca cccagttttt tttgtttgtt tgtttgtttt tttgagatgg agtctcgttc    8220
tgttgcccag gctggagtgc agtgccgtga tcttggctta ctgcaacctc cacctcccgg    8280
gttcaagcga ttctcctgcc tcagcctcct cggtagctgg gattataggc acgtgccacc    8340
atgcctaatt tttctatttt tagtagagat ggggtttcac catgttggcc aggctggtct    8400
tgaactcctt accttgagtg atccacctgc ctcagcctcc caaagtgcta ggattacagg    8460
catgagccat tacacccagc cccaacccag tgttttcaaa taatcattct cttcccttca    8520
cctgatttgc tgtgtctaat ctagagtgga gctgaagaca catcaccacc tctctaagga    8580
ctgtgtgtaa cacaagagta attgggctgt aagtgaggct gaggagtgct gctttgagga    8640
aagggcacag ctctcagctg agctggtgag atttccctgt gactgaagtt ttattagatc    8700
ttgttccctg ctctgcattt gctgcttctt cccaggctgt gggcagagga gcaggctggt    8760
gccccggtgc ccctatctgc tgcaggctga ggttcaacaa gccttgtcca aggcagctgt    8820
actgattcat tgttaggtgg ccagttcctg agttttcttt gaaattcact tcccagactg    8880
ttgggtattc ctgcgagtca gactctcctt cagtagcgtc ccctgccccc taccctccac    8940
tggtctccct ggacctctga tcagcccctc attgagtcct ttgatgcttc tctggtagga    9000
ctgacccacc tgcgtcggct gggatcaagg gttctgagtt ccattcgcag gtgctgtaag    9060
cctgtccttc ctgttgaata gggtcagagt cctcgtgact ctgctgtttt caagctctgt    9120
aaccttgggc agtaagctgt taacctctct gagcctcagt ttcccacact taaaatggag    9180
ataatggcca ggcgtggtgg ctcacgcctg taatcccagc actttgggag gccaaagtgg    9240
gtggatcacc tgaggctagg agttcgagac cagcctggcc aacatggcaa accccgtct    9300 ctactaaaaa tacaaaaatt agccgggcct ggtggcgtgt gcctgtaatc ccagctactc    9360
aggaagctga gacagcagaa tcgcttgaac ccgggaggca gaggttgcag tgagccgaga    9420
tcacgccatt gcattccagc ctgggtgaca gaccaaagac tctgtctcaa aaataaata    9480 aataaataaa taaattaatt aattaaataa aatggaggta atgataccatc cttggggttg    9540 tttttgggat taaatggaat cacattgtac agcattggta cactgtaagg cacatagtag    9600
gcactcaata cctatctata ctatttcctt tatcaccaca agttagttga gggctcttgg    9660
gttgcacgca acagacaaag ttagtgactg gttaacttgg agaggatttt attatgagct    9720
acacagcgta gctcatagaa ttgcagggaa aactataaag aactaagtct tggacaaaag    9780
taatatcttg gcatgggcct gtagccccag ctactaagga ggctgaggtg caaggattgc    9840
ttgagccccg gagtctgagc ctggcttggg caacagagag agataaagag accctgactc    9900
taaacaataa gtaaatacat aaaagaggac ccaggccctc cttaggaact ggatggcagg    9960
agccctggaa caacctctta ctgatttggt gctggatgag gcagccgcag ctagccagtg    10020
ttctttgtgt tgatctcctc tgccttcata ttccagggggg agagggtctg acaggccaga    10080
ctggccccca ccctcttggc cactggtggg ctgggcatgt ttttgggtag ttctacctag    10140
```

```
ccagattaaa gtgggggtgg ggtggggagt ccagccagcc tgggcaacag ggcaagactc   10200
catctctaca aaaaaatttt aaaattaggc tggcacggtg gctcacgcct gtaatcccag   10260
cactttgcgg gggtcaaggc aggtggatca cttgaggtca ggagtttgag accagcctgg   10320
ccaacatggt gaaaccctgt ctctactaaa aatacaaaaa attagccagg tgttgtggtg   10380
cacacctgaa atccccgcta cttgggaggc tgaggcccga gaatcacttg aactcgggag   10440
gcggaggttg cagtgggctg agatcatgcc actgcactcc accctgggg acaatagcg    10500
aaacttcgtc tcagaaaaaa aaaaattaa aaatagctgg gtgtggtggc atgcgcctgt    10560
agtcccagct acttgggagg ctgaggtcag aggatcactt gaagccagga agtcaatgct   10620
gcagtaagct atgatggcat cagtgcattc cagcctgacc aatggaacag gaccctgcca   10680
agaaagagag agagaaaggg aggaaggaac gaaaggaagg aaggaaggaa agaaaggaaa   10740
ggaaggaaag aaaggaaagg aagtaagtaa ggatggatgg atccaggtgc tctaaaccag   10800
cagttcccaa agtttttggc accaggggcc agtttcatgg aagacaattt ttccacgggt   10860
ggcagggtgg tgggcagcgg ggatggtttt gggatgagtc aagtgcatta catttattgt   10920
gcactttatt tctattatta ttacattgta atatataatg aaaaaattat atagctcacc   10980
ataatgtaca atcgggggt cctgagcttg ctttcctgca actagacagt cccatctgga    11040
ggtgctggaa gacagtgaca gatcatcagg cattagattc tcataaggag tatgcaacct   11100
agatccctcg tgtgcgcagt tcccaggcat gagctcaggt ggtagtagtg ctcactcacc   11160
tgcagctctc ctcctgctgt gtggcccagt tcccaacagt ccgtggacct gcactaaagg   11220
ctgtggcctg gtctgctgac ctctctccag agcccacggt actagtccat ggcctgggag   11280
ttggggaccc ctgctctaag cagtgaggga gctgatttgc agacggggga gtggacaccg   11340
ggcagctgga gccctggctt tctgccactg tctcctggtg aagggcgggc ctggctggga   11400
ggagagggcc cccctccagc ctccccaggg gcatgatgcg ctgtgtgtcc ctgcttctag   11460
atgccgacaa aaggatcaag gtggcgaagc ccgtggtgga gatggatggt gatgagatga   11520
cccgtattat ctggcagttc atcaaggaga aggtagtgcc ccctcctgaa gtgggtggct   11580
ctccaggtgg gctggccagg gattgttctg tcccacaggg tcttctggac tgcaggtccc   11640
taggaccccc ccgttgtcct ggtaggcagc agcagctctg tttctctccc tctgtctacc   11700
cttctttcac atctggtcca ctaattgttc agaagtcgtc aggcggggc ctgtccccag    11760
cagtccgtgt tgtgatggtg ccagatccca cacgttctgt caactttgag aagcttcaag   11820
gttaatcctg tatcatttcc atcttgatcc cctacgtttt gcctcacttc ttgaaaagga   11880
gtgaaagggg aacagggctg gtgtgtaggg cagtgaccca gcctgcagtt gtgacgagcc   11940
accatggcaa aggggtccca gagtggccgc ttggcttctc caaagttgcc gtggtctatg   12000
tatgtccagg agagcatgta gtccttgtga aggccccaca ctgtgtgtgc gttcatggga   12060
caaaggttga gaactgtcac ttccaactgt aagatctcaa agcacttgag aagaggaaac   12120
cagttgtata gagaaatcta gatgtacttg gggttggggt ttggctgagt tgatgggcca   12180
tgtgagggggg gcacacaggc acagtggagg aagaaccctc caaaagactg cggcctggcc   12240
tgccaacctc tctccaaagc cccagcctct gccagctctg gccaggcccc actgagaaat   12300
ggctgactcc agctttctgc tgcgcccctc cactggcctt cactcatccc tgttttgact   12360
gactgtcccc tgccatggcc tgcagacttc ttatcctgcc ctttgttgtc atgtccctga   12420
gtcactgggg tgacgccttg ctctggccct ctgtccccag ctcatcctgc cccacgtgga   12480
```

```
catccagcta aagtattttg acctcgggct cccaaaccgt gaccagactg atgaccaggt    12540
caccattgac tctgcactgg ccacccagaa gtacagtgtg gctgtcaagt gtgccaccat    12600
caccccctgat gaggcccgtg tggaaggtgc gagggtgtgg aggtgggcgg ccagggagg    12660
gtcacaggct tctcccaccg gcctctccag acttggggtg gggcagttgg ccatgtcact    12720
catctcggga ctgggaggtt gggaggctcc agagctgggg ctttcctgag ccaactgca    12780
cctgaggcca gtctccctgt gtgtgcctgg tggacagtgg ggcctcagag gtcacctttg    12840
atgaggctgg ggcaggcgtg ggtaaggggc tggcctcagg ttccacggtt agggcacagc    12900
agagctgaga acagaatcca tgtcttccat ctcccaggcc agtggtgttt ctgcttcact    12960
ctggctctga cagtggtagg tgtcatcggt gacagggctg aggaggagga ggaggaggaa    13020
ggtaatgctg atgtggtcac agtaaggatg gcttctttgg gcagtagtcc attctggcgt    13080
ggacagtctt gcaggcaggt atgcagagag attgtgcaga ggagtgctgt gtgtaaggcc    13140
tgtgtccttc agagcctcag cagcctctgg ggaacattgc tgttgccctc ctgccactgg    13200
cttggccttg caggtctgcc tctgtcccca tggtcatgca gggtcactga gaggtgcccc    13260
caccaggcct agactggctt ctggtccttg gctgttgggg ccgctctcga gggttccatg    13320
aagtcacagc agtgtgtgtg cagaggggcc aggtttggat aattcgagaa aggatggttg    13380
aggagttttc tgagctctct cttcctactt tccacagttg gagggagctg gcggaaagta    13440
ctcgagatac atctgcaaat tccccaggcc tgccctgtc ctgcaggtca tgcctgaccc    13500
acagcactgg gatcatttga gtgttgagct cttcatttca cctgaaccctt gggagttgtg    13560
tatccccatt tatggacaag gcaggagagg gtcacagcct taggaactgg ggtggcgttg    13620
gggccaggac cggagcatgt ggagtgggca gtgtgttgtc aggcttcgtc agacaagtcc    13680
ttcccccgga ctgtactccc tccatgtgtg atgtgggaat cataatggcc aacagagcac    13740
ttagcatgga ccgggcaccg ttctaggccc tttacacacg agctcatttc gtcctcacga    13800
caacacttag gctggttatt tttccagtaa ttttttttta cagcttggt tgagccactt    13860
ttgtaagcct caccattaaa actggcagac ttgctgggca tggtggctca cacctgtaat    13920
cccagcactt tgggaagccg aggcgggtgg atcacctgag gttgggaggt cgagaccagc    13980
ctgaccaaca tggagaaacc ccatctctcc taaaaataca aaattagctt ggtgtggtgt    14040
cacatgcctg taattccagc tgctcgggag gctgaggcag gagaaccgct tgaacccagg    14100
aggcagaggt tgtggtgagc cgagatcgcg ccattgcact ccagcctggg caataggagc    14160
aaaactctgt ctcaaaaaaa aaaaaaaaa aaaaaaatt ggcagactcc agagcccaca    14220
catttgcact ctagactcta ctgccttcct catgaagaat tttaggaccc ccgtctggct    14280
gtgttgttgc ttggggttca aattctggtt gaaagatggc ggctgcagtg ggaccactat    14340
tatctctgtc ctcacagagt tcaagctgaa gaagatgtgg aaaagtccca atggaactat    14400
ccggaacatc ctgggggga ctgtcttccg ggagcccatc atctgcaaaa acatcccacg    14460
cctagtccct ggctggacca gcccatcac cattggcagg cacgcccatg gcgaccaggt    14520
aggccagggt ggagagggga tccactgacc tgggcacccc ccgactggag ctcctcgcct    14580
agccatcctc ttgtctctgc agtacaaggc cacagacttt gtggcagacc gggccggcac    14640
tttcaaaatg gtcttcaccc caaaagatgg cagtggtgtc aaggagtggg aagtgtacaa    14700
cttccccgca ggcggcgtgg gcatgggcat gtacaacacc gacgaggtga ggctggcttg    14760
ggcatcctgg gcccctcctc tcccagcttg tctcttcatc tctgtctcgt ggctttcctt    14820
tcttctgtaa tggcctcatt cttaggccac aaagaggcag aaatggccac cagggctggg    14880
```

```
catggtggct gacacttgta atcccggcat tttgggaggc caaggcagga ttgcttgaga    14940
ccagaagttt gagaccagcc tgggcaacag tgagacccca tctcttgaaa caaaagaaa    15000 agaaaagaaa agaaaagaaa tggccacgag cagctccagg cgtactcctg cctgcttggc    15060
taccctatca gaagagaatg cctctttatc cccagttcca gctccaatgc caggctgagt    15120
cacatgacca cctctgagcc aatcacagag gccctgggga gaaaggcttc tgattggata    15180
agccagggac acactgtcaa ccccagcgct aggcctggga attagccctg ccccagccac    15240
atgtagtcta aggcggtgct ttccaaaaaa aagttgtttc caaaaaaaaa aaaaaaagg    15300 cggtgttttc caaaaaaaaa aaaaggcgg tgttttacaa agcaaagttg agagggagag    15360
gctgggccag cagaaacatc gtgtgcactg cacggaggct ggtgttaaac agtcgcgtgg    15420
gcggcggggt accgttcctg gagagctggg ccttgccctg ggaggtggga ggttgccggc    15480
aatcgccagg ctagggcacc acgccagggc cctgtctctc ccctgcagt ccatctcagg    15540 ttttgcgcac agctgcttcc agtatgccat ccagaagaaa tggccgctgt acatgagcac    15600
caagaacacc atactgaaag cctacgatgg gcgtttcaag gacatcttcc aggagatctt    15660
tgacaagtaa agcctcatcc atgtactctg tggccttcct tcccttcccc ccatgctgtt    15720
cccatcctac cctgggaagg tcgctattag agtgcatttg gctcagctcc gaggctcagg    15780
gagggatccc caacctgtca gccttctgcc ctctccccat aacagacctt tttactccca    15840
ggcactataa gaccgacttc gacaagaata agatctggta tgagcaccgg ctcattgatg    15900
acatggtggc tcaggtcctc aagtcttcgg gtggctttgt gtgggcctgc aagaactatg    15960
acggagatgt gcagtcagac atcctggccc agggtacgct gggaggacgc tgctccctgt    16020
gggggtggac tgttggtctt ctctggctgg agggattttc agacccttt ggtagaaaac    16080 tctagtggag caggactcat tgcagggtcc tctgtggaca gcaggggca ggagctccct    16140 ggcatctgag tgagagagga tcacaaatta ggtttggact ggtgtatgac tgaggctgct    16200
cttagagaga aaggagggca caggaattcc agggctaggt tgacagccct aaggttgctc    16260
cagtccatga tggagcctca tgactctttg gttccagtag gaaatggga tcaagcggga    16320 ctggaggttc tttaaactac agcgaatgca ttttgcatag tgaacctaat ggatggaaga    16380
gaatgttggg gaagcctgca accccccaag ccctaggggtg tcctaaaaga caaatcagat    16440
tgcagtaaaa agtataggtg atgaggtcag gagtttgaga ccagcgtggc caacatgacg    16500
aaaccccgtc tctactaaaa atgcaaaaaa atttagctgg gcatggaggc gggcacagtc    16560
atggacacct gtaatcccag ctacttgaga ggctgaggca ggagaatctc ttgaacccag    16620
gaggtggagg ttgcagtgag ccgagattgc gccattgcac tccagcctgg caacaaggg    16680 tgaaactccg tctccaaaaa aaataaaaaa taaaaaataa agtataggtg agaccattag    16740
agaagaacag cgagaaatgg gccaattgtg ttgggaacaa gagcaggaaa ggtggtaggt    16800
gtgggaaaca ggcaggacat agagagtgaa agagaaacct aagcttacca gggcagctcc    16860
tggtatgggg aaaagggaag cccaggacgg gttctgatga aaagcagagt cttgttactt    16920
tgtgtaaacc tttggcttta ctttggaaag ttcagtgggg atcctctcac cgaacaattc    16980
ccatctagga tagaaggatg aaacgccata gcagatgagg cagaggcatg aaaatgaacc    17040
ttaagtgtct aaggaatggt gtgaaggtgc aggtaaaatg gagaagggat tgcttacagc    17100
caaaattctt agaattcata gacaaagcat tttcctgtag atgttgtcca tgttttcttt    17160
cttcaatcct tattttggtg tcatggggt gcctttgaag ccctggagtc cttgacaata    17220
```

```
gaaaagcttg ctggagttga catgtggatt tgggagcatt cagaaattaa tcaaaaagct   17280
tgaaagtggc ctaagagagt agctgcaaaa gtgattgttg ggaaatagct gaccacagct   17340
ttattgtttt ccttgaatgt gcctccgggt cacgagccag gctggtggc aggctgtggg    17400 ggaccacagg actctgtggc ctcttgggcc ctgtgggcca caggctgtgg ggcgcctgga   17460
gctggtgaca cagatggatg ttaatgtgct ggtgatagcc accctccagt gccctccagc   17520
cctgtgctgg gccctggaga cccacaggag ggtgaagaga cctggaacag tccctgtcct   17580
cccagttgca gctgggggag gctgagtaga gccacgaact atggcagcta caatattggg   17640
ttgtagaggg cagcagggct cagctgggtg gccccaggag aggcgaggcc ctgagagaaa   17700
ggctttctac cctccaggct ttggctccct tggcctgatg acgtccgtcc tggtctgccc   17760
tgatgggaag acgattgagg ctgaggccgc tcatgggacc gtcacccgcc actatcggga   17820
gcaccagaag gtgagtgcag ggcatggggc ctcacaatgc ccctctaccc caggggccta   17880
aagcccactg ggctgagggc tggaaggacg agcctgaccc accagcccag gggcgggcag   17940
ctgtatctgg gcagcctcct cactagctgg ctcggctctt gatctccctg caaccccgt    18000 ccccagggcc ggcccaccag caccaacccc atcgccagca tctttgcctg gacacgtggc   18060
ctggagcacc gggggaagct ggatgggaac caagacctca tcaggtgagc atggaggag    18120 aggccggagc tgcccaggac aggctctggg tcctgccctt gcacagatgg ggtctcattc   18180
tgccccatcc ccataggttt gcccagatgc tggagaaggt gtgcgtggag acggtggaga   18240
gtggagccat gaccaaggac ctggcgggct gcattcacgg cctcagcaag tgcgtggcct   18300
ggggtggtag gcagaccctg gggccatgtg ggaggaagcc aggggacccc tcctaaagtc   18360
cccctcatga gtcagcttag ctgcaagggg gcctggggca ggacatgtcc acagccctga   18420
gagactgctc aggccagcct ctgtagacca ggtctagtga gttcctcccc atccctgagg   18480
ctggctactc agagctcctt ccgaccctgc ccacacccct ttcccagctt ctctcaggag   18540
agcagttacc tggcaagaca gaccctgcgg gtgcctgccg aatctcggtg gcctcatggt   18600
agggggctat agctggcctc tggcctgtag tctgggtggc aggagatggc tgttctgatg   18660
cccaagctca ggctgttccc tggaagggcc tggctgatgg ccttggcaag gcctggagcc   18720 accctgatg tgagtggtgc tctctctgca gtgtgaagct gaacgagcac ttcctgaaca    18780
ccacggactt cctcgacacc atcaagagca acctggacag agccctgggc aggcagtagg   18840
gggaggcgcc acccatggct gcagtggagg ggccagggct gagccggcgg gtcctcctga   18900
gcgcggcaga gggtgagcct cacagcccct tctggaggc cttttaggg gatgtttttt     18960 tataagccag atgtttttaa aagcatatgt gtgtttcccc tcatggtgac gtgaggcagg   19020
agcagtgcgt tttacctcag ccagtcagta tgtttttgcat actgtaattt atattgccct   19080
tggaacacat ggtgccatat ttagctacta aaaagctctt cacaaaattg tctgctgtgt   19140
ttgtccctga ggggaggagg tagtgggacc ctgaggcaga ggccctgcta gagctggcag   19200
gttcccctgg ggcagaccag agcacctcag gaagggctg ccacggcagg aagggacca    19260 ggcagccctg ggagcccgca ttccacaggg gcccactgcg gagttctcgg acactcaggg   19320
cacaggcctg tgggttccct ggaatttttct agcatgatcc agtttctgtg tccagttctc   19380
cattctgaga gtcaatcagt tcctgatagg ttgtcattga tttttttctt cgttggtttt   19440
aaccttctaa acatctccag gccacttctc tagccttttt ctaggtacta aaagaggtc    19500 ctacccacac ctgcctcaca cttctccttt ccaaggctgc ctgagtttgg aggggcttgg   19560
gtgtgtgtga acaagggccc tgcattgtct aggcctgcag ttcccaggct tgggttcact   19620
```

```
ttcaccatgc attggcaaaa ctagaaaagt aagcttgtga caaattgttc tcggccgggc    19680
acagtggcgc acgcctataa tccctgtact ttgggaggct gaggtgggtg gatcacttga    19740
ggccaggagt tcgagaccag cctggccaac atggtgaaac cccatctcta ctcaaaatac    19800
aaaaattagc caggcgtggt gatgcgcacc tgcagtccca gctactcggg aggctgaggc    19860
aggaaaatgg cttgaacctg ggaggcagag gttgcagtga gccgagactg caccactgca    19920
ctccagcctg ggtgacagag caagactctg tctcaaaaaa aaaaaaaaaa aaaaaaaaa    19980 aaaaattgct ctatgcaagt tttttagccc catgtaaaaa ggaaaaataa aagttgctct    20040
aaagctacat ataatcaaaa ggactgtcct ctgcatagta agttctgcaa agcttcttct    20100
ttttggtgtt aaaatgtcct ggagaagagt tgtataatct ttataaagtc ctggccaggt    20160
gtggtggctc atgcctatag tcccagcact tgggaggcc aaggtgggag gatcacttga    20220
gcccgggagt ttgaggctgt agtgagctat gactgcacca ctgtactcca gcctgagtaa    20280
cagagtgaga ccccatctct caaaacccca tcttacaaag tcccctttcct aaatactggg    20340 gggactccta tggctcctga aacccgacca ttgcggtaga ctgagtggct ttggaagggc    20400
tctagccctc catccacact ggtgacccc cgcttgcttt tcctgagtaa tgccctgaaa    20460
ctctcagggc tataagaaga aacgtggact gctggctcta gcaggcccag cccctgggag    20520
gaagctcaag gcttcctgcc tcttcttgcc tgtcaccagc acggggctgg cagctctgca    20580
gaacgcagcc tctgaagccc agcctggcat cgggagctgg cttctttcct gaagccatgt    20640
gggtgggtag ggaggggaag                                                20660
```

METHODS OF TREATING AND PROGNOSING NONHEMATOPOIETIC MALIGNANT TUMORS

CROSS-REFERENCE TO RELATED APPLICATIONS

This application is a national stage of International Patent Application No. PCT/US2015/064016, filed Dec. 4, 2015, which claims the benefit of U.S. provisional application No. 62/089,148, filed on Dec. 8, 2014, which is incorporated by reference herein in its entirety.

GOVERNMENT RIGHTS STATEMENT

This invention was made with government support under CA008748 awarded by the National Institutes of Health. The government has certain rights in the invention.

REFERENCE TO SEQUENCE LISTING SUBMITTED ELECTRONICALLY

This application incorporates by reference a Sequence Listing submitted with this application as a text file entitled "13542-005-228_Sequence_Listing_ST25.txt" created on Dec. 1, 2015 and having a size of 199 kilobytes.

1. FIELD

Provided herein are methods of treating a nonhematopoietic malignant tumor in a patient and methods of prognosing a nonhematopoietic malignant tumor in a patient.

2. BACKGROUND

In the past decade, candidate gene, exome, and genome sequencing studies have delineated a spectrum of somatic mutations in human malignancies (Cancer Genome Atlas Network, 2012, Nature, 490: 61-70; Ellis, M. J., et al., 2012, Nature, 486: 353-360). These include large-scale sequencing studies in breast cancer, which have identified recurrent mutations in genes and pathways that contribute to malignant transformation and to therapeutic response. Cancer cells interact with their microenvironment, including stromal cell constituents, infiltrating leukocytes, and circulating inflammatory cytokines originating from local and distant sites (Acharyya, S., et al., 2012, Cell, 150: 165-178; Karnoub, A. E., et al., 2007, Nature, 449: 557-563). Previous studies have shown that stromal cells found in breast cancers are characterized by specific mutations and site-specific epigenetic alterations (Kurose, K., et al., 2002, Nat Genet, 32: 355-357; Hu, M., et al., 2005, Nat Genet, 37: 899-905). In addition to tissue-specific stromal cells, circulating and tumor-infiltrating leukocytes can mediate primary tumor growth and metastasis (Granot, Z., et al., 2011, Cancer Cell, 20: 300-314; Grivennikov, S. I., et al., 2010, Cell, 140: 883-899). Recent evidence suggests that tumor-associated stromal cells and infiltrating leukocytes function differently than circulating or bone marrow resident hematopoietic cells (Acharyya, S., et al., 2012, Cell, 150: 165-178; Orimo, A. and Weinberg, R. A., 2006, Cell Cycle, 5: 1597-1601; Li, H. J., et al., 2012, Cancer Discov, 2: 840-855). In particular, several studies have indicated that the content of lymphoid and myeloid cells infiltrating breast cancers correlates with clinical outcome (Mahmoud, S. M., et al., 2011, J Clin Oncol, 29: 1949-1955; Mohammed, Z. M., et al., 2013, Br J Cancer, 109: 1676-1684; Loi, S., et al., 2013, J Clin Oncol, 31: 860-867).

It was recently demonstrated that some older individuals have clinically inapparent, clonal hematopoiesis characterized by recurrent, somatic mutations in TET2 (Busque, L., et al., 2012, Nat Genet, 44: 1179-1181). Tet2 loss in the hematopoietic compartment leads to increased self-renewal and myeloid bias of hematopoietic cells (Moran-Crusio, K., et al., 2011, Cancer Cell, 20: 11-24; Quivoron, C., et al., 2011, Cancer Cell, 20: 25-38; Ko, M., et al., 2011, Proc Natl Acad Sci USA, 108: 14566-14571).

Citation of a reference herein shall not be construed as an admission that such is prior art to the present disclosure.

3. SUMMARY OF THE INVENTION

The present invention provides methods of treating a nonhematopoietic malignant tumor in a patient comprising administering to the patient a therapeutically effective amount of an agent (hereinafter "First Agent") that preferentially kills or inhibits proliferation or activity of leukocytes relative to nonhematopoietic cells.

In specific embodiments, the First Agent is imatinib, daunorubicin, cytarabine, decitabine, azacitidine, etoposide, mercaptopurine, prednisone, idelalisib, ibrutinib, or ABT-199.

In a specific embodiment wherein one or more somatic mutations are present in TET2 in tumor infiltrating leukocytes of the nonhematopoietic malignant tumor, the First Agent is decitabine. In another specific embodiment wherein one or more somatic mutations are present in TET2 in tumor infiltrating leukocytes of the nonhematopoietic malignant tumor, the First Agent is azacitidine. In another specific embodiment wherein one or more somatic mutations are present in IDH2 in tumor infiltrating leukocytes of the nonhematopoietic malignant tumor, the First Agent is decitabine. In another specific embodiment wherein one or more somatic mutations are present in IDH2 in tumor infiltrating leukocytes of the nonhematopoietic malignant tumor, the First Agent is azacitidine.

In various embodiments, the First Agent comprises a leukocyte-specific antibody. In a specific embodiment, the leukocyte-specific antibody is an anti-CD45 antibody. In a specific embodiment, the leukocyte-specific antibody is an anti-CD33 antibody. In a specific embodiment, the leukocyte-specific antibody is an anti-CD20 antibody. In a specific aspect of such an embodiment, the anti-CD20 antibody is rituximab.

In certain embodiments, the leukocyte-specific antibody is conjugated to a cytotoxic drug. In a specific embodiment, the First Agent is an anti-CD33 antibody conjugated to calicheamicin. In a specific aspect of such an embodiment, the anti-CD33 antibody conjugated to calicheamicin is gemtuzumab ozogamicin.

In various embodiments, the method of treating a nonhematopoietic malignant tumor in a patient as described above further comprises administering to the patient another agent (hereinafter "Second Agent"), different from the First Agent, to treat the nonhematopoietic malignant tumor. In specific embodiments, the Second Agent is trastuzumab, lapatinib, fluorouracil, paclitaxel, or a platinum analog. In some embodiments, the Second Agent is an inhibitor of HER2. In a specific aspect of such embodiments, the inhibitor of HER2 is an anti-HER2 antibody (for example, trastuzumab). In another specific aspect of such embodiments, the inhibitor of HER2 is lapatinib.

In specific embodiments, the Second Agent is a broad spectrum cancer treatment. In specific aspects, the broad spectrum cancer treatment is a chemotherapeutic agent. The chemotherapeutic agent can be, but is not limited to, an alkylating agent, an anti-metabolite, an anti-microtubule agent, a topoisomerase inhibitor, a cytotoxic antibiotic, an antibody-drug conjugate, or a combination thereof. In some embodiments, the chemotherapeutic agent is an alkylating agent. In some embodiments, the chemotherapeutic agent is an anti-microtubule agent (for example, a taxane). In some embodiments, the chemotherapeutic agent is a cytotoxic antibiotic (for example, an anthracycline).

In various embodiments, the method of treating a nonhematopoietic malignant tumor in a patient as described above further comprises treating the patient with radiation therapy. In a specific embodiment, the radiation therapy is local radiation therapy. In a specific embodiment, the radiation therapy is involved field radiation therapy.

In various embodiments, the method of treating a nonhematopoietic malignant tumor in a patient as described above further comprises treating the patient by surgically resecting the nonhematopoietic malignant tumor.

In various embodiments wherein the patient has one or more somatic gene mutations present in tumor infiltrating leukocytes of the nonhematopoietic malignant tumor, the method of treating a nonhematopoietic malignant tumor in the patient as described above further comprises prior to the administering step a step of determining that the one or more somatic gene mutations are present in the tumor infiltrating leukocytes.

In certain embodiments, the step of determining comprises comparing the DNA sequence of the tumor infiltrating leukocytes with the DNA sequence of non-cancerous cells. In some embodiments, the step of determining further comprises generating a report that indicates the presence of one or more somatic gene mutations in the tumor infiltrating leukocytes. In a specific aspect of such embodiments, the report further indicates the prognosis of the patient based upon the presence of one or more somatic gene mutations in the tumor infiltrating leukocytes. In some embodiments, the step of determining further comprises communicating the presence of one or more somatic gene mutations in the tumor infiltrating leukocytes. In some embodiments, the step of determining further comprises communicating (i) the presence of one or more somatic gene mutations in the tumor infiltrating leukocytes, and (ii) that the First Agent is a selected or indicated therapy for the patient. In some embodiments, the step of determining further comprises obtaining the tumor infiltrating leukocytes from the tissue of the nonhematopoietic malignant tumor. In some embodiments, the step of determining further comprises extracting DNA from the tumor infiltrating leukocytes. In some embodiments, the step of determining further comprises sequencing the DNA of the tumor infiltrating leukocytes.

The present invention also provides methods of prognosing a nonhematopoietic malignant tumor in a patient comprising determining whether tumor infiltrating leukocytes of the nonhematopoietic malignant tumor have one or more somatic gene mutations, wherein if the tumor infiltrating leukocytes have one or more somatic gene mutations, then the patient is indicated to have a worse prognosis than if the tumor infiltrating leukocytes do not have the one or more somatic gene mutations.

In some embodiments, the method of prognosing the nonhematopoietic malignant tumor further comprises treating the patient with a therapy, wherein the therapy is a more aggressive therapy if the tumor infiltrating leukocytes are determined to have the one or more somatic gene mutations, than if the tumor infiltrating leukocytes do not have the one or more somatic gene mutations.

In certain embodiments, the step of determining whether tumor infiltrating leukocytes of the nonhematopoietic malignant tumor have one or more somatic gene mutations comprises comparing the DNA sequence of the tumor infiltrating leukocytes with the DNA sequence of non-cancerous cells. In some embodiments, the step of determining whether tumor infiltrating leukocytes of the nonhematopoietic malignant tumor have one or more somatic gene mutations further comprises generating a report that indicates the presence or absence of one or more somatic gene mutations in the tumor infiltrating leukocytes. In a specific aspect of such embodiments, the report further indicates the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating (i) the presence or absence of one or more somatic gene mutations in the tumor infiltrating leukocytes, and (ii) the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises obtaining the tumor infiltrating leukocytes from the tissue of the nonhematopoietic malignant tumor. In some embodiments, the step of determining whether tumor infiltrating leukocytes of the nonhematopoietic malignant tumor have one or more somatic gene mutations further comprises extracting DNA from the tumor infiltrating leukocytes. In some embodiments, the step of determining whether tumor infiltrating leukocytes of the nonhematopoietic malignant tumor have one or more somatic gene mutations further comprises sequencing the DNA of the tumor infiltrating leukocytes.

The tumor infiltrating leukocytes in any of the methods described herein can be, but are not limited to, neutrophils, eosinophils, basophils, monocytes, macrophages, and/or lymphocytes.

In various embodiments of the methods described herein, the one or more somatic gene mutations are present in one or more genes selected from the group consisting of KDM5C, CDK8, MPL, ARID1A, FLT3, FGFR1, JAK1, GLI1, EZH2, EP300, BCOR, NF1, SMARCB1, EPHA10, IRF4, INSR, EPHA2, SMO, DUSP27, NOTCH2, HNF1A, MYO18A, MET, RPTOR, ATP10A, PTCH1, BRCA1, NCOR2, PASD1, NEB, MUC4, POU2F2, HLA-A, ALK, TET2, HLA-B, FGFR4, GATA2, FLT1, ATM, ITK, FREM2, INPP4B, CSF1R, PIGN, SOX17, MLL4, TTC28, TNFSF9, TRRAP, DNMT3A, TP53, IDH2, EPHA7, WT1, PNRC1, EGFR, ETV6, SMARCA4, MLL2, MAP3K1, ALOX12B, ARID2, EPHA8, ERBB2, EPHA4, PBRM1, BCL6, HDAC2, EPHA7, MLL, CYLD, CEBPA, JAK3, ASXL1, KIT, MEF2B, and ERG. In specific embodiments, the one or more somatic gene mutations are present in one or more genes selected from the group consisting of BCOR, NOTCH2, TET2, NF1, EZH2, JAK1, DNMT3A, and TP53. In a specific embodiment, the one or more somatic gene mutations are present in TET2. In a specific embodiment, the one or more somatic gene mutations are present in IDH2.

In specific embodiments, the one or more somatic gene mutations are in a coding region. In one aspect of such embodiments, the one or more somatic mutations result in an amino acid substitution. In another aspect of such embodiments, the one or more somatic gene mutations result in a premature stop codon.

In specific embodiments of the methods described herein, the nonhematopoietic malignant tumor is an epithelial tumor. The epithelial tumor can be, but is not limited to, a breast tumor, lung tumor, ovary tumor, stomach tumor, pancreas tumor, larynx tumor, esophagus tumor, testes tumor, liver tumor, parotid tumor, biliary tract tumor, colon tumor, rectum tumor, cervix tumor, uterus tumor, endometrium tumor, kidney tumor, bladder tumor, prostate tumor, or thyroid tumor. In a specific embodiment, the epithelial tumor is a breast tumor. In specific embodiments of the methods of treating a nonhematopoietic malignant tumor described herein, the nonhematopoietic malignant tumor is an epithelial tumor, and the First Agent preferentially kills or inhibits proliferation or activity of leukocytes relative to epithelial cells.

In a preferred embodiment of the methods described herein, the patient is a human patient.

4. BRIEF DESCRIPTION OF FIGURES

FIG. 1. Summary of the genetic analysis. The diagram outlines the steps used to filter the variants identified by whole-exome sequencing (a) and capture-based sequencing (b). *Indicates variants altering a codon previously reported in Catalogue Of Somatic gene mutations In Cancer (COSMIC) including different substitution of the same amino acid.

Figure 2:
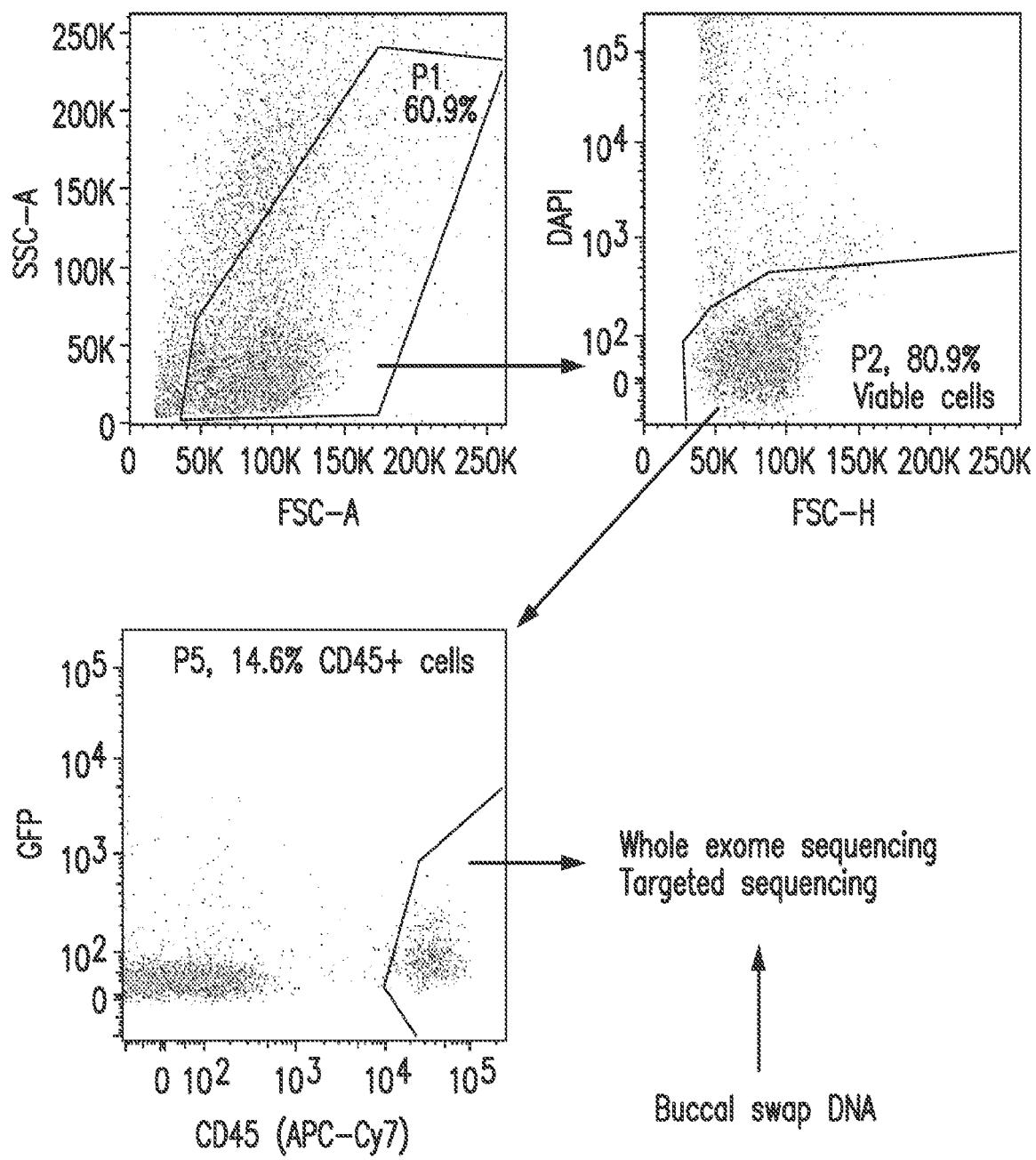
Figure 2:
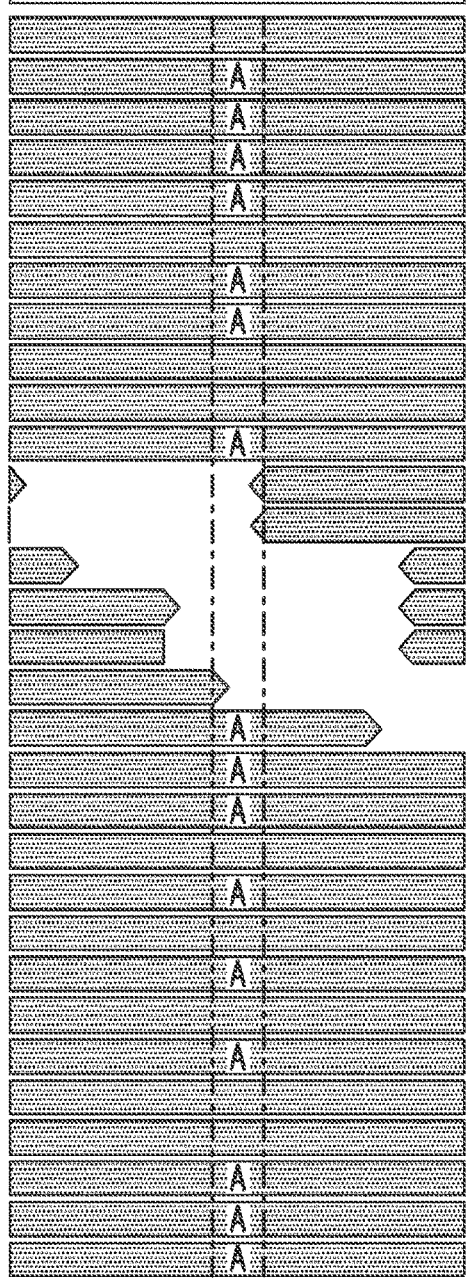

FIG. 2. Sequencing analysis of 21 primary breast cancers identified somatically acquired mutations in tumor-infiltrating leukocytes. (a) Gating scheme for fluorescent-activated cell sorting of CD45-positive hematopoietic cells (Patient #20). DAPI was included as live-dead stain. Cell doublets were excluded prior to gating on PE-Cy7 (not shown). DNA extracted from the CD45-positive fraction was analyzed using three independent sequencing platforms. (b) Representative IGV image showing the presence of acquired mutations. Reads that do not match the reference nucleotide are marked with the substituting nucleobase. Grey bar chart on top displays the read depth. Reference nucleotide and protein sequence are depicted for each mutation. Variant allele frequency (VAF) and the number of altered and total reads are shown (alt|total, VAF).

5. DETAILED DESCRIPTION

The present invention provides methods of treating a nonhematopoietic malignant tumor in a patient and methods of prognosing a nonhematopoietic malignant tumor in a patient. The inventors have discovered that tumor infiltrating leukocytes in some nonhematopoietic malignant tumors have somatically acquired mutations. According to the invention, tumor infiltrating leukocytes are targets in treating a nonhematopoietic malignant tumor and the presence of somatic mutations in tumor infiltrating leukocytes is a prognostic factor in prognosing a nonhematopoietic malignant tumor.

5.1. Methods of Treating a Nonhematopoietic Malignant Tumor

Provided herein are methods of treating a nonhematopoietic malignant tumor in a patient comprising administering to the patient a therapeutically effective amount of an agent (hereinafter "First Agent") that preferentially kills or inhibits proliferation or activity of leukocytes relative to nonhematopoietic cells.

In specific embodiments, the nonhematopoietic malignant tumor is a carcinoma, sarcoma, germ cell tumor, blastoma, or brain tumor. In specific embodiments, the nonhematopoietic malignant tumor is an epithelial tumor, and the First Agent preferentially kills or inhibits proliferation or activity of leukocytes relative to epithelial cells. The epithelial tumor can be, but is not limited to, a breast tumor, lung tumor, ovary tumor, stomach tumor, pancreas tumor, larynx tumor, esophagus tumor, testes tumor, liver tumor, parotid tumor, biliary tract tumor, colon tumor, rectum tumor, cervix tumor, uterus tumor, endometrium tumor, kidney tumor, bladder tumor, prostate tumor, or thyroid tumor. In a specific embodiment, the epithelial tumor is a breast tumor. In a specific embodiment, the nonhematopoietic malignant tumor is a malignant tumor of a particular tissue or organ type, and the First Agent preferentially kills or inhibits proliferation or activity of leukocytes relative to cells of such tissue or organ.

5.1.1. Treatment with the First Agent

The First Agent is any pharmaceutically acceptable agent that preferentially kills or inhibits proliferation or activity of leukocytes relative to nonhematopoietic cells. In various embodiments, the First Agent is an agent that is known or indicated to treat leukemia. In specific embodiments, the First Agent is imatinib, daunorubicin, cytarabine, decitabine, azacitidine, etoposide, mercaptopurine, prednisone, idelalisib, ibrutinib, or ABT-199.

First Agents are any known in the art, or can be identified by known methods. In particular, preferential killing or inhibition of proliferation or activity of leukocytes relative to nonhematopoietic cells can be determined by methods known in the art. As but one example, incubation of leukocytes and nonhematopoietic cells, respectively, with the same amount of candidate First Agent under the same or similar conditions, and detection of the percentage of cell death (or alternatively cell survival) can be carried out to determine whether an agent is a First Agent. Percentage of cell death can be determined, e.g., by use of dyes commonly used to determine cell viability.

In a specific embodiment wherein one or more somatic mutations are present in TET2 in tumor infiltrating leukocytes of the nonhematopoietic malignant tumor, the First Agent is decitabine. In another specific embodiment wherein one or more somatic mutations are present in TET2 in tumor infiltrating leukocytes of the nonhematopoietic malignant tumor, the First Agent is azacitidine. In another specific embodiment wherein one or more somatic mutations are present in IDH2 in tumor infiltrating leukocytes of the nonhematopoietic malignant tumor, the First Agent is decitabine. In another specific embodiment wherein one or more somatic mutations are present in IDH2 in tumor infiltrating leukocytes of the nonhematopoietic malignant tumor, the First Agent is azacitidine.

In various embodiments, the First Agent comprises a leukocyte-specific antibody. In a specific embodiment, the leukocyte-specific antibody is an anti-CD45 antibody. In a specific embodiment, the leukocyte-specific antibody is an anti-CD33 antibody. In a specific embodiment, the leukocyte-specific antibody is an anti-CD20 antibody. In a specific aspect of such an embodiment, the anti-CD20 antibody is rituximab.

In certain embodiments, the leukocyte-specific antibody is conjugated to a cytotoxic drug. In a specific embodiment, the First Agent is an anti-CD33 antibody conjugated to calicheamicin. In a specific aspect of such an embodiment, the anti-CD33 antibody conjugated to calicheamicin is gemtuzumab ozogamicin.

5.1.2. Nonhematopoietic Malignant Tumors Bearing Somatic Mutations in Tumor Infiltrating Leukocytes In various embodiments, the patient has one or more somatic gene mutations present in tumor infiltrating leukocytes of the nonhematopoietic malignant tumor. In a specific embodiment, the tumor infiltrating leukocytes are CD45+ cells isolated from a sample(s) (for example, obtained by biopsy or surgical resection) of the nonhematopoietic malignant tumor. The tumor infiltrating leukocytes can be, but are not limited to, neutrophils, eosinophils, basophils, monocytes, macrophages, and/or lymphocytes.

In specific embodiments, the one or more somatic gene mutations are present in one or more genes selected from the group consisting of KDM5C, CDK8, MPL, ARID1A, FLT3, FGFR1, JAK1, GLI1, EZH2, EP300, BCOR, NF1, SMARCB1, EPHA10, IRF4, INSR, EPHA2, SMO, DUSP27, NOTCH2, HNF1A, MYO18A, MET, RPTOR, ATP10A, PTCH1, BRCA1, NCOR2, PASD1, NEB, MUC4, POU2F2, HLA-A, ALK, TET2, HLA-B, FGFR4, GATA2, FLT1, ATM, ITK, FREM2, INPP4B, CSF1R, PIGN, SOX17, MLL4, TTC28, TNFSF9, TRRAP, DNMT3A, TP53, IDH2, EPHA7, WT1, PNRC1, EGFR, ETV6, SMARCA4, MLL2, MAP3K1, ALOX12B, ARID2, EPHA8, ERBB2, EPHA4, PBRM1, BCL6, HDAC2, EPHA7, MLL, CYLD, CEBPA, JAK3, ASXL1, KIT, MEF2B, and ERG. In specific embodiments, the one or more somatic gene mutations are present in one or more genes selected from the group consisting of BCOR, NOTCH2, TET2, NF1, EZH2, JAK1, DNMT3A, and TP53. In a specific embodiment, the one or more somatic gene mutations are present in TET2. In a particular embodiment, the one or more somatic gene mutations are present in human TET2, wherein the patient is a human patient. In a specific embodiment, the human TET2 has a wild-type sequence that is SEQ ID NO: 1. In a specific embodiment, the one or more somatic gene mutations are present in IDH2. In a particular embodiment, the one or more somatic gene mutations are present in human IDH2, wherein the patient is a human patient. In a specific embodiment, the human IDH2 has a wild-type sequence that is SEQ ID NO: 2.

In specific embodiments, the one or more somatic gene mutations are in a coding region. In one aspect of such embodiments, the one or more somatic mutations result in an amino acid substitution. In another aspect of such embodiments, the one or more somatic gene mutations result in a premature stop codon. By way of example, in specific embodiments, the one or more somatic mutations result in an amino acid substitution or a premature stop codon as shown in any of Table 4, Table 5, or Table 6.

5.1.3. Combination Therapy

In various embodiments, the method of treating a nonhematopoietic malignant tumor in a patient as described above further comprises administering to the patient another agent (hereinafter "Second Agent"), different from the First Agent, to treat the nonhematopoietic malignant tumor. In certain embodiments, the Second Agent is known or indicated to treat the nonhematopoietic malignant tumor. In a specific embodiment, the second agent preferentially kills or inhibits proliferation or activity of nonhematopoietic cells, e.g., of the same tissue as the nonhematopoietic malignant tumor, relative to leukocytes. In another specific embodiment, the Second Agent kills or inhibits proliferation or activity of leukocytes at about the same potency as it kills or inhibits proliferation or activity of cells of the same tissue as the nonhematopoietic malignant tumor. In specific embodiments, the Second Agent is trastuzumab, lapatinib, fluorouracil, paclitaxel, or a platinum analog. In some embodiments, the Second Agent is an inhibitor of HER2. In a specific aspect of such embodiments, the inhibitor of HER2 is an anti-HER2 antibody (for example, trastuzumab). In another specific aspect of such embodiments, the inhibitor of HER2 is lapatinib.

In specific embodiments, the Second Agent is a broad spectrum cancer treatment. In specific aspects, the broad spectrum cancer treatment is a chemotherapeutic agent. The chemotherapeutic agent can be, but is not limited to, an alkylating agent, an anti-metabolite, an anti-microtubule agent, a topoisomerase inhibitor, a cytotoxic antibiotic, an antibody-drug conjugate, or a combination thereof. In some embodiments, the chemotherapeutic agent is an alkylating agent. In some embodiments, the chemotherapeutic agent is an anti-microtubule agent (for example, an taxane). In some embodiments, the chemotherapeutic agent is a cytotoxic antibiotic (for example, an anthracycline).

In various embodiments, the method of treating a nonhematopoietic malignant tumor in a patient as described above further comprises treating the patient with radiation therapy. In a specific embodiment, the radiation therapy is local radiation therapy. In a specific embodiment, the radiation therapy is involved field radiation therapy.

In various embodiments, the method of treating a nonhematopoietic malignant tumor in a patient as described above further comprises treating the patient by surgically resecting the nonhematopoietic malignant tumor.

5.1.4. Routes of Administration and Dosage

Agents as described above (e.g., First Agent and Second Agent) may be administered to patients by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray.

Furthermore, one may administer the agent(s) described herein or a pharmaceutical composition thereof in a targeted drug delivery system, for example, in a liposome coated with an antibody specific for leukocytes. The liposomes will be targeted to and taken up selectively by the leukocytes.

The amount of agent described herein or a pharmaceutical composition thereof which will be effective in the treatment of the nonhematopoietic tumor will depend on the nature of the disease and the condition of the patient, and can be determined by standard clinical techniques and the knowledge of the physician.

The precise dose and regime to be employed in a composition will also depend on the route of administration, and the seriousness of the tumor, and should be decided according to the judgment of the physician and each patient's circumstance.

5.1.5. Methods of Detecting Somatic Mutations in Tumor Infiltrating Leukocytes.

In various embodiments wherein the patient has one or more somatic gene mutations present in tumor infiltrating leukocytes of the nonhematopoietic malignant tumor, the method of treating a nonhematopoietic malignant tumor in the patient as described above further comprises prior to the administering step a step of determining that the one or more somatic gene mutations are present in the tumor infiltrating leukocytes.

In a specific embodiment, the tumor infiltrating leukocytes are CD45+ cells isolated from a sample(s) (for example, obtained by biopsy or surgical resection) of the nonhematopoietic malignant tumor. The tumor infiltrating leukocytes can be neutrophils, eosinophils, basophils, monocytes, macrophages, and/or lymphocytes. The one or more somatic gene mutations can be present in locations as described above in Sections 5.1.2.

In certain embodiments, the step of determining comprises comparing the DNA sequence of the tumor infiltrating leukocytes with the DNA sequence of non-cancerous cells. In some embodiments, the step of determining further comprises generating a report that indicates the presence of one or more somatic gene mutations in the tumor infiltrating leukocytes. In a specific aspect of such embodiments, the report further indicates the prognosis of the patient based upon the presence of one or more somatic gene mutations in the tumor infiltrating leukocytes. In some embodiments, the step of determining further comprises communicating the presence of one or more somatic gene mutations in the tumor infiltrating leukocytes. In some embodiments, the step of determining further comprises communicating (i) the presence of one or more somatic gene mutations in the tumor infiltrating leukocytes, and (ii) that the First Agent is a selected or indicated therapy for the patient. In some embodiments, the step of determining further comprises obtaining the tumor infiltrating leukocytes from the tissue of the nonhematopoietic malignant tumor. In some embodiments, the step of determining further comprises extracting DNA from the tumor infiltrating leukocytes. In some embodiments, the step of determining further comprises sequencing the DNA of the tumor infiltrating leukocytes.

The tissue of the nonhematopoietic malignant tumor can be obtained by any method known in the art, for example, biopsy or surgical resection.

Obtaining tumor infiltrating leukocytes from the tissue of the nonhematopoietic malignant tumor can be performed by any method known in the art, for example, Fluorescence-Activated Cell Sorting (FACS) to isolate CD45+ cells from a sample(s) of the nonhematopoietic malignant tumor, as described in Example Section 6.1.2.

Extracting DNA from tumor infiltrating leukocytes can be performed by any method known in the art. Non-limiting exemplary methods for extracting DNA include salting-out methods, organic extraction methods, cesium chloride density gradient methods, anion-exchange methods, and silica-based methods (Green, M. R. and Sambrook J., 2012, Molecular Cloning (4th ed.), Cold Spring Harbor, N.Y.: Cold Spring Harbor Laboratory Press; Carpi F. M., et al., 2011, Recent Pat DNA Gene Seq, 5:1-7; Tan, S. C. and Yiap, B. C, 2009, J Biomed Biotechnol, Article ID 574398).

Sequencing the DNA of the tumor infiltrating leukocytes can be performed by any sequencing technologies known in the art. Non-limiting exemplary methods for sequencing of DNA include SOLiD sequencing (Shendure, J., et al., 2005, Science, 309: 1728-1732; McKernan, K. J., et al., 2009, Genome Res, 19: 1527-1541; Berglund, E. C., et al., 2011, Investig Genet, 2: 23; see also the Applied Biosystems website for a complete description of the technology), 454 sequencing (King, C. and Scott-Horton, T., 2008, J Vis Exp, (11): 630; Wheeler, D. A., et al., 2008, Nature, 452: 872-876; Berglund, E. C., et al., 2011, Investig Genet, 2: 23; see also the 454.com website for a complete description of the technology), Illumina (Solexa) sequencing (Bentley, D. R., et al., 2008, Nature, 456: 53-59; Balasubramanian, S., 2011, Chem Commun, 47: 7281-7286; Berglund, E. C., et al., 2011, Investig Genet, 2: 23; see also the Illumina website for a complete description of the technology), Ion Torrent semiconductor sequencing (Rusk, N., 2011, Nat Meth, 8: 44-44), DNA Nanoball sequencing (Porreca, G. J., 2010, Nat Biotechnol, 28: 43-44), Heliscope single molecule sequencing (Thompson, J. F. and Steinmann, K. E., 2010, Curr Protoc Mol Biol, Chapter 7: Unit 7), and single molecule real time (SMRT) sequencing (Eid, J, et al., 2009, Science, 323: 133-138). By way of example, in some embodiments, the step of sequencing the DNA of the tumor infiltrating leukocytes can be performed by whole exome sequencing, target capture sequencing, or a combination thereof, as shown in Example Section 6.1.5. In a specific embodiment, the step of determining further comprises sequencing the DNA of a non-tumorous sample (for example, a buccal swab sample) from the patient to provide a matched germline DNA sequence control, to identify somatic gene mutation(s) in the tumor infiltrating leukocytes.

Generating a report can be manually performed or computer-implemented using a computer system or computer-readable medium. In specific embodiments, the report further indicates the prognosis of the patient based upon the presence of one or more somatic gene mutations in the tumor infiltrating leukocytes. In specific embodiments, the report further indicates the name(s) of the gene(s) that are somatically mutated in the tumor infiltrating leukocytes of the patient. In further specific embodiments, the report further indicates the mutation(s) in the gene(s) that are somatically mutated in the tumor infiltrating leukocytes of the patient.

5.2. Methods of Prognosing a Nonhematopoietic Malignant Tumor

Also provided herein are methods of prognosing a nonhematopoietic malignant tumor in a patient comprising determining whether tumor infiltrating leukocytes of the nonhematopoietic malignant tumor have one or more somatic gene mutations, wherein if the tumor infiltrating leukocytes have one or more somatic gene mutations, then the patient is indicated to have a worse prognosis than if the tumor infiltrating leukocytes do not have the one or more somatic gene mutations.

In specific embodiments, the nonhematopoietic malignant tumor is a carcinoma, sarcoma, germ cell tumor, blastoma, or brain tumor. In specific embodiments, the nonhematopoietic malignant tumor is an epithelial tumor. The epithelial tumor can be, but is not limited to, a breast tumor, lung tumor, ovary tumor, stomach tumor, pancreas tumor, larynx tumor, esophagus tumor, testes tumor, liver tumor, parotid tumor, biliary tract tumor, colon tumor, rectum tumor, cervix tumor, uterus tumor, endometrium tumor, kidney tumor, bladder tumor, prostate tumor, or thyroid tumor. In a specific embodiment, the epithelial tumor is a breast tumor.

In a specific embodiment, the tumor infiltrating leukocytes are CD45+ cells isolated from a sample(s) (for example, obtained by biopsy or surgical resection) of the nonhematopoietic malignant tumor. The tumor infiltrating leukocytes can be, but are not limited to, neutrophils, eosinophils, basophils, monocytes, macrophages, and/or lymphocytes. The one or more somatic gene mutations can be present in locations as described above in Sections 5.1.1.

In some embodiments, the method of prognosing the nonhematopoietic malignant tumor further comprises treating the patient with a therapy, wherein the therapy is a more aggressive therapy (for example, greater drug potency or greater frequency of administration) if the tumor infiltrating leukocytes are determined to have the one or more somatic gene mutations, than if the tumor infiltrating leukocytes do not have the one or more somatic gene mutations. The therapy can be any method of treating a nonhematopoietic malignant tumor as described herein.

In certain embodiments, the step of determining whether tumor infiltrating leukocytes of the nonhematopoietic malignant tumor have one or more somatic gene mutations comprises comparing the DNA sequence of the tumor infiltrating leukocytes with the DNA sequence of non-cancerous cells. In some embodiments, the step of determining whether tumor infiltrating leukocytes of the nonhematopoietic malignant tumor have one or more somatic gene mutations further comprises generating a report that indicates the presence or absence of one or more somatic gene mutations in the tumor infiltrating leukocytes. In a specific aspect of such embodiments, the report further indicates the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises communicating (i) the presence or absence of one or more somatic gene mutations in the tumor infiltrating leukocytes, and (ii) the prognosis of the patient based upon the presence or absence of one or more somatic gene mutations in the tumor infiltrating leukocytes. In some embodiments, the step of determining whether tumor infiltrating leukocytes of the nonhematopoietic malignant tumor have one or more somatic gene mutations further comprises obtaining the tumor infiltrating leukocytes from the tissue of the nonhematopoietic malignant tumor. In some embodiments, the step of determining whether tumor infiltrating leukocytes of the nonhematopoietic malignant tumor have one or more somatic gene mutations further comprises extracting DNA from the tumor infiltrating leukocytes. In some embodiments, the step of determining whether tumor infiltrating leukocytes of the nonhematopoietic malignant tumor have one or more somatic gene mutations further comprises sequencing the DNA of the tumor infiltrating leukocytes.

The tissue of the nonhematopoietic malignant tumor can be obtained using methods described in Section 5.1.5.

Obtaining tumor infiltrating leukocytes from the tissue of the nonhematopoietic malignant tumor, extracting DNA from tumor infiltrating leukocytes, sequencing the DNA of the tumor infiltrating leukocytes, and generating a report can be performed using methods described in Section 5.1.5.

5.3. Patients

The patient referred to in this disclosure, can be, but is not limited to, a human or non-human vertebrate such as a wild, domestic or farm animal. In certain embodiments, the patient is a mammal, e.g., a human, a cow, a dog, a cat, a goat, a horse, a sheep, or a pig. In a preferred embodiment, the patient is a human patient.

In various embodiments, the patient has one or more somatic gene mutations present in tumor infiltrating leukocytes of the nonhematopoietic malignant tumor, as described in Section 5.1.2 above.

In specific embodiments, the patient is under the age of 70. In specific embodiments, the patient is under the age of 60. In specific embodiments, the patient is under the age of 55. In specific embodiments, the patient is under the age of 50.

6. EXAMPLE

This following non-limiting example demonstrates that somatic gene mutations, including in known cancer genes, are present in leukocytes infiltrating breast cancers.

6.1. Methods:

6.1.1. Patient Materials.

Breast cancer samples were collected from consecutive patients with primary triple negative breast cancer (TNBC) who underwent surgery at Memorial-Sloan Kettering Cancer Center (MSKCC) between 2012 and 2013 (Table 1). Patients treated with neoadjuvant chemotherapy were excluded from the study. Non-triple negative breast cancers showing prominent lymphocytic infiltrate in core biopsies were also included. All specimens were sectioned and processed for routine pathological examination. Hematoxylin and eosin (H&E) stained slides were reviewed by breast pathologists to establish the diagnoses. Estrogen receptor (ER), progesterone receptor (PR) and human epidermal growth factor receptor 2 (HER2) status was evaluated by immunohistochemistry (IHC). HER2 fluorescence in situ hybridization (FISH) was performed in one case with equivocal results by IHC. Evaluation of tumor infiltrating leukocytes was performed as previously described (Loi, S., et al., 2013, J Clin Oncol, 31: 860-867). Tumor-infiltrating leukocytes were scored as following: extensive ≥50% infiltration of either stromal or intratumoral lymphocytes; moderate=5-10%; minimal ≤5%. Buccal swab samples were collected from each patient. Mononuclear cells and granulocytes were isolated from peripheral blood following a standard Ficoll protocol. A detailed description on clinicopathological features of each patient is listed in Table 1.

TABLE 1

Summary of clinicopathological features

| ID | Age [y] | Type | TILs[#] | CD45 [%] | Size [cm] | HG | NG | Mitosis | OG | LVI | LN | ER | PR | HER2 | FISH |
|---|---|---|---|---|---|---|---|---|---|---|---|---|---|---|---|
| 1 | 40 | IDC NOS | Moderate | 36.6 | 2 | 3 | 3 | 3 | 3 | No | No | 0 | 0 | 0 | — |
| 2 | 72 | IDC NOS | Moderate | 11.89 | 1.5 | 3 | 3 | 3 | 3 | No | No | 0 | 0 | 0 | — |
| 3[+] | 37 | IDC NOS | Extensive | 12.5 | 4.5 | 3 | 3 | 3 | 3 | No | No | <1% | <1% | 1+ to 2+ | 1.3 |
| 4 | 35 | IDC NOS | Moderate | 0.4 | 5 | 2 | 3 | 3 | 3 | Yes | Yes | 95% | 90% | 3+ | — |
| 5 | 64 | ILC (C/P) | Minimal | 5.0 | 1 | 3 | 3 | 1 | 2 | No | No | 99% | 10% | 1+ | — |
| 6 | 62 | Apocrine | Moderate | 0.6 | 3.3 | 2 | 3 | 2 | 2 | Yes | Yes | 0 | 0 | 0 | — |
| 7 | 83 | IDC NOS | Moderate | 1.4 | 3.1 | 3 | 3 | 2 | 3 | Yes | No | 0 | 0 | 0 | — |
| 8 | 35 | IDC NOS | Moderate | 19.1 | 2.3 | 3 | 3 | 3 | 3 | No | No | 0 | 0 | 0 | — |
| 9 | 39 | IDC NOS | Extensive | 40.95 | 3 | 3 | 3 | 3 | 3 | No | No | 0 | 0 | 1+ | — |
| 10 | 62 | IDC NOS | Moderate | 7.6 | 1.8 | 3 | 3 | 3 | 3 | Yes | No | 0 | 0 | 1+ | — |
| 11[++] | 53 | IDC NOS | Minimal | 0.7 | 1.9 | 3 | 3 | 2 | 3 | No | N/A | 0 | 0 | 1+ | — |

TABLE 1-continued

Summary of clinicopathological features

| ID | Age [y] | Type | TILs# | CD45 [%] | Size [cm] | HG | NG | Mitosis | OG | LVI | LN | ER | PR | HER2 | FISH |
|---|---|---|---|---|---|---|---|---|---|---|---|---|---|---|---|
| 12 | 36 | IDC NOS | Extensive | 75.9 | 1.1 | 3 | 3 | 2 | 3 | No | No | 0 | 0 | 0 | — |
| 13 | 88 | Mucinous | Moderate | 0.3 | 6.6 | 2 | 1 | 1 | 1 | No | Yes | 95% | 60% | 0 | — |
| 14 | 56 | IDC NOS | Moderate | 1.4 | 2.5 | 3 | 3 | 3 | 3 | Yes | No | 5% | 5% | 3+ | — |
| 15++ | 65 | IDC NOS | Minimal | 1 | 2.1 | 3 | 3 | 3 | 3 | Yes | N/A | 0 | 5% | 1+ | — |
| 16* | 38 | IDC NOS | Moderate | 0.6 | 2.3 | 3 | 3 | 3 | 3 | No | No | 0 | 0 | 0 | — |
| 17 | 72 | IDC NOS | Moderate | 3 | 1.3 | 3 | 3 | 3 | 3 | No | No | 0 | 0 | 0 | — |
| 18 | 48 | IDC NOS | Moderate | 14.7 | 1.4 | 3 | 2 | 3 | 3 | Yes | No | 0 | 0 | 0 | — |
| 19 | 41 | IDC NOS | Moderate | 37 | 2.4 | 3 | 3 | 3 | 3 | No | No | 0 | 0 | 0 | — |
| 20 | 83 | IDC NOS | Extensive | 11.9 | 2.3 | 3 | 3 | 3 | 3 | No | No | 0 | 0 | 1+ | — |
| 21 | 45 | IDC NOS | Extensive | 77.4 | 0.7 | 3 | 3 | 3 | 3 | No | No | <1% | 10% | 0 | — |

+Patient with concurrent astrocytoma (WHO III);
++ipsilateral breast cancer recurrence;
*only whole-exome sequencing data available;
scoring criteria for the level of lymphocytic infiltration are defined above in Section 6.1.1.
IDC, invasive ductal carcinoma;
NOS, not otherwise specified;
ILC, invasive lobular carcinoma;
HG, histological grade,
NG, nuclear grade,
LVI, lymphovascular invasion;
LN, lymphnode involvement;
ER, estrogen receptor;
PR, progesterone receptor;
HER2, human epidermal growth factor receptor 2,
FISH, fluorescence in situ hybridization;
N/A, not sampled;
TILs, tumor infiltrating lymphocytes;
y, year.

6.1.2. Isolation and Processing of Tumor-Infiltrating Cells.

All patients included in this study gave informed consent. Fresh tumor cells, stromal cells, and tumor-infiltrating leukocytes were dissociated from the primary tumors by scraping the cutting surface 5-10 times with a surgical scalpel blade. Cell material was collected by rinsing the blade in PBS. Cells were spun down and resuspended in red cell lysis buffer to remove red blood cells prior to staining with an anti-human CD45-PE-Cy7 or CD45-APC-Cy7 conjugated flow antibody in FACS buffer (PBS supplemented with 2% BSA). Cells were stained for 20 min in the dark at room temperature, washed once with FACS buffer, and passed through a filter. DAPI was added before sorting to discriminate live and dead cells. CD45-positive cells were then purified using a FACSAriaIII Cell Sorter (MSKCC Flow Core Facility).

6.1.3. Laser Capture Microdissection of Tumor Cells.

Ten consecutive 8-μm-thick nuclear fast red-stained representative sections of the tumors were subjected to laser-assisted microdissection on a PALM Robot MicroBeam laser microdissection system, as previously described (Westbury, C. B., et al., 2009, J Pathol, 219: 131-140). First, non-neoplastic cells, including inflammatory cells, stroma and normal breast, were ablated. We subsequently microdissected only histologically unequivocal neoplastic cells from each sample under a microscope. Tissue was microdissected directly into extraction buffer, and DNA was extracted using the DNeasy Blood and Tissue Kit (Qiagen, Valencia, Calif.) and quantified with the Qubit Fluorometer (Invitrogen, Life Technologies, Norwalk, Conn.).

6.1.4. DNA Extraction and Whole Genome Amplification.

DNA was extracted using the QiaAmp DNA kit (Qiagen) following the manufacture instructions. Buccal swabs were processed using the QiaAmp DNA Mini kit (Qiagen) following the manufacture instructions. The quality of DNA samples was analyzed with the Agilent Bioanalyzer 2100. Samples with insufficient amount of DNA (<500 ng) were whole genome amplified (WGA) using the REPLI-g Mini kit (Qiagen) prior to further use in downstream applications. QPCR was performed to assess quality of WGA DNA.

6.1.5. Whole Exome Sequencing and Target Capture Sequencing.

DNA extracted from sorted CD45-positive tumor-infiltrating leukocytes and buccal swabs (Table 2) was sheared to an average size of 180 bp+/−80 bp for whole exome sequencing. For DNA library preparation, 200-250 bp fragments were selected and subjected to PCR amplification. The library was then hybridized to the Agilent SureSelect Human All Exon Kit and sequencing was performed on the SOLiD 3plus or SOLiD 4. Targeted sequencing of tumor infiltrating leukocytes and matched germline DNA of each patient was performed as previously described (Welch, J. S., et al., 2012, Cell, 150: 264-278).

TABLE 2

Mean target coverage information

| | | Mean target coverage | | |
|---|---|---|---|---|
| Sample source | Sample | IMPACT | Hem/600 | Exome |
| CD45+ cells | 1 | 99.81 | 91.48 | 39.70 |
| | 2 | 218.98 | 243.69 | 75.16 |
| | 3 | 358.14 | 392.53 | 66.93 |
| | 4 | 379.38 | 388.45 | 158.95 |
| | 5 | 386.30 | 345.25 | 84.95 |
| | 6 | 263.18 | 258.14 | 89.55 |
| | 7 | 417.28 | 413.19 | 123.42 |
| | 8 | 476.70 | 470.42 | 86.71 |
| | 9 | 375.74 | 388.05 | 120.25 |
| | 10 | 484.63 | 472.99 | 145.36 |
| | 11 | 319.04 | 411.89 | 150.99 |
| | 12 | 372.20 | 472.96 | 143.46 |

TABLE 2-continued

Mean target coverage information

| Sample source | Sample | IMPACT | Hem/600 | Exome |
|---|---|---|---|---|
| | 13 | 457.35 | 530.77 | 176.98 |
| | 14 | 442.33 | 506.16 | 142.88 |
| | 15 | 459.61 | 550.16 | 150.23 |
| | 16 | —* | —* | 155.18 |
| | 17 | 431.70 | 515.91 | 159.63 |
| | 18 | 799.54 | 502.30 | —* |
| | 19 | 463.57 | 609.66 | —* |
| | 20 | 778.25 | 595.60 | —* |
| | 21 | 435.52 | 516.34 | —* |
| Germline control | 1 | 219.87 | 354.11 | 110.69 |
| | 2 | 68.86 | 127.06 | —* |
| | 3 | 228.57 | 383.17 | 138.63 |
| | 4 | 182.19 | 273.96 | —* |
| | 5 | 260.48 | 377.91 | 136.01 |
| | 6 | 333.29 | 449.72 | —* |
| | 7 | 59.82 | 28.49 | —* |
| | 8 | 262.09 | 326.85 | 124.31 |
| | 9 | 176.59 | 242.46 | —* |
| | 10 | 283.65 | 274.74 | —* |
| | 11 | 321.25 | 706.71 | —* |
| | 12 | 228.89 | 499.60 | —* |
| | 13+ | 2.49 | 3.76 | —* |
| | 14 | 262.84 | 479.45 | 115.57 |
| | 15 | 112.34 | 205.98 | —* |
| | 17 | 283.08 | 553.12 | —* |
| | 18 | 299.22 | 677.35 | —* |
| | 19 | 331.03 | 680.13 | —* |
| | 20 | 307.91 | 458.01 | —* |
| | 21 | 268.68 | 520.76 | —* |

*Samples were not run at the indicated sequencing platform.
+CD45-positive sample of patient #13 was compared against pooled buccal swab samples due to low coverage of the matching germline DNA sample.

6.1.6. 454 Deep Sequencing Analysis.

Sequence reactions were performed on DNA extracted from mononuclear cells, granulocytes, laser capture microdissected tumor cells, and tumor-infiltrating leukocytes. All PCR reactions were performed using amplicon specific fusion primers. Fusion primers contained next to the template specific sequence a directional primer at the 5'-prime end followed by a multiplex identifier for barcode sample identification. Samples from 6-8 different patients were mixed, processed for 454 deep sequencing, and run on a Genome Sequencer FLX instrument. Data was mapped with BWA MEM (ver 0.7.4) to the full human genome. Multiple mapping reads (MAPQ=0) were removed and then the BAM files were processed for base recalibration using the GATK toolkit (ver 3.1). Mutations were called using the Haplotype caller which found only two events. In addition the read pileups were counted at each of the known mutation sites for each sample to compute the actual depth of both the reference and variant allele and to compute the non-reference allele frequency for each site.

6.1.7. Variant Detection.

Paired-end reads were aligned to the human hg19 genome with BWA 0.6.2-r126 (Iyer, G., et al., 2012, Science, 338: 221). Local realignment at indel regions and baseQ recalibration was done using the GATK suite version 2.8-1 and following recommendations of its authors (McKenna, A., et al, 2010, Genome Res, 20: 1297-1303). Variants in the targeted tumor-normal sample pairs were called with MuTect version 1.1.4. Variants passing the MuTect filters were annotated as high confidence (HC). Variants that were detected by the algorithm, but which failed to pass the MuTect filters were annotated as low confidence (LC). For whole-exome sequencing samples, SNPs and indels were called with the HaplotypeCaller from the GATK suite version 2.8-1. Variants that passed the GATK recommended filters and were not reported in any of the two buccal samples that were analyzed through the same pipeline or found in two or more non-somatic databases (non clinical variants from dbSNP, NHLBI exome sequencing project, and our own internal collection of normal tissues) were annotated as HC. Other variants were reported as LC.

6.1.8. Data Analysis.

A summary of the genetic analysis is depicted in FIG. 1. Briefly, for whole-exome sequencing samples, somatic variants (see Section 6.1.7) were further filtered against the Hem-Capture gene panel (Table 3) and IMPACT panel gene list to identify genes previously reported in hematological and epithelial malignancies, respectively. Identified variants occurring with a frequency ≥10% are shown in Table 4. No cut-off filter was applied to variants which were previously described in COSMIC (Catalogue Of Somatic Mutations In Cancer). Variants confirmed by three sequencing platforms were considered as somatic mutations independent of the allele frequency. In contrast, variants detected by two platforms were only considered somatic when occurring with an allele frequency of 10% or higher with the exception of variants previously described in COSMIC (no cut-off applied) (Table 5 and Table 6).

TABLE 3

Genes targeted by Hem-Capture sequencing panel
GENE

ABL1
AAMP
ABCA1
ABCA4
ABCA7
ABCD2
ACTB
ACTR3
ADAMTSL3
ADARB2
AFAP1
AGTR1
AIM1
AKAP6
AKAP8
AKT1
ALK
ALOX12B
ANKLE2
ANKRD11
ANP32E
APOBEC2
ARHGAP1
ARHGAP24
ARHGAP32
ARID1A
ARID1B
ARMC2
ARPP21
ARSB
ASAP1
ASMTL
ASXL1
ASXL2
ASXL3
ATF7IP
ATG5
ATIC
ATM
ATP10A
ATRX
ATXN1
B2M
BAALC

TABLE 3-continued

Genes targeted by Hem-Capture sequencing panel
GENE

BAP1
BCL10
BCL11A
BCL11B
BCL2
BCL2L10
BCL2L11
BCL6
BCL7A
BCOR
BCORL1
BCR
BIRC2
BIRC3
BLK
BLNK
BMI1
BNC2
BPTF
BRAF
BRPF1
BRSK1
BTG1
BTG2
BTLA
BTRC
C12orf35
C16orf48
C20orf94
C4orf14
C9orf53
CAMTA1
CARD11
CBL
CCBE1
CCDC102B
CCDC132
CCDC26
CCNC
CCND1
CCND2
CCND3
CD200
CD274
CD36
CD58
CD70
CD79A
CD79B
CD99
CDH13
CDK4
CDK6
CDKN2A
CDKN2B
CDKN2C
CEBPA
CHD1
CHD2
CHD7
CHD9
CIITA
CKS1B
CLEC16A
CLTC
CNOT3
CNTN4
COL4A2
CPS1
CREB1
CREBBP
CRLF2
CSF3R
CSMD3
CTCF
CTGF
CTNNA1
CTNNA3
CTNNB1
CUL4A
CYLC2
CYLD
D2HGDH
DCC
DCHS1
DCLRE1C
DDX3X
DEPDC5
DHCR7
DIS3
DLEU1
DLEU2
DLEU7
DMD
DNM2
DNMT3A
DOT1L
DPYD
DSC3
DTX1
DUSP2
DUSP22
DUSP27
DUSP9
DYRK1A
EAF2
EBF1
ECT2L
EED
EGFR
EGR1
EGR2
EIF3B
ELP2
EP300
EPHA7
EPOR
ERAP1
ERG
ESCO1
ESCO2
ETS1
ETV6
EXOSC6
EZH2
F3
F5
FAF1
FAM10A4
FAM46C
FAM84B
FANCL
FAS
FAT2
FBXO31
FBXW7
FDFT1
FDX1
FGA
FGFR3
FGG
FGR
FHIT
FLT3
FLYWCH1
FOXO1
FOXP1
FREM2
FRK
FUBP1
FYN
GABRA1
GALNTL6
GATA2

TABLE 3-continued

Genes targeted by Hem-Capture sequencing panel
GENE

GATA3
GJA3
GNA13
GOLGA3
GPR110
GPS2
GRB2
GRID1
GRIK2
GTSE1
H1FOO
HACE1
HCK
HDAC4
HDAC7
HERC1
HHEX
HIC1
HIST1H1B
HIST1H1C
HIST1H1E
HIST1H2AG
HIST1H2AL
HIST1H2BC
HIST1H2BE
HIST1H2BG
HIST1H2BK
HIST1H2BO
HIST1H3B
HLA-A
HLA-B
HMCN1
HMGB1
HNF1B
HNRNPA1
HNRNPR
HRAS
hsa-mir-15a
hsa-mir-16-1
HUWE1
HYDIN
ID3
IDH1
IDH2
IGF2BP3
IGHV
IGSF3
IKBIP
IKBKB
IKZF1
IKZF2
IKZF3
IL10RA
IL15
IL1RAP
IL3RA
IL7R
IL8
IMMP2L
ING1
IRAK1
IRAK4
IRF4
IRF8
ITK
ITPKB
JAK1
JAK2
JAK3
JAKMIP2
JMJD1C
JMJD4
KANK2
KCNRG
KDM2B
KDM4C
KDM5C TABLE 3-continued Genes targeted by Hem-Capture sequencing panel
GENE KDM6A
KDSR
KIF1B
KIT
KLF2
KLHL6
KLHL9
KRAS
KRTAP5-5
L2HGDH
LAMA5
LATS1
LATS2
LCK
LEF1
LMO2
LOC100130503
LOC400128
LOC440742
LOXL2
LPHN2
LPHN3
LPP
LRP1B
LRRIQ3
LRRK2
LYN
MAF
MAFB
MAGEC3
MAGED1
MALT1
MAP2
MAP2K2
MAP3K1
MAP3K14
MAP3K2
MAP3K7
MAPK1
MAPK14
MBNL1
MC4R
MCL1
MCPH1
MCRS1
MDM2
MDM4
MED12L
MEF2B
MEF2C
MIR17HG
MKI67
MKKS
MLL
MLL2
MLL3
MLL4
MLL5
MOB3A
MOB3B
MPL
MSH6
MSI1
MSI2
MSL2
MSR1
MSRA
MTAP
MTCP1
MTMR8
MTOR
MUC16
MUC2
MUC4
MYB
MYBL2
MYC TABLE 3-continued Genes targeted by Hem-Capture sequencing panel
GENE

| | |
|---|---|
| MYD88 | RAD21 |
| MYO18A | RAF1 |
| MYO1G | RAG1 |
| MYOM2 | RAG2 |
| NARS | RAPGEF1 |
| NBPF1 | RASGEF1A |
| NCOR1 | RB1 |
| NCOR2 | RCOR1 |
| NDST4 | RDX |
| NEB | REL |
| NF1 | RELN |
| NFATC1 | REV3L |
| NFKB1 | RGAG1 |
| NFKBIA | RGS12 |
| NFKBIE | RHOH |
| NFKBIZ | RIMS2 |
| NIPBL | RIPK4 |
| NKX2-1 | RNASEH2B |
| NOTCH1 | RNF213 |
| NOTCH2 | RPL10 |
| NPM1 | RPL5 |
| NR3C1 | RPS6KA1 |
| NR3C2 | RREB1 |
| NRAS | RUNX1 |
| NRXN3 | S1PR2 |
| NUP214 | SAMD9 |
| NXF1 | SCMH1 |
| OFD1 | SERPINA1 |
| OR6K3 | SESN1 |
| P2RY8 | SET |
| PABPC1 | SETBP1 |
| PABPC4L | SETD2 |
| PAG1 | SF1 |
| PAPOLG | SF3A1 |
| PASD1 | SF3B1 |
| PATL2 | SGK1 |
| PAX5 | SH2B3 |
| PCBP1 | SI |
| PCDH7 | SIN3A |
| PCDHB6 | SLC25A6 |
| PCLO | SLC38A8 |
| PDCD11 | SLC4A10 |
| PDCD1LG2 | SLC8A1 |
| PDGFC | SLITRK6 |
| PDS5B | SMARCA1 |
| PEAK1 | SMARCA4 |
| PFAS | SMARCB1 |
| PGAM5 | SMC1A |
| PHF6 | SMC3 |
| PI4K2B | SMYD1 |
| PIGN | SND1 |
| PIK3C2B | SNX25 |
| PIK3CA | SOCS1 |
| PIK3CD | SOCS2 |
| PIK3CG | SOX4 |
| PIK3R1 | SP100 |
| PIM1 | SPEN |
| PKDCC | SPG11 |
| PKHD1L1 | SPI1 |
| PLEKHG1 | SPIB |
| PLEKHG5 | SPRED1 |
| PMS1 | SRC |
| PNRC1 | SRCAP |
| POT1 | SRPX |
| POU2F2 | SRSF1 |
| PPP2R1B | SRSF2 |
| PPP2R5A | SRSF7 |
| PRAME | STAG1 |
| PRDM1 | STAG2 |
| PRDM2 | STAT3 |
| PRKCZ | STAT5A |
| PRKDC | STAT5B |
| PROX1 | STAT6 |
| PRPF40B | STIM2 |
| PTEN | STS |
| PTPN11 | SUZ12 |
| PTPN2 | SWAP70 |

TABLE 3-continued

Genes targeted by Hem-Capture sequencing panel
GENE

SYK
SYN2
TACC2
TAF1
TAL1
TBL1XR1
TCF12
TCF3
TCF4
TCF7
TCF7L2
TCL1A
TDRD6
TENM2
TET1
TET2
TET3
TFG
TFPI
TGM7
THADA
TLL2
TLR2
TLR4
TLR5
TLR6
TMEM30A
TMSL3
TMX3
TNF
TNFAIP3
TNFRSF11A
TNFRSF14
TNFRSF1A
TNFSF9
TOP2A
TOX
TP53
TP53INP1
TP63
TP73
TPM3
TRAF2
TRAF3
TRAF5
TRG@
TRIM13
TRIM69
TRO
TRRAP
TSC22D1
TTC18
TTC28
TTLL7
TUSC3
TYK2
U2AF1
U2AF2
UBE2A
UNC5C
UNC5D
VPS4B
VRK2
WAC
WDR7
WDR90
WHAMM
WHSC1
WHSC1L1
WT1
WWOX
XBP1
XPO1
YY1AP1
ZEB2
ZFHX3
ZFP36L1

TABLE 3-continued

Genes targeted by Hem-Capture sequencing panel
GENE

ZIC4
ZMYM2
ZMYM3
ZNF343
ZNF521
ZNF541
ZNF830
ZNF85
ZRSR2
ZWILCH

TABLE 4

Discovery variants identified by exome sequencing

| Sample | Gene | Mutation | Allele | Refseq Prot ID |
|---|---|---|---|---|
| 1 | KDM5C | p.A612T | 0.23 | NP 004178 |
| 2 | KDM5C | p.A612T | 0.47 | NP 004178 |
|  | CDK8 | p.V169I | 0.32 | NP 001251 |
|  | MPL | p.E54V | 0.2 | NP 005364 |
|  | ARID1A | p.Q1365K | 0.18 | NP 006006 |
|  | FLT3 | p.Q394* | 0.18 | NP 004110 |
|  | FGFR1 | p.G205D | 0.14 | NP 075598 |
|  | JAK1 | p.S260G | 0.13 | NP 002218 |
|  | GLI1 | p.G162C | 0.11 | NP 005260 |
| 3 | EZH2 | p.A478S | 0.46 | NP 004447 |
|  | EP300 | p.Q2355L | 0.33 | NP 001420 |
|  | EP300 | p.M1972T | 0.24 | NP 001420 |
| 4 | BCOR | p.P1156L | 0.46 | NP 001116857 |
|  | NF1 | p.K1517M | 0.32 | NP 001035957 |
|  | NF1 | p.A1670V | 0.25 | NP 001035957 |
|  | SMARCB1 | p.N154K | 0.14 | NP 003064 |
|  | EPHA10 | p.L80Q | 0.13 | NP 001092909 |
| 5 | IRF4 | p.M146I | 0.73 | NP 002451 |
|  | INSR | p.R162S | 0.53 | NP 000199 |
|  | EPHA2 | p.E302G | 0.2 | NP 004422 |
|  | SMO | p.A379V | 0.2 | NP 005622 |
|  | DUSP27 | p.Q737L | 0.12 | NP 001073895 |
| 6 | NOTCH2 | p.P1101T | 0.26 | NP 077719 |
|  | HNF1A | p.A562V | 0.18 | NP 000536 |
| 7 | MYO18A | p.A958V | 1 | NP 510880 |
|  | MET | p.Q165K | 0.2 | NP 000236 |
| 9 | RPTOR | p.V476M | 0.5 | NP 065812 |
| 10 | NOTCH2 | p.S1708P | 0.73 | NP 077719 |
|  | ATP10A | p.P35A | 0.51 | NP 077816 |
|  | PTCH1 | p.I685M | 0.41 | NP 000255 |
| 11 | IRF4 | p.A370V | 0.43 | NP 002451 |
|  | NF1 | p.N2775S | 0.43 | NP 001035957 |
|  | FGFR1 | p.M731V | 0.34 | NP 075598 |
| 12 | BRCA1 | p.S1613G | 0.99 | NP 009225 |
|  | NCOR2 | p.A1706T | 0.56 | NP 001070729 |
|  | DUSP27 | p.T1124N | 0.46 | NP 001073895 |
|  | PASD1 | p.Q213E | 0.23 | NP 775764 |
|  | BCOR | p.P1648L | 0.41 | NP 001116857 |
| 13 | NEB | p.Y1092C | 0.51 | NP 004534 |
|  | MUC4 | p.A2025V | 0.45 | NP 060876 |
|  | NOTCH2 | p.A21T | 0.35 | NP 077719 |
|  | POU2F2 | p.L459F | 0.25 | NP 002689 |
|  | HLA-A | p.A270S | 0.22 | NP 002107 |
|  | ALK | p.H1030P | 0.19 | NP 004295 |
|  | HLA-A | p.E176V | 0.18 | NP 002107 |
|  | TET2 | p.E1874K | 0.16 | NP 001120680 |
| 14 | HLA-B | p.R155S | 0.8 | NP 005505 |
|  | FGFR4 | p.S776F | 0.56 | NP 002002 |
|  | GATA2 | p.A286P | 0.46 | NP 001139133 |
|  | HLA-A | p.E176V | 0.41 | NP 002107 |
|  | ALK | p.H1030P | 0.16 | NP 004295 |
| 15 | HLA-B | p.R155S | 0.74 | NP 005505 |
|  | FLT1 | p.V1331I | 0.56 | NP 002010 |
|  | ATM | p.R2105S | 0.45 | NP 000042 |
|  | POU2F2 | p.L459F | 0.24 | NP 002689 |
|  | ALK | p.H1030P | 0.17 | NP 004295 |

TABLE 4-continued

Discovery variants identified by exome sequencing

| Sample | Gene | Mutation | Allele | Refseq Prot ID |
|---|---|---|---|---|
| 16 | HLA-A | p.E176V | 0.83 | NP 002107 |
| | HLA-B | p.R155S | 0.52 | NP 005505 |
| | ITK | p.D510N | 0.48 | NP 005537 |
| | FREM2 | p.G1608D | 0.45 | NP 997244 |
| | INPP4B | p.K816E | 0.44 | NP 003857 |
| | CSF1R | p.R216Q | 0.41 | NP 005202 |
| | PIGN | p.T569N | 0.38 | NP 789744 |
| | SOX17 | p.G178R | 0.38 | NP 071899 |
| | POU2F2 | p.L459F | 0.28 | NP 002689 |
| 17 | HLA-A | p.E176V | 0.6 | NP 002107 |
| | MLL4 | p.S214P | 0.59 | NP 055542 |
| | TTC28 | p.K2346Q | 0.54 | NP 001138890 |
| | TNFSF9 | p.A58S | 0.51 | NP 003802 |
| | TRRAP | p.S1073G | 0.46 | NP 003487 |
| | HLA-B | p.R155S | 0.32 | NP 005505 |
| | NOTCH2 | p.A21T | 0.23 | NP 077719 |
| | ALK | p.H1030P | 0.18 | NP 004295 |

TABLE 5

Somatic mutations in known cancer genes

| Sample | Gene | Mutation | Frequency | Refseq Prot Id |
|---|---|---|---|---|
| 1 | EP300 | p.G1777C | 0.06 | NP_001420 |
| 2 | DNMT3A | p.Y533C | 0.185 | NP_783328 |
| 3 | EZH2 | p.A483S | 0.46 | NP_004447 |
| | IDH2 | p.W164L | 0.13 | NP_002159 |
| | DNMT3A | p.T260N | 0.1 | NP_783328 |
| | TP53 | p.M169I | 0.029 | NP_001119585 |
| 4 | BCOR | p.P1156L | 0.49 | NP_001116857 |
| | EPHA7 | p.G592S | 0.14 | NP_004431 |
| | WT1 | p.T278I | 0.11 | NP_000369 |
| | TET2 | p.Q1702* | 0.06 | NP_001120680 |
| | PNRC1 | p.R97Q | 0.048 | NP_006804 |
| | EGFR | p.A871E | 0.042 | NP_005219 |
| 5 | ALK | p.R1209Q | 0.21 | NP_004295 |
| | ETV6 | p.P25S | 0.038 | NP_001978 |
| 6 | IDH2 | p.K205R | 0.245 | NP_002159 |
| | NOTCH2 | p.P1101T | 0.18 | NP_077719 |
| | NF1 | p.Q2434H | 0.099 | NP_001035957 |
| | SMARCA4 | p.D694E | 0.087 | NP_003063 |
| 12 | BCOR | p.P1613L | 0.483 | NP_001116857 |
| 13 | TET2 | p.E1874K | 0.17 | NP_001120680 |

Mutations listed in this table were identified by two or three independent platforms with an allele frequency of ≥10%. Mutations occurring at a lower frequency were included if previously reported in COSMIC.

TABLE 6

Somatic variants identified by at least two platforms

| Sample | Gene | Mutation | Chr | Position | Ref | Alt | IMPACT | Hem | Exome | Refseq_ProtID |
|---|---|---|---|---|---|---|---|---|---|---|
| 1 | EP300 | p.G1777C+ | chr22 | 41573044 | G | T | 0.024 | 0.06 | — | NP_001420 |
| | MLL2 | p.E4152K | chr12 | 49425224 | C | T | 0.88 | 0.953 | — | NP_003473.3 |
| | FLT3 | p.P439S | chr13 | 28610175 | G | A | 0.31 | 0.385 | — | NP_004110 |
| | MAP3K1 | p.S1002F | chr5 | 56178032 | C | T | 0.67 | 0.563 | — | NP_005912 |
| | ATM | p.P1564S | chr11 | 108164118 | C | T | 0.57 | 0.524 | — | NP_000042 |
| | ALOX12B | p.D492N | chr17 | 7979551 | C | T | 0.5 | 0.5 | — | NP_001130 |
| 2 | ARID1A | p.Q1365K | chr1 | 27100381 | C | A | 0.16 | 0.167 | 0.18 | NP_006006 |
| | KDM5C | p.A612T | chrX | 53231068 | C | T | 0.4 | 0.386 | 0.47 | NP_004178 |
| | JAK1 | p.S260G | chr1 | 65332761 | T | C | 0.17 | 0.154 | 0.13 | NP_002218 |
| | MPL | p.E54V | chr1 | 43803851 | A | T | 0.15 | 0.143 | 0.2 | NP_005364 |
| | FLT3 | p.Q394* | chr13 | 28622437 | G | A | 0.14 | 0.156 | 0.18 | NP_004110 |
| | TP53 | p.R248L | chr17 | 7577538 | C | A | 0.086 | 0.086 | — | NP_001119585 |
| | DNMT3A | p.Y533C | chr2 | 25467478 | T | C | 0.18 | 0.185 | — | NP_783328 |
| | GLI1 | p.G162C | chr12 | 57858988 | G | T | 0.11 | not targeted | 0.11 | NP_005260 |
| | CDK8 | p.V169I | chr13 | 26956999 | G | A | 0.23 | not targeted | 0.32 | NP_001251 |
| | FGFR1 | p.G205D | chr8 | 38285446 | C | T | 0.17 | not targeted | 0.14 | NP_075598 |
| | ALK | p.A892T | chr2 | 29451891 | C | T | 0.15 | 0.091 | — | NP_004295 |
| | BCL6 | p.K558M | chr3 | 187444554 | T | A | 0.18 | 0.196 | — | NP_001124317 |
| 3 | EP300 | p.M1972T | chr22 | 41573630 | T | C | 0.29 | 0.287 | 0.24 | NP_001420 |
| | EP300 | p.Q2355L | chr22 | 41574779 | A | T | 0.27 | 0.258 | 0.33 | NP_001420 |
| | EZH2 | p.A483S | chr7 | 148513834 | C | A | 0.18 | 0.259 | 0.46 | NP_004447 |
| | TP53 | p.M169I | chr17 | 7578423 | C | T | 0.029 | 0.024 | — | NP_001119585 |
| | IDH2 | p.W164L | chr15 | 90631862 | C | A | 0.13 | 0.108 | — | NP_002159 |
| | DNMT3A | p.T260N | chr2 | 25470982 | G | T | 0.1 | 0.101 | — | NP_783328 |
| | ATM | p.A1211T | chr11 | 108153491 | G | A | 0.15 | 0.112 | — | NP_000042 |
| 4 | NF1 | p.A1670V | chr17 | 29653011 | C | T | 0.25 | 0.238 | 0.25 | NP_001035957 |
| | SMARCB1 | p.N154K | chr22 | 24143230 | C | G | 0.14 | 0.149 | 0.14 | NP_001007469 |
| | BCOR | p.P1156L+ | chrX | 39923624 | G | A | 0.49 | 0.451 | 0.46 | NP_001116857 |
| | TET2 | p.Q1702+ | chr4 | 106196771 | C | T | 0.06 | 0.054 | — | NP_001120680 |
| | WT1 | p.T278I+ | chr11 | 32449541 | G | A | 0.11 | 0.112 | — | NP_000369 |
| | EPHA7 | p.G592S+ | chr6 | 93973602 | C | T | 0.14 | 0.129 | — | NP_004431 |
| | EGFR | p.A871E+ | chr7 | 55259554 | C | A | 0.037 | 0.042 | — | NP_005219 |
| | PNRC1 | p.R97Q | chr6 | 89790903 | G | A | 0.035 | 0.048 | — | NP_006804 |
| | MLL | p.A2061T | chr11 | 118371733 | G | A | 0.17 | 0.157 | — | NP_005924 |
| | CYLD | p.G173C | chr16 | 50785527 | G | T | 0.14 | 0.157 | — | NP_001035877 |
| | CEBPA | p.A79T | chr19 | 33793086 | C | T | 0.15 | 0.141 | — | NP_001272758 |
| | EPHA10 | p.L80Q | chr1 | 38227688 | A | T | 0.11 | not targeted | 0.13 | NP_001092909 |
| | NF1 | p.K1517M | chr17 | 29588764 | A | T | — | 0.121 | 0.32 | NP_001035957 |
| 5 | IRF4 | p.M146I | chr6 | 395881 | G | C | 0.69 | 0.667 | 0.73 | NP_002451 |
| | ETV6 | p.P25S+ | chr12 | 11905423 | C | T | 0.031 | 0.038 | — | NP_001978 |
| | ALK | p.R1209Q | chr2 | 29443591 | C | T | 0.21 | 0.221 | — | NP_004295 |
| | MLL2 | p.H4930L | chr12 | 49420150 | T | A | 0.18 | 0.149 | — | NP_003473.3 |

TABLE 6-continued

Somatic variants identified by at least two platforms

| Sample | Gene | Mutation | Chr | Position | Ref | Alt | IMPACT | Hem | Exome | Refseq_ProtID |
|---|---|---|---|---|---|---|---|---|---|---|
| | JAK3 | p.Q1094* | chr19 | 17937647 | G | A | 0.23 | 0.25 | — | NP_000206 |
| | ASXL1 | p.G792D | chr20 | 31022890 | G | A | 0.18 | 0.164 | — | NP_056153 |
| | KIT | p.G126E | chr4 | 55564489 | G | A | 0.36 | 0.237 | — | NP_000213 |
| | EPHA2 | p.E302G | chr1 | 16464844 | T | C | 0.1 | not targeted | 0.2 | NP_004422 |
| | DUSP27 | P.Q737L | chr1 | 167096578 | A | T | not | 0.102 | 0.12 | NP_001073895 |
| | MEF2B | P.P279S | chr19 | 19257149 | G | A | 0.26 | 0.343 | — | NP_001139257 |
| | ALK | p.L1145V | chr2 | 29445400 | G | C | 0.19 | 0.199 | — | NP_004295 |
| | ERG | p.P299L | chr21 | 39762961 | G | A | 0.13 | 0.151 | — | NP_001230357 |
| | SMO | p.A379V | chr7 | 128846206 | C | T | 0.17 | not targeted | 0.2 | NP_005622 |
| | INSR | p.R162S | chr19 | 7267524 | G | T | 0.6 | not targeted | 0.53 | NP_000199 |
| 6 | NOTCH2 | p.P1101T | chr1 | 120480516 | G | T | 0.18 | 0.174 | 0.26 | NP_077719 |
| | NF1 | p.Q2434H | chr17 | 29676250 | G | T | 0.094 | 0.099 | — | NP_001035957 |
| | SMARCA | p.D694E† | chr19 | 11118658 | C | A | 0.076 | 0.087 | — | NP_003063 |
| | MLL | p.K3846M | chr11 | 118392035 | A | T | 0.32 | 0.236 | — | NP_005924 |
| | IDH2 | p.K205R | chr15 | 90631655 | T | C | 0.11 | 0.245 | — | NP_002159 |
| | EP300 | p.R1737H | chr22 | 41572925 | G | A | 0.13 | 0.105 | — | NP_001420 |
| | KIT | p.G93S | chr4 | 55561887 | G | A | 0.12 | 0.129 | — | NP_000213 |
| | BCOR | p.V293I | chrX | 39933722 | C | T | 0.15 | 0.147 | — | NP_001116857 |
| | HNF1A | p.A562V | chr12 | 121437347 | C | T | 0.18 | not targeted | 0.18 | NP_000536 |
| | MEF2B | p.P197R | chr19 | 19257636 | G | C | 0.17 | 0.148 | — | NP_001139257 |
| 12 | BCOR | p.P1613L | chrX | 39913172 | G | A | 0.47 | 0.483 | 0.41 | NP_001116857 |
| | NCOR2 | p.A1706T | chr12 | 124826462 | C | T | not | 0.522 | 0.56 | NP_006303 |
| | BRCA1 | p.S1613G | chr17 | 41223094 | T | C | 1 | not targeted | 0.99 | NP_009231 |
| | PASD1 | p.Q213E | chrX | 150817094 | C | G | not | 0.437 | 0.23 | NP_775764 |
| | DUSP27 | p.T1124N | chr1 | 167097739 | C | A | not | 0.494 | 0.46 | NP_001073895 |
| 13 | TET2 | p.E1874K | chr4 | 106197287 | G | A | 0.17 | 0.138 | 0.15 | NP_001120680 |
| 15 | TP53 | p.R283P | chr17 | 7577090 | C | G | 0.055 | 0.065 | — | NP_001119585 |

Variants highlighted in bold were previously described in COSMIC.
†Indicates variants altering a codon previously reported in COSMIC, but result in a different substitution of the same amino acid.
Not targeted, specific gene not targeted by respective sequencing platform.
Ref, reference nucleotide;
alt, altered nucleotide;
chr, chromosome.
Data from three sequencing platforms (Hem-Capture panel (Hem), IMPACT, and whole-exome sequencing data) are shown.

6.2. Results:

Exome Sequencing of Infiltrating White Blood Cells

Fresh samples of seventeen untreated primary breast cancers were obtained (Table 1) and fluorescent activated cell sorting was performed to separate CD45-positive leukocytes from CD45-negative epithelial cells (FIG. 2a). Non-triple negative breast cancers showing a prominent lymphocytic infiltrate in core biopsies were also included in this study. Patients with neoadjuvant chemotherapy were not studied to exclude the effects of chemotherapy on mutational burden. Of the 17 patients, 13 had triple negative breast cancer, 2 had ER-positive, HER2-positive disease, and 2 had ER-positive, HER2-negative disease (Table 1). Exome sequencing of these CD45-positive tumor-infiltrating leukocytes was performed to investigate for the presence of mutations. Buccal swab samples of five patients (1, 3, 5, 8, and 14) were also analyzed by whole exome sequencing. Samples with insufficient amount of DNA were whole genome amplified (WGA) prior to further downstream applications. HaplotypeCaller (GATK suite version 2.8-1) was used to identify mutations present in tumor-infiltrating leukocytes that have not been reported in germline samples. Candidate variants called by GATK and which were not present in the buccal samples that were analyzed through the same pipeline and were not annotated as polymorphisms in SNP databases (see Section 6.1) were annotated as high confidence variants. This approach identified candidate mutations in known cancer genes, including in BCOR, NOTCH2, TET2, NF1, EZH2, and JAK1 (FIG. 2b, Table 4). Of importance, mutations in these genes were previously implicated in the pathogenesis of hematologic malignancies. The data suggest that mutations in known cancer genes are present in the white blood cells infiltrating a subset of breast cancers.

Confirmation of Identified Variants Using Targeted Sequencing Platforms

Although exome sequencing identified putative somatic mutations in known cancer genes in a subset of breast cancers, the limited coverage may limit the ability to identify mutations in infiltrating leukocytes. Therefore, in order to obtain coverage for genes with known roles in malignant transformation and to validate putative mutations identified in exome sequencing, capture-based sequencing of 20 paired tumor infiltrating-leukocyte and matched germline (buccal swab) DNA samples (Table 1) was performed. Two capture-based platforms that interrogate genes implicated in hematopoietic malignancies (Table 3 and Section 6.1) and in epithelial malignancies (Iyer, G., et al., 2012, Science, 338: 221) were used. Somatic variants identified by whole exome sequencing were further filtered against the two targeted sequencing panels to ensure the same variants were identified using higher coverage sequencing. All variants confirmed by three sequencing platforms and/or previously described in COSMIC and which were not identified in germline DNA were scored as somatic independent of allele frequency. Further, variants detected by two sequencing platforms and an allele frequency ≥10% and not identified in paired germline DNA were scored as somatic mutations. Following these criteria, we identified somatic mutations in 9 of the 20 patients (45%; Table 5 and Table 6). PCR and high coverage 454 sequencing on laser-capture dissected breast cancer cells was performed, the specific mutations that were detected was analyzed. Two TP53 mutations were present in purified breast cancer cells, suggesting that these mutations originated from the epithelial, malignant clone, and were censored (Table 7). By contrast, all other mutations were not identified in breast cancer cells consistent with their origin in the leukocyte component. These mutations included somatic mutations in known leukemia genes (DNMT3A TET2, BCOR, and TP53) which were present in tumor-infiltrating leukocytes. A subset of specific mutations was validated using original DNA, including mutations in TET2 (Patient 4: TET2 p.Q1702*) and BCOR (Patient 12: BCOR p.P1613L). The two TET2 mutations were likely pathogenic as a nonsense allele (TET2 p.Q1702*) and a mutation in a highly conserved residue in TET2 commonly mutated in myeloid malignancies (TET2 p.E1874K) were identified. Mutations in the transcriptional co-repressor BCOR, which is targeted by somatic mutations in myeloid leukemia, were identified in three patients. It is important to note that most of these mutations were present in at least 5-20% of reads. This suggests that these mutations were present in enriched subclones and were not rare alleles occurring in a minority of hematopoietic stem cells as previously reported in normal donors. A median of 7 mutations/case were identified in the nine patients with somatic mutations (Table 6). Mutations in tumor-infiltrating white blood cells were identified in all breast cancer subtypes and were present irrespective of the extent of leukocyte infiltrate as assessed by histopathologic assessment (Table 1).

TABLE 7

Deep sequencing of breast tumor cells

| Sample | Gene | Mutation | # variant reads | VAF tumor cells [%] | Coverage depth | VAF tumor infiltrating |
|---|---|---|---|---|---|---|
| 1 | EP300 | p.G1777C | 2 | 0.01 | 19460 | 6.0 |
| 2 | DNMT3A | p.Y533C | 1 | 0.01 | 17707 | 18.5 |
|   | TP53 | p.R248L | 6547 | 71.34 | 9177 | 8.6 |
| 3 | EZH2 | p.A483S | 0 | 0.00 | 14518 | 46.0 |
|   | IDH2 | p.W164L | 8 | 0.00 | 20529 | 13.0 |
|   | DNMT3A | p.T260N | 0 | 0.00 | 20135 | 10.1 |
|   | TP53 | p.M169I | 0 | 0.04 | 21792 | 2.9 |
| 4 | BCOR | p.P1156L | 4 | 0.05 | 8521 | 49.0 |
|   | EPHA7 | p.G592S | 1 | 0.01 | 9060 | 14.0 |
|   | WT1 | p.T278I | —* | —* | N/A | 11.0 |
|   | TET2 | p.Q1702* | 54 | 0.26 | 20909 | 6.0 |
|   | PNRC1 | p.R97Q | 9 | 0.16 | 5526 | 4.8 |
|   | EGFR | p.A871E | 0 | 0.00 | 5844 | 4.2 |
| 5 | ALK | p.R1209Q | 14 | 0.15 | 9426 | 21.0 |
|   | ETV6 | p.P25S | 0 | 0.00 | 3136 | 3.8 |
| 6 | IDH2 | p.K205R | 0 | 0.00 | 4758 | 24.5 |
|   | NOTCH2 | p.P1101T | —* | —* | —* | 18.0 |
|   | NF1 | p.Q2434H | 2 | 0.04 | 5361 | 9.9 |
|   | SMARCA4 | p.D694E | —* | —* | N/A | 8.7 |
| 12 | BCOR | p.P1613L | —† | —† | N/A | 48.3 |
| 13 | TET2 | p.E1874K | 356 | 2.03 | 17567 | 17.0 |
| 15 | TP53 | p.R283P | 21327 | 88.48 | 24104 | 6.5 |

VAF, variant allele frequency;
†no tumor sample obtainable;
*not sequenced;
N/A, not applicable.

Sequencing Analysis of Circulating Leukocytes

Sequencing of circulating leukocytes from these patients was next performed. Peripheral blood samples were prospectively obtained in a HIPAA-compliant and IRB-approved manner from 8 of the 10 patients in which somatic mutations had been identified in their tumor-infiltrating leukocytes. Two mutations (Patient 2: DNMT3A p.Y533C, Patient 12: BCOR p.P1613L) were detectable in circulating leukocytes (both mononuclear cells and granulocytes). The remaining 19 mutations were not detectable by sequencing in circulating leukocytes due to the limits of the sequencing coverage. Of note, the mutation in DNMT3A was present at 25-fold reduced variant allele frequency compared to tumor-infiltrating leukocytes (Table 8). It cannot be excluded that these other mutations were present in circulating cells at low allele burden, or alternatively or additionally, in stem/progenitor cells in the bone marrow from these patients. However, these data demonstrate that somatic mutations are highly enriched in tumor infiltrating leukocytes compared to the overall hematopoietic compartment.

TABLE 8

Deep sequencing of peripheral blood cells from breast cancer patients

| Sample | Gene | Mutation | # variant reads | VAF MNC [%] | Coverage depth | # variant reads | VAF Granulocytes [%] | Coverage depth | VAF tumor infiltrating leukocytes [%] |
|---|---|---|---|---|---|---|---|---|---|
| 1 | EP300 | p.G1777C | 3 | 0.01 | 44363 | 3 | 0.01 | 45130 | 6.0 |
| 2 | DNMT3A | p.Y533C | 363 | 0.73 | 50062 | 669 | 1.34 | 50046 | 18.5 |
|   | TP53 | p.R248L | 0 | 0.00 | 50013 | 3 | 0.01 | 50003 | 8.6 |
| 3 | EZH2 | p.A483S | 0 | 0.00 | 30057 | 0 | 0.00 | 23722 | 46.0 |
|   | IDH2 | p.W164L | 0 | 0.00 | 33870 | 0 | 0.00 | 30853 | 13.0 |
|   | DNMT3A | p.T260N | 0 | 0.00 | 38347 | 0 | 0.00 | 27035 | 10.1 |
|   | TP53 | p.M169I | 7 | 0.02 | 41638 | 4 | 0.01 | 38776 | 2.9 |
| 4 | BCOR | p.P1156L | 19 | 0.04 | 50003 | 10 | 0.02 | 49992 | 49.0 |
|   | EPHA7 | p.G592S | 10 | 0.02 | 50063 | 7 | 0.01 | 50045 | 14.0 |
|   | WT1 | p.T278I | 13 | 0.03 | 47802 | 14 | 0.03 | 41982 | 11.0 |
|   | TET2 | p.Q1702* | 20 | 0.04 | 49539 | 29 | 0.07 | 41051 | 6.0 |
|   | PNRC1 | p.R97Q | 20 | 0.04 | 50054 | 34 | 0.07 | 45952 | 4.8 |
|   | EGFR | p.A871E | 0 | 0.00 | 50069 | 1 | 0.00 | 50076 | 4.2 |
| 5 | ALK | p.R1209Q | 18 | 0.04 | 49999 | 20 | 0.04 | 49991 | 21.0 |
|   | ETV6 | p.P25S | 18 | 0.06 | 29627 | 33 | 0.08 | 42677 | 3.8 |

TABLE 8-continued

Deep sequencing of peripheral blood cells from breast cancer patients

| Sample | Gene | Mutation | # variant reads | VAF MNC [%] | Coverage depth | # variant reads | VAF Granulocytes [%] | Coverage depth | VAF tumor infiltrating leukocytes [%] |
|---|---|---|---|---|---|---|---|---|---|
| 6 | IDH2 | p.K205R | 50 | 0.10 | 50021 | 51 | 0.10 | 50050 | 24.5 |
|  | NOTCH2* | p.P1101T | — | — | — | — | — | — | 18.0 |
|  | NF1 | p.Q2434H | 0 | 0.00 | 50039 | 0 | 0.00 | 50040 | 9.9 |
|  | SMARCA4 | p.D694E | 1 | 0.00 | 50057 | 0 | 0.00 | 50051 | 8.7 |
| 12 | BCOR | p.P1613L | 21665 | 43.36 | 49967 | 20650 | 41.31 | 49983 | 48.3 |
| 13 | TET2* | p.E1874K | — | — | N/A | — | — | N/A | 17.0 |
| 15 | TP53 | p.R283P | 160 | 0.36 | 44534 | 132 | 0.31 | 42507 | 6.5 |

PB, peripheral blood;
MNC, mononuclear cells;
depth, number of total reads;
N/A, not applicable.
*not sequenced.

In this study, high throughput, next generation sequencing data were used to demonstrate that leukocytes with somatic mutations in known cancer genes infiltrate many primary cancers. Somatic mutations were identified and validated in ten of twenty patients, including in known leukemia genes (DNTM3A, TET2, and BCOR). In two cases, two mutations observed in the tumor-infiltrating leukocytes were also detected in the circulating leukocytes of the same patients but at a significantly lower frequency.

The data demonstrate that some nonhematopoietic cancers are characterized by infiltrating leukocytes with somatic mutations in known cancer genes.

7. INCORPORATION BY REFERENCE

Various publications are cited herein, the disclosures of which are hereby incorporated by reference herein in their entireties.

What is claimed is:

1. A method of treating mutant tumor-infiltrating leukocytes comprising:
determining that a patient having a nonhematopoietic malignant tumor comprising a breast tumor has one or more somatic gene mutations present in tumor-infiltrating leukocytes of the breast tumor, wherein the one or more somatic gene mutations are present in one or more genes selected from the group consisting of KDM5C, CDK8, MPL, ARID1A, FLT3, FGFR1, JAK1, GLI1, EZH2, EP300, BCOR, NF1, SMARCB1, EPHA10, IRF4, INSR, EPHA2, SMO, DUSP27, NOTCH2, HNF1A, MYO18A, MET, RPTOR, ATP10A, PTCH1, BRCA1, NCOR2, PASD1, NEB, MUC4, POU2F2, HLA-A, ALK, TET2, HLA-B, FGFR4, GATA2, FLT1, ATM, ITK, FREM2, INPP4B, CSF1R, PIGN, SOX17, MLL4, TTC28, TNFSF9, TRRAP, DNMT3A, TP53, IDH2, EPHA7, WT1, PNRC1, EGFR, ETV6, SMARCA4, MLL2, MAP3K1, ALOX12B, ARID2, EPHA8, ERBB2, EPHA4, PBRM1, BCL6, HDAC2, MLL, CPLD, CEBPA, JAK3, ASXL1, KIT, MEF2B, and ERG; are in a coding region, and result in an amino acid substitution or a premature stop codon; and are not identified in neoplastic cells of the breast tumor itself, said determining comprising:
obtaining a sample of tissue from the breast tumor;
isolating the tumor-infiltrating leukocytes from the tissue of the breast tumor;
extracting DNA from the tumor-infiltrating leukocytes; and
sequencing the DNA of the tumor-infiltrating leukocytes; and
administering to the patient determined to have the one or more somatic gene mutations present in the tumor-infiltrating leukocytes of the breast tumor an agent that preferentially kills or inhibits proliferation or activity of leukocytes relative to nonhematopoietic cells, wherein the agent is known or indicated to treat leukemia and is imatinib, daunorubicin, cytarabine, decitabine, azacitidine, etoposide, mercaptopurine, prednisone, idelalisib, ibrutinib, or ABT-199.

2. The method of claim 1, wherein the tumor-infiltrating leukocytes are neutrophils, eosinophils, basophils, monocytes, macrophages, and/or lymphocytes.

3. The method of claim 1, wherein the patient is a human patient.

4. The method of claim 1, wherein the patient has not had neoadjuvant chemotherapy.

5. The method of claim 1, wherein the tumor-infiltrating leukocytes are CD45+ cells.

6. The method of claim 1, wherein the one or more somatic gene mutations are selected from the group consisting of ALK p.A892T, ALK p.H1030P, ALK p.L1145V, ALK p.R1209Q, ALOX12B p.D492N, ARID1A p.Q1365K, ASXL1 p.G792D, ATM p.A1211T, ATM p.P1564S, ATM p.R2105S, ATP10A p.P35A, BCL6 p.K558M, BCOR p.P1156L, BCOR p.P1613L, BCOR p.P1648L, BCOR p.V293I, BRCA1 p.S1613G, CDK8 p.V169I, CEBPA p.A79T, CSF1R p.R216Q, CYLD p.G173C, DNMT3A p.T260N, DNMT3A p.Y533C, DUSP27 p.Q737L, DUSP27 p.T1124N, EGFR p.A871E, EP300 p.G1777C, EP300 p.M1972T, EP300 p.Q2355L, EP300 p.R1737H, EPHA2 p.E302G, EPHA7 p.G592S, EPHA10 p.L80Q, ERG p.P299L, ETV6 p.P25S, EZH2 p.A478S, EZH2 p.A483S, FGFR1 p.G205D, FGFR1 p.M731V, FGFR4 p.S776F, FLT1 p.V1331I, FLT3 p.P439S, FLT3 p.Q394*, FREM2 p.G1608D, GATA2 p.A286P, GLI1 p.G162C, HLA-A p.A270S, HLA-A p.E176V, HLA-B p.R155S, HNF1A p.A562V, IDH2 p.K205R, IDH2 p.W164L, INPP4B p.K816E, INSR p.R162S, IRF4 p.A370V, IRF4 p.M146I, ITK p.D510N, JAK1 p.S260G, JAK3 p.Q1094*, KDM5C p.A612T, KIT p.G126E, KIT p.G93S, MAP3K1 p.S1002F, MEF2B p.P197R, MEF2B p.P279S, MET p.Q165K, MLL p.A2061T, MLL p.K3846M, MLL2 p.E4152K, MLL2 p.H4930L, MLL4 p.S214P, MPL p.E54V, MUC4 p.A2025V, MYO18A p.A958V, NCOR2 p.A1706T, NEB p.Y1092C, NF1 p.A1670V, NF1 p.K1517M, NF1 p.N2775S, NF1 p.Q2434H, NOTCH2 p.A21T, NOTCH2 p.P1101T, NOTCH2 p.S1708P, PASD1 p.Q213E, PIGN p.T569N, PNRC1 p.R97Q, POU2F2 p.L459F, PTCH1 p.I685M, RPTOR p.V476M, SMARCA4 p.D694E, SMARCB1 p.N154K, SMO p.A379V, SOX17 p.G178R, TET2 p.E1874K, TET2 p.Q1702*, TNFSF9 p.A58S, TP53 p.M169I, TP53 p.R2'18L, TP53 p.R283P, TRRAP p.S1073G, TTC28 p.K2346Q, and WT1 p.T278I.

\* \* \* \* \*

UNITED STATES PATENT AND TRADEMARK OFFICE
CERTIFICATE OF CORRECTION

PATENT NO. : 10,962,543 B2  
APPLICATION NO. : 15/533911  
DATED : March 30, 2021  
INVENTOR(S) : Norton et al.

Page 1 of 1

It is certified that error appears in the above-identified patent and that said Letters Patent is hereby corrected as shown below:

In the Claims

Column 165 Line 19, "TP53 p.R2'18L, TP53 p.R283P," should be deleted.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*